United States Patent [19]
Weiser et al.

[11] Patent Number: 5,976,542
[45] Date of Patent: Nov. 2, 1999

[54] COMPOSITIONS AND METHODS FOR TREATMENT OF *STREPTOCOCCUS PNEUMONIAE* INFECTION

[75] Inventors: Jeffrey N. Weiser, Merion, Pa.; Andrew G. Plaut, Lexington; Joanne V. Gilbert-Rothstein, Arlington, both of Mass.

[73] Assignee: New England Medical Center, Boston, Mass.

[21] Appl. No.: 08/790,912

[22] Filed: Jan. 29, 1997

Related U.S. Application Data

[60] Provisional application No. 60/026,939, Sep. 23, 1996.

[51] Int. Cl.⁶ .......................... A61K 39/02; A61K 38/43; C12N 9/52; C12N 9/14
[52] U.S. Cl. ................. 424/190.1; 424/94.1; 424/244.1; 424/94.63; 424/184.1; 435/195; 435/220; 530/350
[58] Field of Search .............................. 424/244.1, 184.1, 424/190.1, 94.1, 94.63; 530/350; 435/195, 220

[56] References Cited

U.S. PATENT DOCUMENTS 4,879,213  11/1989  Fox et al. .

OTHER PUBLICATIONS

Paton et al. Ann. Rev. Microbiol. 1993, 47, 89–115.
Kilian. J. Immunol. 1988 vol. 124, No. 6, 2596–2600.
Burgess et al J. Cell. Biol. 1990 vol. 111, 2129–2138.
Lazar et al. Mol. Cell. Biol. 1988 vol. 8, No. 3, 1247–1252.
Plotkin et al (ed.) Published by W.B. Saunders Co., Philadelphia, 1988, p. 571.
Lacks et al., 1960, *Biochim Biophys. Acta.* 39:508–517.
Tiraby et al., 1973, *Proc. Natl. Acad. Sci. USA* 70:3541–3545.
Plaut et al., 1975, *Science* 190:1103–1105.
Sanger et al., 1977, *Proc. Natl. Acad. Sci. USA* 74:5463–5467.
Kilian et al., 1979, *Infect. Immun.* 26:143–149.
Male, 1979, *Infect. Immun.* 62:254–261.
Towbin et al., 1979, *Proc. Natl. Acad. Sci. USA* 76:4350–4354.
Kyte et al., 1982, *J. Mol. Biol.* 157:105–132.
Bricker et al., 1983, *Proc. Natl. Acad. Sci. USA* 80:2681–2685.
Plaut et al., 1983, *Ann. Rev. Microbiol.* 37:603–622.
Devereux et al., 1984, *Nucl. Acids. Res.* 12:387–395.
Koomey et al., 1984, *Immun.* 43:101–107.
Mortensen et al., 1984, *Infect. Immun.* 45:550–557.
Moxon et al., 1984, *J. Clin. Invest.* 73:298–306.
Achen et al., 1986, *Gene* 45:45–49.
Kett et al., 1986, *J. Immunol.* 136:3631–3635.
Monod et al., 1986, *J. Bacteriol.* 167:138–147.
von Heijne, 1986, *Nucl. Acids Res.* 14:4683–4690.
Pohlner et al., 1987, *Nature* (London) 325:458–462.
Takeshita et al., 1987, *Gene* 61:63–74.
Gilbert et al., 1988, *Infect. Immun.* 56:1961–1966.
Harlow et al., 1988, In: *Antibodies*, a Laboratory Manual, Cold Spring Harbor, NY. (Too voluminous to submit).
Jongeneel et al., 1989, *FEBS Lett.* 242:196–203.
Poulsen et al., 1989, *Infect. Immun.* 57:3097–3105.
Sambrook et al., 1989, *"Molecular Cloning: a Laboratory Manual"* Cold Spring Harbor, New York. (Too voluminous to submit).
Altschul et al., 1990, *J. Mol. Biol.* 215:403–410.
Fischetti et al., 1990, *Mol. Micro biol.* 4:1603–1605.
Klugman, 1990, *Clin. Microbiol. Rev.* 3:171–196.
Saraste et al., 1990, *Trends Biochem. Sci.* 15:430–434.
Vallee et al., 1990, *Proc. Natl. Acad. Sci. USA* 87:220–224.
Gilbert et al., 1991, *Infect. Immun.* 59:7–17.
Pearce et al., 1993, *Mol. Microbiol.* 9:1037–1050.
Tuallion et al., 1993, *Proc. Natl. Acad. Sci. USA* 90:3720.
Weiser et al., 1994, "Phase Variation in Pneumococcal Opacity: Relationship Between Colonial Morphology and Nasopharyngeal Colonization", *Infect. Immun.* 62(6):2582–2589.
Berry et al., "Effect of Defined Point Mutations in the Pneumolysin Gene on the Virulence of *Streptococcus Pneumoniae*", *Infect. Immun.* 63(5):1969–1974.
Gilbert et al,. 1995, *Infn. Immun.* 63:2682–2688.
Gordon and Breech, 1995, In: *The Antibodies* 1:.
Lomholt et al., 1995, *Infect. Immun.* 63:4238–4243.
Schneewind et al., 1995, *Science* 268:103–106.
Slauja et al., 1995, *Mol. Microbiol.* 16:215–227.
Tuomanen et al., 1995, *New Engl. J. Med.* 332:1280–1284.
Weiser et al., 1995, *Mol. Microbiol.* 17:555–564.
Qui et al., 1996, *Infect. Immun.* 64:933–937.
Weiser et al., 1996, *Infect. Immun.* 64:2240–2245.

*Primary Examiner*—Anthony C. Caputa
*Assistant Examiner*—John K. Weatherspoon
*Attorney, Agent, or Firm*—Panitch Schwarze Jacobs & Nadel, P.C.

[57] ABSTRACT

The invention relates to an isolated nucleic acid encoding *Streptococcus pneumoniae* IgA protease and an isolated polypeptide comprising *Streptococcus pneumoniae* IgA protease and methods of use thereof.

10 Claims, 34 Drawing Sheets

| PLASMID | CHANGE IN COLONY MORPHOLOGY |
|---|---|
| $O_1$ | + |
| pMU1328 | − |
| $O_1 \Delta E$ | − |
| $O_1 \Delta S$ | + |
| $O_1 \Delta K$ | − |
| $E_1 - X_1$ | − |
| $E_1 - E_2$ | + |

FIGURE 1

```
  1 gaa ttc TCC TCA ACT GCC TCA AAC CAT TTT TAG AAC GAT TAG TGA TAT GAG
  1     Glu Phe Ser Ser Thr Ala Ser Asn His Phe AMB Asn Asp AMB OPA Tyr Glu 52 TAA CAC CTA CCG TGT AAA TTT CAT GGT AGG TGT TAT TGT ACC CCC AAA TAA
 18 OCH His Leu Pro Cys Lys Phe His Gly Arg Cys Tyr Cys Thr Pro Lys OCH 103 TAT AAA ACA AAG TAT GAA AGC GCA TCT CAA TTT TAA GAC TTT TTT GTA AAT
 35 Tyr Lys Thr Lys Tyr Glu Ser Ala Ser Gln Phe OCH Asp Phe Phe Val Asn 154 TAA GAG TAT AAT TAA GGT ATA CTG CCT TTT CTA TAG ATA ATA GAT AAT ACA
 52 OCH Glu Tyr Asn OCH Gly Ile Leu Pro Phe Leu AMB Ile Ile Asp Asn Thr 205 CTA ATA TAA TAA AGG TCT TTG TAA CAT ATA ATT TAA ATT TTA TTT CAA GGA
 69 Leu Ile OCH OCH Arg Ser Leu OCH His Ile OCH Ile Leu Phe Gln Gly Gly 256 ATA ATG GAA AAG TAT TTT GGT GAA AAA CAA GAG CGT TTT TCA TTT AGA AAA
 86 Ile Met Glu Lys Tyr Phe Gly Glu Lys Gln Glu Arg Phe Ser Phe Arg Lys
        START 307 TTA TCA GTA GGA CTT GTA TCT GCA ACG ATT TCA AGT TTA TTT TTT ATG TCT
103 Leu Ser Val Gly Leu Val Ser Ala Thr Ile Ser Ser Leu Phe Phe Met Ser 358 GTA TTA GCT AGT TCA TCT GTG GAT GCT CAA GAA ACT GCG GGA GTT CAC TAT
120 Val Leu Ala Ser Ser Val Asp Ala Gln Glu Thr Ala Gly Val His Tyr
```

Fig. 4A

```
409 AAA TAT GTG GCA GAT TCA GAG CTA TCA GAA GAA AAG AAG CAG CTT GTC
137 Lys Tyr Val Ala Asp Ser Glu Leu Ser Glu Glu Lys Lys Gln Leu Val

460 TAT GAT ATT CCG ACA TAC GTG GAG AAT GAT GAT GAA ACT TAT TAT GTT
154 Tyr Asp Ile Pro Thr Tyr Val Glu Asn Asp Asp Glu Thr Tyr Tyr Val

511 TAT AAG TTA AAT TCT CAA AAT CAA CTG GCG GAA TTA CCA AAT ACT GGA AGC
171 Tyr Lys Leu Asn Ser Gln Asn Gln Leu Ala Glu Leu Pro Asn Thr Gly Ser

562 AAG AAT GAG AGG CAA GCC CTA GTT GCT GGT GCT AGC TTA GCT CTG GGA
188 Lys Asn Glu Arg Gln Ala Leu Val Ala Gly Ala Ser Leu Ala Leu Gly

613 ATT TTA ATT TTT GCT GTT TCC AAG AAA AAG GTT AAG AAT ACG GTA TTA
205 Ile Leu Ile Phe Ala Val Ser Lys Lys Lys Val Lys Asn Thr Val Leu

664 CAT TTA GTA TTG GTT GCG GGA ATG GGA AAT GGT GTC TTA GTT TCA GTC CAT
222 His Leu Val Leu Val Ala Gly Met Gly Asn Gly Val Leu Val Ser Val His

715 GCT TTA GAA AAT CAT CTT TTG CTA AAT TAC AAT ACG GAC TAT GAA TTG ACC
239 Ala Leu Glu Asn His Leu Leu Leu Asn Tyr Asn Thr Asp Tyr Glu Leu Thr

766 TCT GGA GAA AAA TTA CCT CTT CCT AAA GAG ATT TCA GGT TAC ACT TAT ATT
256 Ser Gly Glu Lys Leu Pro Leu Pro Lys Glu Ile Ser Gly Tyr Thr Tyr Ile
```

Fig. 4B

```
 817  GGA TAT ATC AAA GAG GGA AAA ACG ACT TCT GAT TTT GAA GTA AGT AAT CAA
 273  Gly Tyr Ile Lys Glu Gly Lys Thr Thr Ser Asp Phe Glu Val Ser Asn Gln

868  GAA AAA TCA GCA GCC ACT CCT ACA AAA CAA CAA AAG GTG GAT TAT AAT GTT
 290  Glu Lys Ser Ala Ala Thr Pro Thr Lys Gln Gln Lys Val Asp Tyr Asn Val

919  ACA CCA AAT TTT GTA GAC CAT CCA TCA ACA GTA CAA GCT ATT CAG GAA CAA
 307  Thr Pro Asn Phe Val Asp His Pro Ser Thr Val Gln Ala Ile Gln Glu Gln

970  ACA CCT GTT TCT TCA ACT AAG CCG ACA GAA GTT CAA GTA GTT GAA AAA CCT
 324  Thr Pro Val Ser Ser Thr Lys Pro Thr Glu Val Gln Val Val Glu Lys Pro

1021  TTC TCT ACT GAA TTA ATC AAT CCA AGA AAA GAA GAG AAA CAA TCT TCA GAT
 341  Phe Ser Thr Glu Leu Ile Asn Pro Arg Lys Glu Glu Lys Gln Ser Ser Asp

1072  TCT CAA GAA CAA TTA GCC AAA GAA CAT AAG AAA ACG TTA AAT CCA CAG GAT
 358  Ser Gln Glu Gln Leu Ala Lys Glu His Lys Lys Thr Leu Asn Pro Gln Asp

1123  AAG ATT TCT CCA AAA GAA AAG ACT GGG GTA AAT ACA CCT GAA GAG GAG
 375  Lys Ile Ser Pro Lys Glu Lys Thr Gly Val Asn Thr Leu Glu Glu Glu

1174  GAA GTT TTA TCA GGT CAA TTG AAC AAA CCT GAA CTC TTA TAT CGT GAG GAA
 392  Glu Val Leu Ser Gly Gln Leu Asn Lys Pro Glu Leu Leu Tyr Arg Glu Glu
```

Fig. 4C

```
1225 ACT ATA GAG ACA AAA ATA GAT TTT CAA GAA GAA ATT CAA GAA AAT CCT GAT
 409 Thr Ile Glu Thr Lys Ile Asp Phe Gln Glu Glu Ile Gln Glu Asn Pro Asp

1276 TTA GCT GAA GGA ACT GTA AGA GTA AAA CAA GAA AAA GGT AAA TTA GGT AAG AAA
 426 Leu Ala Glu Gly Thr Val Arg Val Lys Gln Glu Lys Gly Lys Leu Gly Lys Lys

1327 GTT GAA ATC GTC AGA ATA TTC TCT GTA AAC AAG GAA GAA GTT TCG CGA GAA
 443 Val Glu Ile Val Arg Ile Phe Ser Val Asn Lys Glu Glu Val Ser Arg Glu

1378 ATT GTT TCA ACT TCA ACG ACT GCG CCT AGT CCA AGA ATA GTC GAA AAA GGT
 460 Ile Val Ser Thr Ser Thr Thr Ala Pro Ser Pro Arg Ile Val Glu Lys Gly

1429 ACT AAA AAA ACT CAA GTT ATA AAG GAA CCT GAG ACT GGT GTA GAA CAT
 477 Thr Lys Lys Thr Gln Val Ile Lys Glu Pro Glu Thr Gly Val Glu His

1480 AAG GAC GTA CAG TCT GGA GCT ATT GTT GAA CCC GCA ATT CAG CCT GAG TTG
 494 Lys Asp Val Gln Ser Gly Ala Ile Val Glu Pro Ala Ile Gln Pro Glu Leu

1531 CCC GAA GCT GTA GTA AGT GAT AAA GGC GAA CCA GAA GTT CAA CCG ACA TTA
 511 Pro Glu Ala Val Val Ser Asp Lys Gly Glu Pro Glu Val Gln Pro Thr Leu

1582 CCC GAA GCA GTT GTG ACC GAC AAA GGT GAG ACT GAG GTT CAA CCA GAG TCG
 528 Pro Glu Ala Val Val Thr Asp Lys Gly Glu Thr Glu Val Gln Pro Glu Ser
```

Fig. 4D

```
1633  CCA GAT ACT GTG GTA AGT GAT AAA GGT GAA CCA GAG CAG GTA GCC CCA TTG
 545  Pro Asp Thr Val Val Ser Asp Lys Gly Glu Pro Glu Gln Val Ala Pro Leu

1684  CCA GAA TAT AAG GGT AAT ATT GAG CAA GTA AAA CCT GAA ACT CCG GTT GAG
 562  Pro Glu Tyr Lys Gly Asn Ile Glu Gln Val Lys Pro Glu Thr Pro Val Glu

1735  AAG ACC AAA GAA CAA GGT CCA GAA CAA GTT CCA GAA ACT GAA GTT AAA CCA
 579  Lys Thr Lys Glu Gln Gly Pro Glu Gln Val Pro Glu Thr Glu Val Lys Pro

1786  ACA GAA GAA ACA CCA GTA AAT CCA AAT GAA GGT ACT ACA GAA GGA ACC TCA
 596  Thr Glu Glu Thr Pro Val Asn Pro Asn Glu Gly Thr Thr Glu Gly Thr Ser

1837  ATT CAA GAA GCA GAA AAT CCA GTT CAA CCT GCA TCT AGC GAA GAA TCA ACA ACG AAT
 613  Ile Gln Glu Ala Glu Asn Pro Val Gln Pro Ala Ser Ser Glu Glu Ser Thr Thr Asn

1888  TCA GAG AAA GTA TCA GAT TCG ACA ACC TCA GTT GGA GAA AAT ACT GGG GAA GTG TCC
 630  Ser Glu Lys Val Ser Asp Ser Thr Thr Ser Val Gly Glu Asn Thr Gly Glu Val Ser

1939  AGT AAT CCT AGT GAT TCG ACA ACC TCA GTT GGA GAA AAT TCA AAT AAA CCA GAA
 647  Ser Asn Pro Ser Asp Ser Thr Thr Ser Val Gly Glu Asn Ser Asn Lys Pro Glu

1990  CAT AAT GAC TCT AAA AAT GAA TCA GAA AAT ACT GTA GAA GAA GTT CCA
 664  His Asn Asp Ser Lys Asn Glu Ser Glu Asn Thr Val Glu Glu Val Pro
```

Fig. 4E

```
2041 GTA AAT CCA AAT GAA GGC ACA GTA GAA GGT ACC TCA AAT CAA GAA ACA GAA
 681 Val Asn Pro Asn Glu Gly Thr Val Glu Gly Thr Ser Asn Gln Glu Thr Glu

2092 AAA CCA GTT CAA CCT GCA GAA ACA CAA GAA GAA ACA AAC TCT GGG AAA ATA GCT
 698 Lys Pro Val Gln Pro Ala Glu Thr Gln Glu Glu Thr Asn Ser Gly Lys Ile Ala

2143 AAC GAA AAT ACT GGA GAA GTA TCC AAT AAA CCT AGT GAT TCA AAA CCA CCA
 715 Asn Glu Asn Thr Gly Glu Val Ser Asn Lys Pro Ser Asp Ser Lys Pro Pro

2194 GTT GAA GAA TCA AAT CAA CCA ACA ACT GCA ACT GGA CAA ACA GAA CCA GAG AAA AAA
 732 Val Glu Glu Ser Asn Gln Pro Thr Thr Ala Thr Gly Gln Thr Glu Pro Glu Lys Lys

2245 AAT TCA GGT AAT ACA TCA GAG AAT GTT TCT GAT ATT GAG TTG TAT AGT CAG ACG AAT GGA
 749 Asn Ser Gly Asn Thr Ser Glu Asn Val Ser Asp Ile Glu Leu Tyr Ser Gln Thr Asn Gly

2296 CTC GAA TTA AGA AAT GTT TCA GAT GGA ATT CCA GAG AAT ACG GAT ACT
 766 Leu Glu Leu Arg Asn Val Ser Asp Gly Ile Pro Glu Asn Thr Asp Thr

2347 ACC TAC AGA CAA CAT GTT TCA TTG GAT GGA CAT TCA CCA GAG AAT ACG GAT ACT
 783 Thr Tyr Arg Gln His Val Ser Leu Asp Gly Ile Pro Glu Asn Thr Asp Thr

2398 TAC TTT GTC AAG GTA AAA TCT TCA GCA TTT AAA GAT GTC TAT ATA CCA GTA
 800 Tyr Phe Val Lys Val Lys Ser Ser Ala Phe Lys Asp Val Tyr Ile Pro Val
```

Fig. 4F

```
2449 GCT TCA ATA ACC GAA GAG AAA AGA AAT GGG CAG TCA GTT TAT AAA ATC ACA
 817 Ala Ser Ile Thr Glu Glu Lys Arg Asn Gly Gln Ser Val Tyr Lys Ile Thr

2500 GCC AAA GCT GAG AAA CTC CAG CAA GAA CTA AAT AAA TAT GTC GAC AAT
 834 Ala Lys Ala Glu Lys Leu Gln Gln Glu Leu Asn Lys Tyr Val Asp Asn

2551 TTC TCC TTC TAC CTC GAT AAG AAG GCT AAA GAG GAA AAT ACA AAC TTT ACT
 851 Phe Ser Phe Tyr Leu Asp Lys Lys Ala Lys Glu Glu Asn Thr Asn Phe Thr

2602 TCC TTT AGC AAC CTG GTC AAA GCT ATA AAC CAA AAT CCC TCT GGA ACC TAT
 868 Ser Phe Ser Asn Leu Val Lys Ala Ile Asn Gln Asn Pro Ser Gly Thr Tyr

2653 CAT TTA GCG GCC AGC CTG AAT GCT AAC GAA GTG GAG CTT GGT CCT GAT GAA
 885 His Leu Ala Ala Ser Leu Asn Ala Asn Glu Val Glu Leu Gly Pro Asp Glu

2704 AGA TCC TAT ATC AAG GAC ACC TTT ACT GGT CGT TTA ATC GGT GAA AAA GAT
 902 Arg Ser Tyr Ile Lys Asp Thr Phe Thr Gly Arg Leu Ile Gly Glu Lys Asp

2755 GGC AAG ATT TAT AAT TTG AAA AAA CCT CTG TTT GAA AAC TTG
 919 Gly Lys Ile Tyr Asn Leu Lys Lys Pro Leu Phe Glu Asn Leu

2806 AGT GGT GCT ACA GTA GAA AAA CTG AGT CTA AAA AAT GTT GCT ATT TCA GGG
 936 Ser Gly Ala Thr Val Glu Lys Leu Ser Leu Lys Asn Val Ala Ile Ser Gly
```

Fig. 4G

```
2857  AAA AAT GAT ATT GGT TCA CTG GCA AAT GAA GCT ACG AAT GGC ACA AAG ATT
953   Lys Asn Asp Ile Gly Ser Leu Ala Asn Glu Ala Thr Asn Gly Thr Lys Ile

2908  AAA CAA GTT CAT GTT GAT GGT GTT CTG GCT GGA GAA CGT GGT GTC GGT GGT
970   Lys Gln Val His Val Asp Gly Val Leu Ala Gly Glu Arg Gly Val Gly Gly

2959  TTG GCT AAG GCA GAC CAA TCA GAC CAG ATC GCA GAG AGC AGT TTC AAG GGA
987   Leu Leu Ala Lys Ala Asp Gln Ser Asp Gln Ile Ala Glu Ser Ser Phe Lys Gly

3010  AGA ATT GTC AAT ACC TAT GAA ACG ACT GAT GCC TAC AAT ATT GGC GGT CTG
1004  Arg Ile Val Asn Thr Tyr Glu Thr Thr Asp Ala Tyr Asn Ile Gly Gly Leu

3061  GTC GGT CAT TTA ACA GGA AAA AAT GCG TCT ATT GCT AAA TCC AAA GCG ACA
1021  Val Gly His Leu Thr Gly Lys Asn Ala Ser Ile Ala Lys Ser Lys Ala Thr

3112  GTA ACC ATT TCG TCA AAC ACC AAT AGG TCA GAT CAG ACT GTC GGT GGT CTT
1038  Val Thr Ile Ser Ser Asn Thr Asn Arg Ser Asp Gln Thr Val Gly Gly Leu

3163  GCA GGT CTA GTA GAC CAA GAT GCG CAT ATA CAG AAC AGT TAT GCG GAA GGT
1055  Ala Gly Leu Val Asp Gln Asp Ala His Ile Gln Asn Ser Tyr Ala Glu Gly

3214  GAT ATT AAT AAT GTC AAG CAC TTT GGT AAA GTC GCT GGT GTG GCA GGA TAT
1072  Asp Ile Asn Asn Val Lys His Phe Gly Lys Val Ala Gly Val Ala Gly Tyr
```

Fig. 4H

```
3265 TTG TGG GAT CGA ACT TCT GGT GAG GAA AAA CAC GCT GGT GAA TTG ACC AAT
1089 Leu Trp Asp Arg Thr Ser Gly Glu Glu Lys His Ala Gly Glu Leu Thr Asn

3316 GTT CTT AGC GAT GTC AAT GTA ACA AAC GGA AAT GCC ATC ACT GGA TAC CAC
1106 Val Leu Ser Asp Val Asn Val Thr Asn Gly Asn Ala Ile Thr Gly Tyr His

3367 TAT ACA GGA ATG AAG GTA GCT AAT ACA TTT AGT AAG GCT AAT AGA GTT
1123 Tyr Thr Gly Met Lys Val Ala Asn Thr Phe Ser Ser Lys Ala Asn Arg Val

3418 TTC AAT GTC ACT TTA GAG AAG GAT GAG GTC AGC AAA GAA TCC TTT GAA
1140 Phe Asn Val Thr Leu Glu Lys Asp Glu Val Ser Lys Glu Ser Phe Glu

3469 GAA AGA GGA ACA ATG CTA GAT GCT TCT CAA ATT GTA AGC AAA AAA GCA GAA
1157 Glu Arg Gly Thr Met Leu Asp Ala Ser Gln Ile Val Ser Lys Lys Ala Glu

3520 ATA AAT CCT CTC ACT CTA CCA ACG GTG GAA CCC CTC TCA ACA AGT GGC AAG
1174 Ile Asn Pro Leu Thr Leu Pro Thr Val Glu Pro Leu Ser Thr Ser Gly Lys

3571 AAA GAC AGT GAT TTT TCT AAG ATA GCC CAT TAT CAA GCT AAC CGT GCT TTG
1191 Lys Asp Ser Asp Phe Ser Lys Ile Ala His Tyr Gln Ala Asn Arg Ala Leu

3622 GTT TAT AAG AAC ATT GAA AAA TTG TTA CCT TTT TAT AAT AAG TCA ACC ATC
1208 Val Tyr Lys Asn Ile Glu Lys Leu Leu Pro Phe Tyr Asn Lys Ser Thr Ile
```

Fig. 4I

```
3673  GTC AAA TAC GGA AAC CTG GTT AAG GAG AAC AGT CTC TTA TAC CAA AAA GAA
1225  Val Lys Tyr Gly Asn Leu Val Lys Glu Asn Ser Leu Leu Tyr Gln Lys Glu

3724  CTC TTA TCT GCA GTT ATG ATG AAG GAT GAC CAA GTA ATC ACA GAT ATT GTT
1242  Leu Leu Ser Ala Val Met Met Lys Asp Asp Gln Val Ile Thr Asp Ile Val

3775  TCC AAC AAA CAG ACT GCA AAC AAA CTC TTA CTT CAC TAT AAT GAC CAT TCA
1259  Ser Asn Lys Gln Thr Ala Asn Lys Leu Leu Leu His Tyr Asn Asp His Ser

3826  TCT GAG AAA TTT GAT CTC AAG TAC CAG ACT GAT TTT GCC AAT CTA CCA GAA
1276  Ser Glu Lys Phe Asp Leu Lys Tyr Gln Thr Asp Phe Ala Asn Leu Pro Glu

3877  TAT AAT CTA GGT AAT ACG GGA CTT CTC TAC ACT CCT AAC CAA TTC TTA TAT
1293  Tyr Asn Leu Gly Asn Thr Gly Leu Leu Tyr Thr Pro Asn Gln Phe Leu Tyr

3928  GAT CGA GAC TCT ATT GTT AAG GAA GTC TTG CCT GAG TTG CAG AAG CTT GAT
1310  Asp Arg Asp Ser Ile Val Lys Glu Val Leu Pro Glu Leu Gln Lys Leu Asp

3979  TAC CAG TCA GAT GCT ATC AGA AAG ACA CTT GGT ATT TCT CCA GAA GTT AAG
1327  Tyr Gln Ser Asp Ala Ile Arg Lys Thr Leu Gly Ile Ser Pro Glu Val Lys

4030  TTA ACC GAG CTC TAT TTA GAA GAC CAG TTC TCC AAA ACA AAA CAA AAT CTG
1344  Leu Thr Glu Leu Tyr Leu Glu Asp Gln Phe Ser Lys Thr Lys Gln Asn Leu
```

```
4081 GGA GAC AGC TTG AAA AAA CTT TTG TCA GCA GAT GCC GGT CTA GCT AGC GAT
1361 Gly Asp Ser Leu Lys Lys Leu Leu Ser Ala Asp Ala Gly Leu Ala Ser Asp

4132 AAC TCA GTC ACC AGA GGC TAT CTT GTA GAT AAA ATC AAG AAT AAT AAG GAA
1378 Asn Ser Val Thr Arg Gly Tyr Leu Val Asp Lys Ile Lys Asn Asn Lys Glu

4183 GCC TTG CTA CTC GGT TTA ACT TAT TTA GAA CGT TGG TAT AAC TTT AAC TAT
1395 Ala Leu Leu Leu Gly Leu Thr Tyr Leu Glu Arg Trp Tyr Asn Phe Asn Tyr

4234 GGT CAA GTG AAT GTC AAA GAC CTA GTT ATG TAT CAT CCA GAC TTC TTT GGT
1412 Gly Gln Val Asn Val Lys Asp Leu Val Met Tyr His Pro Asp Phe Phe Gly

4285 AAA GGA AAT ACT TCC CCA CTA GAT ACT CTG ATT GAG TTA GGT AAA TCT GGC
1429 Lys Gly Asn Thr Ser Pro Leu Asp Thr Leu Ile Glu Leu Gly Lys Ser Gly

4336 TTT AAC AAT CTT CTA GCT AAG AAT GTC GAT TTT GGT TAT GGT ATC AGT CTT
1446 Phe Asn Asn Leu Leu Ala Lys Asn Val Asp Phe Gly Tyr Gly Ile Ser Leu

4387 GCC AGT CAA CAT GGA GCG ACA GAT TTG TTT AGC ACG CTG GAA CAT TAC CGA
1463 Ala Ser Gln His Gly Ala Thr Asp Leu Phe Ser Thr Leu Glu His Tyr Arg

4438 AAA GTC TTT TTA CCA AAT ACA AGC AAT AAT GAC TGG TTT AAA TCA GAG ACT
1480 Lys Val Phe Leu Pro Asn Thr Ser Asn Asn Asp Trp Phe Lys Ser Glu Thr
```

```
4489 AAG GCT TAC ATT GTC GAA GAA AAA TCC ACT ATC GAA GAG GTG AAA ACG AAG
1497 Lys Ala Tyr Ile Val Glu Glu Lys Ser Thr Ile Glu Val Lys Thr Lys

4540 CAA GGG TTA GCT GGC ACC AAG TAT TCT ATC GGT GTT TAT GAT CGT ATC ACG
1514 Gln Gly Leu Ala Gly Thr Lys Tyr Ser Ile Gly Val Tyr Asp Arg Ile Thr

4591 AGT GCC ACA TGG AAA TAC CGC AAT ATG GTC TTG CCT CTC CTG ACC TTG CCA
1531 Ser Ala Thr Trp Lys Tyr Arg Asn Met Val Leu Pro Leu Leu Thr Leu Pro

4642 GAG AGA TCC GTA TTT GTC ATC TCG ACC ATG TCT AGT CTA GGA TTT GGA GCT
1548 Glu Arg Ser Val Phe Val Ile Ser Thr Met Ser Leu Gly Phe Gly Ala

4693 TAT GAT CGC TAC CGC AGT AGT GAC CAT AAA GCG GGC AAG GCT CTC AAT GAT
1565 Tyr Asp Arg Tyr Arg Ser Ser Asp His Lys Ala Gly Lys Ala Leu Asn Asp

4744 TTT GTT GAA GAA AAT GCG CGT GAA ACA GCC AAA CGT CAG CGA AAA ACT CTA TTC
1582 Phe Val Glu Glu Asn Ala Arg Glu Thr Ala Lys Arg Gln Arg Lys Thr Leu Phe

4795 GAT TAT TGG TAT CGT ATT TTA GTG AAC AGT CAA CGG CGA TAT AAG TTT GGG GAT GAC TAC
1599 Asp Tyr Trp Tyr Arg Ile Leu Val Asn Ser Gln Arg Arg Lys Phe Gly Asp Asp His Tyr

4846 GTA CGA TTC TCC CTT TAT GAT GCC TAT AAG TTT GGG GAT GAC ACA TCA
1616 Val Arg Phe Ser Leu Tyr Asp Ala Tyr Lys Phe Gly Asp Asp Thr Thr Ser
```

Fig. 4L

```
4897 GGA AAA GCT ACA GCG GAG GCT AAG TTT GAT AGC TCC AAT CCA GCT ATG AAG
1633 Gly Lys Ala Thr Ala Glu Ala Lys Phe Asp Ser Ser Asn Pro Ala Met Lys

4948 AAC TTC TTT GGA CCA GTT GGC AAT AAG GTA GTA CAC AAC CAG CAT GGA GCC
1650 Asn Phe Phe Gly Pro Val Gly Asn Lys Val Val His Asn Gln His Gly Ala

4999 TAC GCT ACA GGG GAC GGC GTC TAC TAT ATG TCT TAC CGC ATG CTG GAC AAG
1667 Tyr Ala Thr Gly Asp Gly Val Tyr Tyr Met Ser Tyr Arg Met Leu Asp Lys

5050 GAT GGA GCC ATT AAT TAT ACC CAT GAA ATG ACC CAT GAT TCG GAT CAG GAT
1684 Asp Gly Ala Ile Asn Tyr Thr His Glu Met Thr His Asp Ser Asp Gln Asp

5101 ATT TAC CTT GGT GGC TAT GGT CGA AGA AAT GGC TTG GGA CCA GAG TTT TTT
1701 Ile Tyr Leu Gly Gly Tyr Gly Arg Arg Asn Gly Leu Gly Pro Glu Phe Phe

5152 GCA AAA GGC TTA TTG CAA GCC CCT GAC CAA AGT GAC GCA ACC ATT ACC
1718 Ala Lys Gly Leu Leu Gln Ala Pro Asp Gln Pro Ser Asp Ala Thr Ile Thr

5203 ATT AAT TTT ATT TTG AAA CAC TCA AAA TCA GAT AGT ACA GAG GGA TCC CGT
1735 Ile Asn Phe Ile Leu Lys His Ser Lys Ser Asp Ser Thr Glu Gly Ser Arg

5254 CTT CAA GTC TTG GAT CCG ACA GAG AGA TTC CAA AAC GCA GCA GAT TTT CAG
1752 Leu Gln Val Leu Asp Pro Thr Glu Arg Phe Gln Asn Ala Ala Asp Phe Gln
```

Fig. 4M

```
5305 AAC TAT GTC CAT AAC ATG TTT GAC CTT ATC TAC ATG ATG GAA TAT CTC GAA
1769 Asn Tyr Val His Asn Met Phe Asp Leu Ile Tyr Met Met Glu Tyr Leu Glu

5356 GGG CAG TCA ATC GTT AAT AAA CTA AGT GTT TAC CAG AAA ATG GCG GCT CTC
1786 Gly Gln Ser Ile Val Asn Lys Leu Ser Val Tyr Gln Lys Met Ala Ala Leu

5407 AGA AAA ATT GAG AAC AAG TAT GTG AAA GAT CCA GCA GAT GGA AAT GAG GTT
1803 Arg Lys Ile Glu Asn Lys Tyr Val Lys Asp Pro Ala Asp Gly Asn Glu Val

5458 TAT GCC ACT AAC GTA GTC AAA GAA TTG ACA GAA GCA GAG GCC CGA AAC CTG
1820 Tyr Ala Thr Asn Val Val Lys Glu Leu Thr Glu Ala Glu Ala Arg Asn Leu

5509 AAT AGT TTT GAA AGT TTG ATT GAC CAC AAC ATC TTA TCA GCT CGT GAG TAC
1837 Asn Ser Phe Glu Ser Leu Ile Asp His Asn Ile Leu Ser Ala Arg Glu Tyr

5560 CAG TCT GGC GAC TAT GAA CGA AAT GGC TAC TAT ACC ATC AAA CTC TTT GCC
1854 Gln Ser Gly Asp Tyr Glu Arg Asn Gly Tyr Tyr Thr Ile Lys Leu Phe Ala

5611 CCA ATC TAT TCA GCT AGT CTC AGC AGT GAG AAA GGC ACA CCA GGG GAC CTT ATG
1871 Pro Ile Tyr Ser Ala Leu Ser Ser Glu Lys Gly Thr Pro Gly Asp Leu Met

5662 GGA CGT AGG ATT GCG TAC GAA CTT TTG GCT GCC AAA GGC TTT AAG GAT GGA
1888 Gly Arg Arg Ile Ala Tyr Glu Leu Leu Ala Ala Lys Gly Phe Lys Asp Gly
```

Fig. 4N

```
5713  ATG  GTA  CCT  TAT  ATC  TCA  AAC  CAA  TAC  GAA  GAA  GAT  GCT  AAA  CAA  CAA  GGG
1905  Met  Val  Pro  Tyr  Ile  Ser  Asn  Gln  Tyr  Glu  Glu  Asp  Ala  Lys  Gln  Gln  Gly

5764  CAA  ACT  ATC  AAT  CTT  TAT  GGT  AAA  GAA  CGG  GGC  TTG  GTG  ACC  GAT  GAG  CTT
1922  Gln  Thr  Ile  Asn  Leu  Tyr  Gly  Lys  Glu  Arg  Gly  Leu  Val  Thr  Asp  Glu  Leu

5815  GTT  TTG  AAA  AAG  GTA  TTT  GAC  GGT  AAG  TAT  AAA  ACT  TGG  GCA  GAA  TTT  AAG
1939  Val  Leu  Lys  Lys  Val  Phe  Asp  Gly  Lys  Tyr  Lys  Thr  Trp  Ala  Glu  Phe  Lys

5866  ACA  GCT  ATG  TAC  CAA  GAA  CGG  TGG  ATC  AGT  TTG  GGA  AAC  TTG  AAG  CAG  GTG
1956  Thr  Ala  Met  Tyr  Gln  Glu  Arg  Trp  Ile  Ser  Leu  Gly  Asn  Leu  Lys  Gln  Val

5917  ACC  TTT  AAA  GAT  CCG  ACA  AAA  CCA  TGG  CCA  AGC  TAT  GGC  ACA  AAG  ACT  ATC
1973  Thr  Phe  Lys  Asp  Pro  Thr  Lys  Pro  Trp  Pro  Ser  Tyr  Gly  Thr  Lys  Thr  Ile

5968  AAT  AAT  GTG  GAT  GAA  TTG  CAA  GCC  CTC  ATG  GAC  CAA  GCT  GTT  CTC  AAG  GAT
1990  Asn  Asn  Val  Asp  Glu  Leu  Gln  Ala  Leu  Met  Asp  Gln  Ala  Val  Leu  Lys  Asp

6019  GCT  GAA  GGT  CCA  CGT  TGG  AGT  AAT  TAT  GAT  CCA  GAA  ATC  GAC  AGT  GCC  GTT
2007  Ala  Glu  Gly  Pro  Arg  Trp  Ser  Asn  Tyr  Asp  Pro  Glu  Ile  Asp  Ser  Ala  Val

6070  CAT  AAG  TTG  AAG  AGA  GCA  ATC  TTT  AAA  GCC  TAT  CTT  GAC  CAA  ACA  AAT  GAT
2024  His  Lys  Leu  Lys  Arg  Ala  Ile  Phe  Lys  Ala  Tyr  Leu  Asp  Gln  Thr  Asn  Asp
```

Fig. 40

```
6121 TTT AGA AGT TCA ATT TTT GAG AAT AAA AAA TAG TGT TTA CTA TTA GGA AAT
2041 Phe Arg Ser Ser Ile Phe Glu Asn Lys Lys AMB Cys Leu Leu Leu Gly Asn
                                            STOP

6172 AAA GTT TAA AAA GGT GAT GAA AAA CAA CCC
2058 Lys Val OCH Lys Gly Asp Glu Lys Gln Pro
```

Fig. 4P

1    MEKYFGEKQERFSFRKLSVGLVSATISSLFFMSVLASSSVDAQETAGVHYKYVADSELSSEEKKQLVYDI

71   PTYVENDDETYYLVYKLNSQNQLAELPNTGSKNERQALVAGASLAALGILIFAVSKKKVKNKTVLHLVLV

141  AGMGNGVLVSVHALENHLLLNYNTDYELTSGEKLPLPKEISGYTYIGYIKEGKTTSDFEVSNQEKSAATP

211  TKQQKVDYNVTPNFVDHPSTVQAIQEQTPVSSTKPTEVQVVEKPFSTELINPRKEEKQSSDSQEQLAEHK

281  NLETKKEEKISPKEKTGVNTLNPQDEVLSGQLNKPELLYREETIETKIDFQEEIQENPDLAEGTVRVKQE

351  GKLGKKVEIVRIFSVNKEEVSREIVSTSTTAPSPRIVEKGTKKTQVIKEQPETGVEHKDVQSGAIVEPAI

421  QPELPEAVVSDKGEPEVQPTLPEAVVTDKGETEVQPESPDTVVSDKGEPEQVAPLPEYKGNIEQVKPETP

491  VEKTKEQGPEKTEEVPVKPTEETPVNPNEGTTEGTSIQEAENPVQPAEESTTNSEKVSPDTSSENTGEVS

561  SNPSDSTTSVGESNKPEHNDSKNENSEKTVEEVPVNPNEGTVEGTSNQETEKPVQPAEETQTNSGKIANE

631  NTGEVSNKPSDSKPPVEESNQPEKNGTATKPENSGNTTSENGQTEPEKKLELRNVSDIELYSQTNGTYRQ

701  HVSLDGIPENTDTYFVKVKSSAFKDVYIPVASITEEKRNGQSVYKITAKAEKLQQELENKYVDNFSFYLD

Fig. 5A

```
 771  KKAKEENTNFTSFSNLVKAINQNPSGTYHLAASLNANEVELGPDERSYIKDTFTGRLIGEKDGKIYAIYN
 841  LKKPLFENLSGATVEKLSLKNVAISGKNDIGSLANEATNGTKIKQVHVDGVLAGERGVGGLLAKADQSSI
 911  AESSFKGRIVNTYETTDAYNIGGLVGHLTGKNASIAKSKATVTISSNTNRSDQTVGGLAGLVDQDAHIQN
 981  SYAEGDINNVKHFGKVAGVAGYLWDRTSGEEKHAGELTNVLSDVNVTNGNAITGYHYTGMKVANTFSSKA
1051  NRVFNVTLEKDEVVSKESFEERGTMLDASQIVSKKAEINPLTLPTVEPLSTSGKKDSDFSKIAHYQANRA
1121  LVYKNIEKLLPFYNKSTIVKYGNLVKENSLLYQKELLSAVMMKDDQVITDIVSNKQTANKLLLHYNDHSS
1191  EKFDLKYQTDFANLPEYNLGNTGLLYTPNQFLYDRDSIVKEVLPELQKLDYQSDAIRKTLGISPEVKLTE
1261  LYLEDQFSKTKQNLGDSLKKLLSADAGLASDNSVTRGYLVDKIKNNKEALLLGLTYLERWYNFNYGQVNV
1331  KDLVMYHPDFFGKGNTSPLDTLIELGKSGFNNLLAKNNVDTYGISLASQHGATDLFSTLEHYRKVFLPNT
1401  SNNDWFKSETKAYIVEEKSTIEEVKTKQGLAGTKYSIGVYDRITSATWKYRNMVLPLLTLPERSVFVIST
1471  MSSLGFGAYDRYRSSDHKAGKALNDFVEENARETAKRQRDHYDYWYRILVNSQRRKTLFVRFSLYDAYKF
```

Fig. 5B

1541 GDDTTSGKATAEAKFDSSNPAMKNFFGPVGNKVVHNQHGAYATGDGVYYMSYRMLDKDGA
1601 INY|THEMTH|DSDQDIYLGGYGRRNGLGP|E|FFAKGLLQAPDQPSDATITINFILKHSKSDSTEGSRLQVLD
1671 PTERFQNAADFQNYVHNMFDLIYMMEYLEGQSIVNKLSVYQKMAALRKIENKYVKDPADGNEVYATNVVK
1761 ELTEAEARNLNSFESLIDHNILSAREYQSGDYERNGYYTIKLFAPIYSALSSEKGTPGDLMGRRIAYELL
1811 AAKGFKDGMVPYISNQYEEDAKQQGQTINLYGKERGLVTDELVLKKVFDGKYKTWAEFKTAMYQERWISL
1881 GNLKQVTFKDPTKPWPSYGTKTINNVDELQALMDQAVLKDAEGPRWSNYDPEIDSAVHKLKRAIFKAYLD
1951 QTNDFRSSIFENKK

Fig. 5C

```
  1 MEKYFGEKQERFSFRKLSVGLVSATISSLFFMSVLASSSVDAQETAGVHY   50
    |.|::|||.||.||||.|||||||.|.|||||.|||:::|.|||.:|||
  1 MKKFLGEKQTRFAFRKLAVGLVSAAISSLFFVSIVGVDSVQAQEKLNVHY   50

51 KYVADSELSSEEKKQLVYDIPTYVENDDETYYLVLVYKLNSQNQLAELPNTG  100
    |||.||.|.:.||:|||||.||::.|..:|||||||.|||.||.||||||
 51 KYVTDTEITPQEKELIVSGVPRMPEGNEETYYLVRLNSNAGAKTLPNTG   100

101 SKNERQALVAGASLAALGILIFAVSKKKVKNKTVLHLVLVAGMGNGVLVS  150
    ..|:.||||.|||:||:|.|:|||.|:|:||.||.:|:|:||||:.|:|
101 DNNSNTMMAAGLLLTTIGLVVFAVSKRKVQSKFLLTVLVGASVGGGLILS  150

151 VHALENHLLLNYNTDYELTSGEKLPLPKEISGYTYIGYIKEGKTTSDFEV  200
    |.||||.:|.|:.|:|:||:.|.:|||||||||.|||||:|:||
151 VDALENGSLLQYNAEYQVSAGESLPSPGEISGYTYVGYIKDESIKKLLD.  199

201 SNQEKSAATPTKQQKVDYNVTPNFVDHPSTVQAIQEQTPVSSTKPTEVQV  250
    .|.||..::|:..
200 ............NKIPDNQQNANVD.........................  212
```

Fig. 6A

```
251 VEKPFSTELINPRKEEKQSSDSQEQLAEHKNLETKKE.EKISPKEKT.GV 298
        .|..:|.:.                      .|..:|.:..|..:|::.|::.|
213 ..............................KEALNQNKKLDYSVSFDKNGLKNQTVGV 240

299 NTLNPQDEVLSGQLNKPELLYREETIETKIDFQEEIQENPDLAEGTVRVK 348
    ||.:::|||||||.::|||||||.::|||||||||||||||||||||||
241 NTIEPQDEVLSGRVAKPELLYKETSIETEIAYGEQIQENPDLAEGTVRVK 290

349 QEGKLGKKVEIVRIFSVNKEEVSREIVSTSTTAPSPRIVEKGTKKTQVIK 398
    ||||.|||:|:|||||.:.:|||.:|.:||||||||||||||||:|..
291 QEGKPGRKIEVVRIFTVDNAEVSREVLSTKIEEATPKIVEKGTKKLEAPS 340

399 EQPETG..........VEHKDVQSGAIVEPAIQPELPEAVVSDKGEPEV 437
    |.|.|           ::|||||||||||.:|||.:|||||||:|
341 EKPVTSNLVQPEQVASL..........PEY 380

438 QPTLPEAVVTDKGETEVQPESPDTVVSDKGEPEQVAPLPEYKGNIEQVKP 487
    .||:|.:|                    :||||||||||||.|.:.|
381 SGTLSGAIV...EPEQIEPEIGGVQSGAIVEPEQVTPLPEYTG........ 420
```

Fig. 6B

```
488  ETPVEKTKEQGPEKTEEVPVKPTEETPVNPNEGTTEGTSIQEAAENPVQPA  537
            |::|::::|:  |::||::|:  |:  |
421  .........................TQAGAVVSPEQVAPLPEYTGTQSGAIVEPAQVTPLP  456

538  EESTTNSEKVSPDTSSENTGEVSSNPSDSTTSVGESNKPEHNDSKNENSE  587
           |:::|: ::        .  |::  |:   |  .
457  EYTGVQSGAIV.........KPAQVTPLPEYTGTQSGAIVEP..........  489

588  KTVEEVPVNPNEGTVEGTSNQETEKPVQPAEETQTNSGKIANENTGEVSN  637
       :|::|: ::|::    |: |:    |  :    |::  |  .
490  ...EQVTPSPEYTGVQAGAIVEPEQVASLPEYTGSQAGAIVE..........  528

638  KPSDSKPPVEESNQPEKNGTATKPENSGNTTSENGQTEPEKKLELRNVSD  687
           ||::  |: ::  .  |:|||||:|  ||||||||
529  .PEQVEPPQEYTGNIEPAAPEAENPTEKAQEPKEQKQEPEKNIELRNVSD  577

688  IELYSQTNGTYRQHVSLDGIPENTDTYFVKVKSSAFKDVYIPVASITEEK  737
      :|||: :: |:||||||:|: | :::||||||||:|||:||::||::|:|:|
578  VELYSLADGKYKQHVSLDAIPSNQENYFVKVKSSKFKDVFLPISSIVDST  627
```

Fig. 6C

```
738  RNGQSVYKITAKAEKLQQELENKYVDNFSFYLDKKAKEENTNFTSFSNLV  787
     ::|.||||||||:|||.::||||||.||||||:||||..||||||||||
628  KDGQPVYKITASAEKLKQDVNNKYEDNFTFYLAKKAEREVTNFTSFSNLV  677

788  KAINQNPSGTYHLAASLNANEVELGPDERSYIKDTFTGRLIGEKDGKIYA  837
     :||.|.|.||:|||||||||||||||:|...|||||||:||.|:|||||
678  QAINNLNGTYYLAASLNANEVELENGASSYIKGRFTGKLFGSKDGKNYA  727

838  IYNLKKPLFENLSGATVEKLSLKNVAISGKNDIGSLANEATNGTKIKQVH  887
     |||||||||:|||||||||:||||||||||||||||||||.|||||.:|
728  IYNLKKPLFDTLSAATVENLTLKDVNISGKTDIGALANEANNATRINNVH  777

888  VDGVLAGERGVGGLLAKADQSSIAESSFKGRIVNTYETTDAYNIGGLVGH  937
     ||||||||||:|||:||||:||:|:|||||||||:|||:|||||||||:
778  VDGVLAGERGIGGLVWKADNSKISNSSFKGRIVNSYETKAPYNIGGLVGQ  827

938  LTGKNASIAKSKATVTISSNTNRSDQTVGGLAGLVDQDAHIQNSYAEGDI  987
     ||||||:||||||||:|||||||:|:|||||||||||||:|||||||:|
828  LTGINALVDKSKATITISSNADSTNQTVGGLAGLVEKDALISNSYAEGNI  877
```

Fig. 6D

```
 988 NNVKHFGKVAGVAGYLWDRTSGEEKHAGELTNVLSDVNVTNGNAITGYHY 1037
     ||:| ||:|||||||||||||:||·||:||  ||||||:||·||||||
 878 NNVKRFGSVAGVAGYLWDRDSSEERHAGRLHNVLSDINVMNGNAISGYHY  927

1038 TGMKVANTFSSKANRVFNVTLEKDEVVSKESFEERGTMLDASQIVSKKAE 1087
     ||::::·||·|·|||·|:|||||||·||||·||||·||·||||·|·||
 928 RGMRITDSYSNKDNRVYKVTLEKDEVVTKESLEERGTILDVSQIASKKSE  977

1088 INPLTLPTVEPLSTSGKKDSDFSKIAHYQANRALVYKNIEKLLPFYNKST 1137
     ||·|·|·|·|·||·|·||:||·||||||·||:||||||·||·||||||·
 978 INSLSAPKVETLLTSTNKESDFSKVKDYQASRALAYKNIEKLLPFYNKAT 1027

1138 IVKYGNLVKENSLLYQKELLSAVMMKDDQVITDIVSNKQTANKLLLHYND 1187
     ||||||||||:||||·||·|||||||||||·|·|||||·||·|||||||
1028 IVKYGNLVKEDSTLYEKEILSAVMMKDNEVITDIASHKEAANKLLIHYKD 1077

1188 HSSEKFDLKYQTDFANLPEYNLGNTGLLYTPNQFLYDRDSIVKEVLPELQ 1237
     ||||||·||||:||||·|||·|||||||||·||||·||:||·|||||||·
1078 HSSEKLDLTYQSDFSKLAEYRVGDTGLIYTPNQFLQNHSSIVNEVLPDLK 1127

Fig. 6E
```

```
1238  KLDYQSDAIRKTLGISPEVKLTELYLEDQFSKTKQNLGDSLKKLLSADAG  1287
      :|||||:|||.|||..:|.:|||||:||..||:|||:||||:..|.||||
1128  AVDYQSEAIRNTLGISSGVSLTELYLEEQFAKTKENLANTLEKLLSADAV  1177

1288  LASDNSVTRGYLVDKIKNNKEALLLGLTYLERWYNFNYGQVNVKDLVMYH  1337
      :|||.|||:|||||||||:|||||||||||||||||||||||||||||||
1178  IASENQTINGYVVDKIKRNKEALLLGLTYLERWYNFNYGDVNVKDLVMYH  1227

1338  PDFFFGKNTSPLDTLIELGKSGFNNLLAKNNVDTYGISLASQHGATDLFS  1387
      ||||||||:|||||:|||||||||||||:|||..:.:||||||||||||
1228  MDFFFGKNVSPLDTIIELGKSGFNNLLAKNNVDAYNISLANNNATKDLFS  1277

1388  TLEHYRKVFLPNTSNNDWFKSETKAYIVEEKSTIEEVKTKQGLAGTKYSI  1437
      ||.|:||:|||||:|||||||:||||||||||:||.||:||:||||||||
1278  TLANYREVFLPNKTNNQWFKEQTKAYIVEEKSAIDEVRKQEQAGSKYSI  1327

1438  GVYDRITSATWKYRNMVLPLLTLPERSVFVISTMSSLGFAYDRYRSSDH  1487
      ||||||||:|||||||||||||||||||||||||||||||||||||...:|
1328  GVYDRITSDTWKYRNMVLPLLTMPERSVFVISTISSLGFAYDRYRNNEH  1377
```

Fig. 6F

```
1488  KAGKALNDFVEENARETAKRQRDHYDYWYRILVNSQRRKTLFVRFSLYDA  1537
      :|| .||.|||.||.:||..:|.|.|:.||:..:|..|:..::..:.:|||
1378  RAGAELNKFVEDNAQETAKRQRDHYDYWYRIL.DEQGREKLYRNILVYDA  1426

1538  YKFGDDTTSGKATAEAKFDSSNPAMKNFFGPVGNKVVHNQHGAYATGDGV  1587
      ||||||||:.||:||:||||||||||:|||||||||||||:|||||||:|
1427  YKFGDDTTVDKATVEAQFDSSNPAMKYFFGPVGNKVVHNKHGAYATGDSV  1476

1588  YYMSYRMLDKDGAINYTHEMTHDSDQDIYLGGYGRRNGLGPEFFAKGLLQ  1637
      |||.|||||||||:|||||||||||:.|||||||||.||||||||||||
1477  YYMGYRMLDKDGAITYTHEMTHDSDNEIYLGGYGRRSGLGPEFFAKGLLQ  1526

1638  APDQPSDATITINFILKHSKSDSTEGSRLQVLDPTERFQNAADFQNYVHN  1687
      |||.|.||||||:|.||||:...|:|||||||||||:|||||..||||||
1527  APDHPDDATITVNSILKYDKNDASEKSRLQVLDPTKRFQNADDLKNYVHN  1576

1688  MFDLIYMMEYLEGQSIVNKLSVYQKMAALRKIENKYVKDPADGNEVYATN  1737
      |||:|||:|||||.|||||||:|||:||||||||||||||:|||:|||||
1577  MFDVIYMLEYLEGMSIVNRLSDVQKVNALRKIENKYVRD.ADGNDVYATN  1625
```

Fig. 6G

```
1738  VVKELTEAEARNLNSFESLIDHNILSAREYQSGDYERNGYYTIKLFAPIY  1787
      |:::|:|..|||||||:..||||||||||:|||||:||||||.|||
1626  VIKNITMADAQKLNSFNSLIENDILSAREYKNGDVERNGYHTIKLFSPIY  1675

1788  SALSSEKGTPGDLMGRRIAYELLAAKGFKDGMVPYISNQYEEDAKQQGQT  1837
      |||||||||||||||||||||||||||||||||||||||||||:|.|.|
1676  SALSSEKGTPGDLMGRRIAYELLAAKGFKDGMVPYISNQYEDDAKQNGKT  1725

1838  INLYGKERGLVTDELVLKKVFDGKYKTWAEFKTAMYQERWISLGNLKQVT  1887
      |.:.|||||||||:|||:||..:|||.|||..|||||:|||..:.:.||
1726  ISIYGKTRGLVTDDLVLRKVFNGQFNNWTEFKKAMYEERKNKFDSLNKVT  1775

1888  FKDPTKPWPSYGTKTINNVDELQALMDQAVLKDAEGPR..WSNYDPEIDS  1935
      |.|.|:|||||.||||.:|||:|:|:|||:|||:|:..::||||||:.|
1776  FDDTRQPWTSYATKTISTVEELQTLMDEAVLQDANDNWYSWSGYKPEYNS  1825

1936  AVHKLKRAI.......FKAYLDQTNDFRSSIFENKK  1964
      |||||||:..::|.:.|:||:..||||
1826  AVHKLKKQSSKLTSIRLKILENQSLKTRSDWFEQSN  1861
```

COMPOSITIONS AND METHODS FOR TREATMENT OF *STREPTOCOCCUS PNEUMONIAE* INFECTION

CROSS REFERENCE TO RELATED APPLICATIONS

This application claims priority under 35 U.S.C. §119(e) to U.S. Provisional Application Ser. No. 60/026,939, filed on Sep. 23, 1996.

GOVERNMENT SUPPORT

This invention was supported in part by a grant from the U.S. Government (Public Health Service Grant No. AI38446 and NIH NIDR DE 09677) and the U.S. Government may therefore have certain rights in the invention.

FIELD OF THE INVENTION

The field of the invention is bacterial enzymes as targets for antibiotic therapy and as bacterial vaccines.

BACKGROUND OF THE INVENTION

Streptococcus pneumoniae (*S. pneumoniae*) is a major cause of both acute bacterial pneumonia and acute purulent meningitis in humans. This organism efficiently colonizes the mucosal surface of the human nasopharynx, which colonization is the initial step in the pathogenesis of respiratory tract infection (Tuomanen et al., 1995, *New Engl. J. Med.* 332:1280–1284). *S. pneumoniae* is highly adapted to its human host since natural infection of other host species, even in the carrier state, is unusual. An important factor in the ability of this organism to establish a presence on mucosal surfaces is its effective evasion of local host defenses.

It is known that *S. pneumoniae* encodes a proteolytic enzyme which specifically cleaves the heavy chain of human immunoglobulin A1 (IgA1), the predominant class of immunoglobulin present on mucosal membranes (Kett et al., 1986, *J. Immunol.* 136:3631–3635; Kilian et al., 1979, *Infect. Immun.* 26:143–149; Male, 1979, *Infect. Immun.* 62:254–261). However, the gene encoding *S. pneumoniae* IgA1 protease has not been identified and the protein product has not been isolated or purified. IgA1 protease has been characterized in a number of bacteria including *Neisseria gonorrhoreae* (Pohlner et al., 1987, *Nature* (London) 325:458–462), *Neisseria meningitides* (Koomey et al., 1984, *Immun.* 43:101–107; Plaut et al., 1975, *Science* 190:1103–1105), *Haemophilus influenzae* (Bricker et al., 1983, *Proc. Natl. Acad. Sci. USA* 80:2681–2685; Poulsen et al., 1989, *Infect. Immun.* 57:3097–3105), *Bacteroides melanogenicus* (Mortensen et al., 1984, *Infect. Immun.* 45:550–557), and *Streptococcus sanguis* (Gilbert et al., 1988, *Infect. Immun.* 56:1961–1966; Gilbert et al., 1991, *Infect. Immun.* 59:7–17). Although each of these enzymes hydrolyses human IgA1, they represent several classes of enzymes having different catalytic activities (e.g., they comprise a serine protease, a thiol-activated protease and a metalloprotease) and have distinct cleavage sites within the heavy-chain hinge region of IgA1. The independent evolution of several distinct classes of enzymes with a similar biological function points to the importance of inactivation of IgA1 for the successful colonization of the mucosal surface by these pathogens.

There is a paucity of information on the nature of the IgA1 protease encoded by *S. pneumoniae*. A recent survey of 114 isolates of *S. pneumoniae* revealed that at least 94% of the isolates possessed the ability to hydrolyze human IgA1 (Lomholt et al., 1995, *Infect. Immun.* 63:4238–4243). Similar to the situation in *S. sanguis* and *S. mitior*, *S. pneumoniae* cleaves a single peptide bond between $Pro_{227}$ and $Thr_{228}$, in the heavy chain of both human and great ape IgA1, the only known substrates for this enzyme (Gilbert et al., 1988, supra; Qiu et al., 1996, *Infect. Immun.* 64:933–937). *S. pneumoniae* IgA1 protease exhibits marked antigenic variation, in that at least seventeen antigenic forms have been identified (Lomholt et al., 1995, supra).

Treatment of infection by *S. pneumoniae* generally involves administration of the antibiotic penicillin since the great majority of *S. pneumoniae* are fully sensitive to it. However, given the recent emergence of penicillin-resistant and mulitdrug-resistant strains of *S. pneumoniae*, other antibiotics such as erythromycin are also prescribed (Klugman, 1990, *Clin. Microbiol. Rev.* 3:171–196). The fact that strains of this organism have evolved which are resistant to antibiotic therapy accentuates the need for prevention by vaccination of *S. pneumoniae*-induced disease, for the identification of new antibiotic targets in *S. pneumoniae*, and for the development of antibiotics directed against those targets which are capable of inhibiting the growth and/or pathogenesis of *S. pneumoniae* in the human host.

SUMMARY OF THE INVENTION

The invention relates to an isolated nucleic acid encoding *Streptococcus pneumoniae* IgA protease, or a biologically active fragment thereof.

In one aspect of the invention, the isolated nucleic acid of the invention encodes an IgA protease selected from the group consisting of IgA1 protease and IgA2 protease. In another aspect, the isolated nucleic acid of the invention encodes an IgA1 protease.

In one embodiment, the isolated nucleic acid of the invention is *Streptococcus pneumoniae* nucleic acid and preferably, it is *Streptococcus pneumoniae* strain P110 nucleic acid.

In another embodiment, the isolated nucleic acid of the invention is SEQ ID NO:1.

The invention also relates to a cell comprising an isolated nucleic acid encoding *Streptococcus pneumoniae* IgA protease, or a biologically active fragment thereof.

Also included in the invention is an isolated preparation of a polypeptide specifying *Streptococcus pneumoniae* IgA protease or a biologically active fragment thereof.

The isolated preparation of a polypeptide specifying *Streptococcus pneumoniae* IgA protease or a biologically active fragment thereof, is selected from the group consisting of IgA1 protease and IgA2 protease and preferably, it is IgA1 protease.

Preferably, the isolated preparation of the polypeptide of the invention is *Streptococcus pneumoniae* IgA1 protease and more preferably, it is *Streptococcus pneumoniae* strain P110 IgA1 protease.

In a preferred embodiment, the isolated preparation of the polypeptide of the invention is SEQ ID NO:3.

Also included in the invention is a cell comprising an isolated preparation of a polypeptide specifying *Streptococcus pneumoniae* IgA protease or a biologically active fragment thereof.

The invention further relates to a method of obtaining an isolated nucleic acid encoding a non-cell surface bacterial protein. The method comprises the steps of obtaining a DNA fragment from a library comprising bacterial DNA, introducing the DNA fragment into a sample of bacteria having a recognizable colony morphology in the absence of the DNA fragment, isolating bacteria comprising the DNA fragment, which bacteria have an altered colony morphology when compared with bacteria which do not comprise the DNA fragment, and, isolating the DNA fragment from the bacteria.

In a preferred embodiment of this method of the invention, the bacteria comprise Streptococcus. More preferably, the bacteria comprise *Streptococcus pneumoniae*, and even more preferably, the bacteria comprise *Streptococcus pneumoniae* strain P110.

In another embodiment of this method of the invention, the non-cell surface bacterial protein is an IgA protease.

Also included in the invention is a method of identifying a candidate antibiotic compound comprising the steps of providing a mixture comprising *Streptococcus pneumoniae* IgA protease, IgA protein and a buffer solution suitable for activity of the IgA protease, adding to an aliquot of the mixture a test compound, and measuring the level of IgA protease activity in the presence or absence of the test compound, wherein a lower level of IgA protease activity in the presence of the test compound, compared with the level of IgA protease activity in the absence of the test compound, is an indication that the test compound is a candidate antibiotic compound.

In one embodiment of this method of the invention, the *Streptococcus pneumoniae* IgA protease comprises *Streptococcus pneumoniae* cells or cell extracts. In another embodiment, the *Streptococcus pneumoniae* IgA protease comprises an isolated preparation of a polypeptide specifying *Streptococcus pneumoniae* IgA protease.

The invention also includes a candidate antibiotic compound obtained by a method comprising the steps of providing a mixture comprising *Streptococcus pneumoniae* IgA protease, IgA protein and a buffer solution suitable for activity of the IgA protease, adding to an aliquot of the mixture a test compound, and measuring the level of IgA protease activity in the presence or absence of the test compound, wherein a lower level of IgA protease activity in the presence of the test compound compared with the level of IgA protease activity in the absence of the test compound, is an indication that the test compound is a candidate antibiotic compound.

The invention additionally relates to a subunit vaccine comprising an isolated preparation of a polypeptide specifying a *Streptococcus pneumoniae* IgA protease suspended in a pharmaceutically acceptable carrier.

BRIEF DESCRIPTION OF THE DRAWINGS

FIG. 1 is a diagram of a restriction map of a 3.15 kb fragment of DNA obtained from *S. pneumoniae* strain P110 cloned into the plasmid pMU1328 ($O_1$). This fragment confers altered colony morphology on *S. pneumoniae* strain R6x. Plasmids in which portions of the insert were deleted were also tested for their ability to change (+) or not change (−) colony morphology when transformed into *S. pneumoniae* strain R6x. The DNA fragments which were deleted from the 3.15 kb region are indicated below the restriction map by the single lines. Restriction endonucleases: EcoRI, E; KpnI, K; NheI, Nh; NruI, Nr; SalI, S; and XbaI, X.

Restriction endonucleases: BamHI, B; EcoRI, E; HindIII, H; KpnI, K; NheI, Nh; NruI, Nr; SalI, S; and XbaI, X.

FIGS. 4A–E, comprising FIGS. 4A–4P, is the nucleotide sequence [SEQ ID NO:1] of the iga gene of *S. pneumoniae*. The protein encoded by the nucleic acid of SEQ ID NO:1 has the amino sequence SEQ ID NO:2. This sequence has been submitted to GenBank (accession number U476787).

FIGS. 5A–B, comprising FIGS. 5A–5C, is the amino acid sequence (1964 amino acids; SEQ ID NO:3) of the IgA1 protease of *S. pneumoniae* strain P110, which amino acid sequence was deduced from the nucleotide sequence of the iga gene. A region near the N-terminus that resembles the C-terminal anchor for many other gram-positive surface proteins is shown divided into three contiguous components, LPNTGS motif (Box a), hydrophobic domain (underlined), and a lysine-rich charged sequence (Box b). An ATP/GTP binding consensus sequence is shown in Box c. The sequence in Box d and the downstream glutamic acid residue in Box e constitute a zinc-binding domain. A hydrophilic region having similarity to the multiple tandem repeats in the IgA1 protease of *S. sanguis* is shown (dashed Box) wherein each similar sequence is shown in Boxes 1 through 11.

FIGS. 6A–C, comprising FIGS. 6A–6H, depicts a comparison of the deduced amino acid sequences of the iga gene of *S. pneumoniae* strain P110 (above) [SEQ ID NO:3] and the IgA1 protease of *S. sanguis* (below) [SEQ ID NO:4]. The Bestfit program of the Genetics Computer Group package was used, and symbols ('), (:) and (.) represent degrees of similarity based on the Dayhoff PAM-250 matrix.

Figure 7:
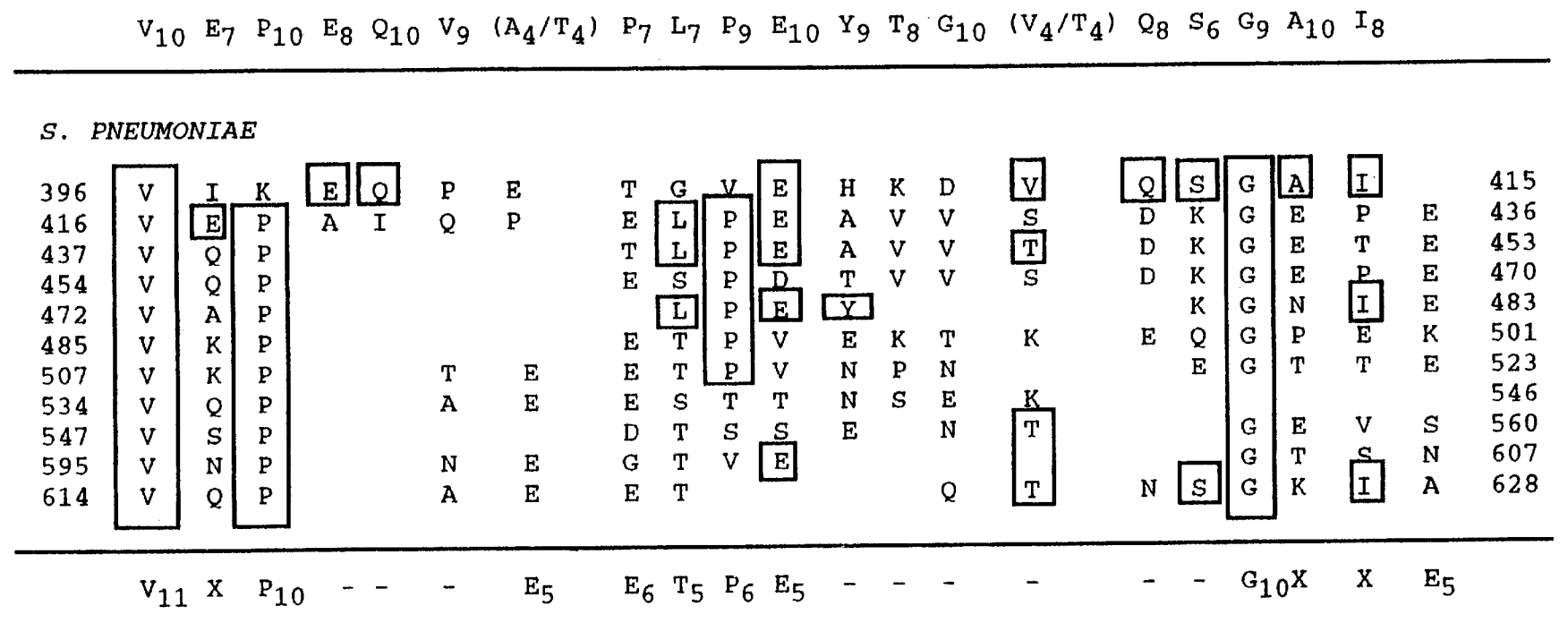

FIG. 7 is a comparison of regions of *S. pneumoniae* iga and *S. sanguis* repeat regions. The consensus sequence for the ten nearly identical tandem repeats of 20 amino acids in *S. sanguis* is shown above the top line. The frequency of occurrence of the most common amino acid in each position is indicated by the numbers in subscript. Eleven sequences in iga of *S. pneumoniae* positioned between amino acids 396 and 627 resembling the *S. sanguis* repeat region are listed below the *S. sanguis* sequence. The position of each sequence is shown to the left of the figure. Residues in *S. pneumoniae* iga which match the *S. sanguis* repeat region consensus are boxed. The most highly conserved amino acids in this region of *S. pneumoniae* are listed at the bottom of the figure and the frequency of the occurrence of these amino acids is indicated by the numbers in subscript.

Figure 8:
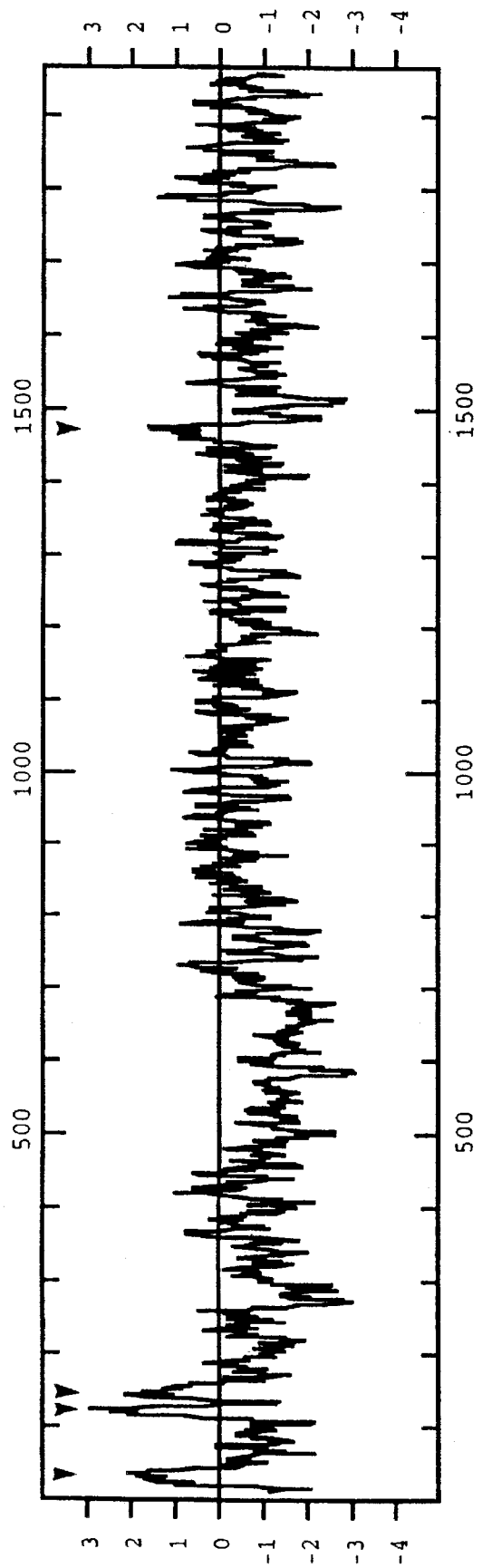

FIG. 8 is a graph depicting a Kyte-Doolittle hydropathy plot of the deduced 1964 amino acid sequence encoded by the iga gene of *S. pneumoniae*. Hydrophobic regions are above the line and the hydrophobic index is indicated on the y axis. Numbers on the x axis refer to the position in the open reading frame of iga beginning with the putative initiation codon. Four hydrophobic regions referred to in the text are indicated by arrow heads.

Figure 9:
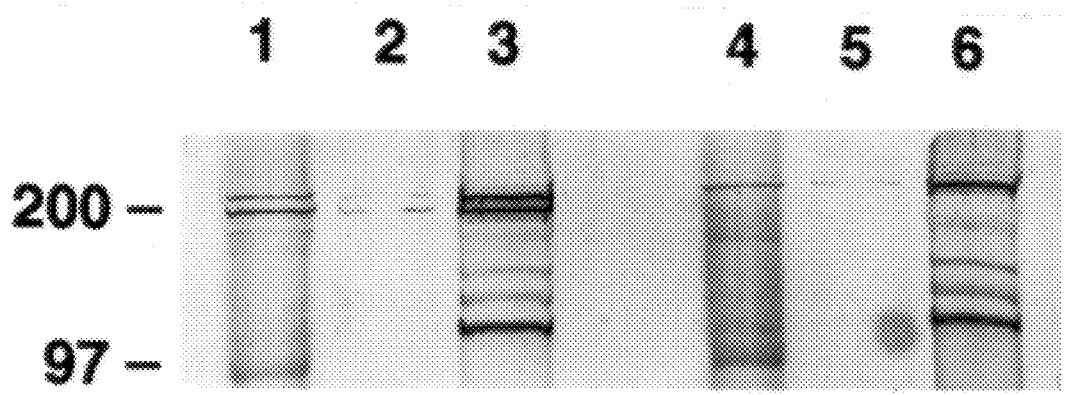

FIG. 9 is an image of a gel depicting Western blot analysis comparing high molecular weight proteins which react with an antiserum raised against whole S. pneumoniae cells. A band of approximately 200 kD (arrow) which appears in a whole cell lysate of the parent strain R6x (lane 1), was not detected in whole cell lysates obtained from the deletion/insertion mutant P262 (lane 4). The corresponding culture supernatant samples contained minimal amounts of this protein in the parent strain (R6x, lane 2) or the mutant strain (P262, lane 5). The 200 kD protein was apparent in a culture supernatant fraction obtained from the parent strain when it was concentrated 20-fold (R6x, lane 3) but was not present in culture supernatants obtained from the mutant P262, when such supernatants were similarly concentrated (lane 6). Molecular weight standards are in kilodaltons.

Figure 10:
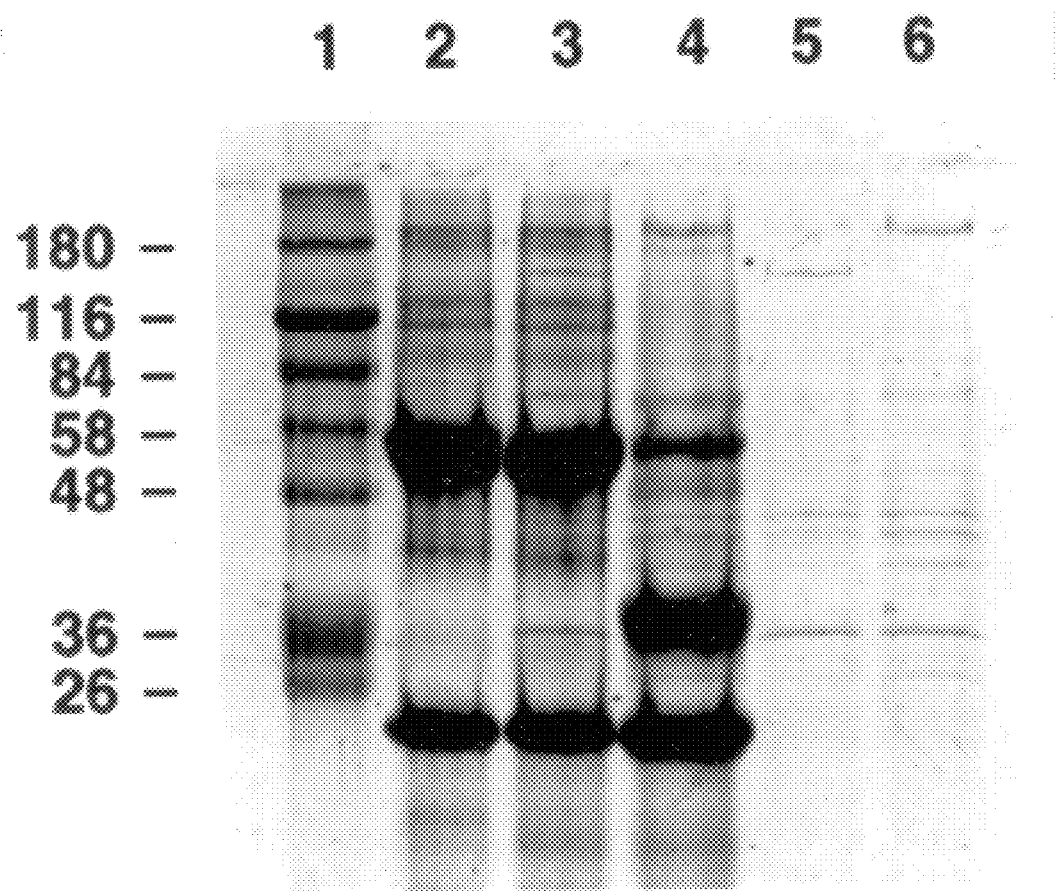

FIG. 10 is an image of a gel depicting IgA1 protease activity in culture supernatants obtained from the parent strain R6x, and the iga deletion/insertion mutant P262. Lane 1: molecular weight marker; lane 2: IgA1+buffer; lane 3: IgA1+P262 culture supernatant; lane 4: IgA1+R6x culture supernatant; lane 5: P262 culture supernatant; lane 6: R6x culture supernatant. In lane 4, a band of approximately 36 kd comprises the Fc fragment of cleaved IgA1 while the Fd fragment (α chain section in the Fab product) comigrates with the light chains. Molecular weight standards are indicated in kilodaltons.

DETAILED DESCRIPTION OF THE INVENTION

According to the present invention, a gene encoding S. pneumoniae IgA1 protease has been identified, isolated and characterized. This gene was identified by an unusual method involving the screening of a genomic library for sequences mediating observable changes in colony morphology. The ability of cloned DNA to alter the optical properties of the cell has been used to isolate bacterial genes; however, this approach has heretofore been applied exclusively to genes which encode cell surface components that contribute to the colony identification of the S. pneumoniae IgA1 protease gene described in the present study demonstrates that genes encoding non-cell surface component products which on their face do not appear to contribute to colony morphology, may also be isolated by screening transformants for differences in colony characteristics.

By "non-cell surface component" product as used herein, is meant a bacterial gene product which is not normally associated with the cell surface, i.e., the capsule, of the bacterium.

The gene encoding S. pneumoniae IgA1 protease could not be easily identified using ordinary recombinant DNA technology combined with PCR technology and probes comprising nucleic acid sequence derived from known Streptococcus IgA1 protease genes since there appeared to be an absence of significant nucleic acid homology between the sequence encoding S. pneumoniae IgA1 protease and the sequence of other known Streptococcus IgA1 proteases.

While the gene encoding IgA1 protease of the present invention has been initially discovered in S. pneumoniae strain P110, an IgA protease gene obtained from any other S. pneumoniae strain is also included in the invention. Preferably, the nucleotide sequence comprising the gene encoding IgA1 protease of S. pneumoniae is about 50% homologous, more preferably about 70% homologous, even more preferably about 80% homologous and most preferably about 90% homologous to the gene encoding IgA1 protease in S. pneumoniae strain P110.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGCG5' share 50% homology.

The gene encoding S. pneumoniae IgA protease may be isolated as described herein by first generating a genomic DNA library of the strain from which the gene is to be isolated. Next, fragments of genomic DNA are cloned into a shuttle vector, transformed into a bacterium such as E. coli and then used to transform a strain of S. pneumoniae (e.g., strain R6x) wherein changes in colony morphology which are induced following transformation are apparent. Those DNA fragments found to induce changes in colony morphology are then selected for further study.

To determine if DNA fragments so selected actually encode an IgA protease, the nucleotide sequence of the DNA is obtained. The putative amino acid sequence encoded by the DNA is deduced and this sequence is then compared with the amino acid sequence of known IgA proteases. In addition, the gene encoding the putative IgA protease may be cloned into an expression vector and the expressed product may be assessed for its ability to cleave IgA in a simple enzyme assay such as the IgA1 protease assay which is described herein.

Alternatively, since, according to the present invention, the gene encoding IgA1 protease has been identified, isolated and characterized, any other S. pneumoniae gene which encodes an IgA protease may be isolated using recombinant DNA technology wherein probes derived from S. pneumoniae strain P110 are generated which comprise conserved nucleotide sequences in the IgA1 protease gene. These probes may be used to identify additional IgA protease genes in genomic DNA libraries obtained from other strains of S. pneumoniae using the polymerase chain reaction or other recombinant DNA methodology.

Thus, the invention should be construed to include all S. pneumoniae IgA proteases which, by definition, are capable of cleaving an IgA molecule. In humans, it known that there are two IgA molecules, termed IgA1 and IgA2. Sequence comparisons between IgA molecules in species other than humans, reveals two types of IgA in several species of mammals. However, the difference between IgA1 and IgA2 between species varies in that IgA2 from one species may in fact be more similar to IgA1 from another species (Qiu et al., supra). While an IgA protease from S. pneumoniae which cleaves human IgA1 protease is exemplified herein, the invention should be construed to include S. pneumoniae IgA proteases capable of cleaving either or both of human IgA1 or human IgA2, i.e., the invention should be construed to include IgA1 and IgA2 proteases from *S. pneumoniae*.

An "isolated nucleic acid", as used herein, refers to a nucleic acid sequence, segment, or fragment which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

The invention also includes an isolated preparation of an IgA1 protease encoded by *S. pneumoniae* strain P110 and other IgA proteases encoded by other strains of *S. pneumoniae*. Preferably, the amino acid sequence of the IgA protease of *S. pneumoniae* is about 70% homologous, more preferably about 80% homologous, even more preferably about 90% homologous and most preferably about 95% homologous to the amino acid sequence of IgA1 protease expressed by *S. pneumoniae* strain P110.

The isolated preparation of an IgA protease encoded by *S. pneumoniae* may be obtained by cloning and expressing the gene encoding *S. pneumoniae* IgA protease and isolating the protein so expressed using available technology in the art. IgA protease may be purified by following known procedures for protein purification, wherein an immunological, enzymatic or other assay is used to monitor purification at each stage in the procedure. For example, synthetic oligonucleotides may be inserted into a DNA fragment encoding IgA protease, which oligonucleotides specify a series of histidine residues. Protein expressed from the DNA therefore comprises a series of histidines which are useful for purification of the protein using nickel chromatography. Such technology is known in the art, and is described, for example, in Gilbert et al. (1995, *Infn. Immun.* 63:2682–2688) and in literature provided by Qiagen Corp.

As used herein, the term "isolated preparation of a polypeptide" describes a compound, e.g., a protein or polypeptide which has been separated from components which naturally accompany it. Typically, a compound is isolated when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

The present invention also provides for analogs of proteins or peptides encoded by *S. pneumoniae* iga. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In addition to substantially full length polypeptides, the present invention provides for enzymatically active fragments of the polypeptides.

A *S. pneumoniae* IgA1-specific polypeptide is "enzymatically active" if it cleaves IgA1 in substantially the same manner as the naturally encoded protein in the assays described below.

As used herein, the term "fragment," as applied to a polypeptide, will ordinarily be at least about twenty contiguous amino acids, typically at least about fifty contiguous amino acids, more typically at least about seventy continuous amino acids, usually at least about one hundred contiguous amino acids, preferably at least about five hundred continuous amino acids, more preferably at least about one thousand contiguous amino acids, and most preferably at least about one thousand two hundred to about one thousand nine hundred or more contiguous amino acids in length.

The invention further includes a method of identifying a compound having antibiotic activity against *S. pneumoniae* by screening a test compound for the ability to affect the expression or activity of *S. pneumoniae* IgA protease.

Compounds which are identified using the methods of the invention are candidate antibiotic compounds for treatment of infections in humans caused by *S. pneumoniae*.

By "antibiotic activity" as used herein, is meant a compound which is capable of destroying or inhibiting the growth of bacteria or which is capable of inhibiting the pathogenesis, i.e., the disease-causing capacity, of a microorganism.

In each of the assays described, control experiments may include the use of mutant strains of *S. pneumoniae* which do not encode IgA protease. Such strains are generated by disruption of the IgA protease gene, generally in vitro, followed by recombination of the disrupted gene into the genome of *S. pneumoniae* using technology which is available in the art of recombinant DNA technology as applied to the generation of bacterial mutants and which is described herein.

In one aspect of the method of the invention, a compound is assessed for antibiotic activity by assessing the effect of the compound on *S. pneumoniae* IgA protease activity. In this instance, the test compound is added to an assay mixture designed to measure IgA protease activity. The assay mixture may comprise a mixture of cells which express *S. pneumoniae* IgA1 protease, IgA protein, a buffer solution suitable for optimal activity of IgA protease and the test compound. Controls may include the assay mixture without the test compound and the assay mixture having the test compound but without IgA protease. The mixture is incubated for a selected length of time and temperature suitable for cleavage of IgA as described herein, whereupon the reaction is stopped and the presence or absence of IgA cleavage products is assessed also as described herein.

Alternatively, the assay mixture may comprise a substantially pure preparation of *S. pneumoniae* IgA protease, IgA, a buffer and the test compound. Incubation of the assay mixture and cleavage of IgA is assessed as described herein.

Compounds which inhibit IgA protease activity are easily identified in the assay by assessing the degree of cleavage of IgA in the presence or absence of the test compound. A lower level, or minimal amounts of IgA cleavage products in the presence of the test compound compared with the absence of the test compound in the assay mixture is an indication that the test compound inhibits IgA protease activity.

The method of the invention is not limited by the type of test compound which may be used in the assay. The test compound may thus be a synthetic or naturally occurring molecule which may comprise a peptide or peptide-like molecule, or it may be any other molecule, either small or large, which is suitable for testing in the assay. The test compound may also be an antibody directed against IgA1 protease, other IgA protease molecules, or even directed against fragments of IgA protease molecules.

Compounds which inhibit IgA protease activity in vitro may then be tested for antibiotic activity directed against *S. pneumoniae* in vivo in humans. The spectrum of illnesses caused by *S. pneumoniae* is a reflection of its ability to survive in various ecological niches in the human host. The organism resides in the nasopharynx, commonly without adverse effect on the host, but may spread locally to cause upper or lower respiratory tract infection. In some circumstances, *S. pneumoniae* cells may enter the blood stream from the nasopharynx via the cervical lymph nodes, leading to bacteremia and occasionally, infection of other organ systems (Weiser et al., 1994, *Infect. Immun.* 62:2582–2589).

Essentially, the compound is administered to the human by any one of the routes described herein, and the effect of the compound on infection by *S. pneumoniae* is assessed by clinical and symptomatic evaluation. Such assessment is well known to the practioner in the field of *S. pneumoniae* and other respiratory tract infections.

Compounds may also be assessed in an in vivo animal model. There are essentially two types of in vivo models in which a compound may be tested for antibiotic activity directed against *S. pneumoniae*. In the first model, colonization of the mucosal surface of the nasopharynx by *S. pneumoniae* in the presence or absence of the test compound is assessed. Since, as noted herein, the ability of *S. pneumoniae* to survive in the nasopharynx is derived at least in part from its ability to evade the host immune response, it is predicted that compounds which inhibit *S. pneumoniae* IgA protease will have an effect on *S. pneumoniae* colonization of the nasopharynx.

Measurement of colonization of the mucosal surface of the nasopharynx by *S. pneumoniae* may be conducted in an animal model essentially as described in Weiser et al. (1994, supra). However, since *S. pneumoniae* IgA protease is highly substrate specific being capable of cleaving only human or great ape IgA (Qiu et al., 1996, supra), initially, transgenic animals which encode human IgA are used to assess the effect of the test compound on colonization of the nasopharynx. Transgenic animals encoding and expressing human IgA are known in the art and are described, for example, in Tuallion et al. (1993, *Proc. Natl. Acad. Sci. USA* 90:3720; 1995, In: The Antibodies 1: Gordon and Breech).

To assess colonization, briefly, an amount of *S. pneumoniae*, generally about 10 µl of phosphate buffered saline (PBS)-washed mid log phase organisms adjusted to the desired density, is inoculated into the left anterior naris of the animal. Colony counts are performed to ensure that the inocula are of the desired density and phenotype. The nasopharynx is cultured for the presence of viable *S. pneumoniae* by the slow instillation of 20 to 40 µl of sterile PBS into the left naris and withdrawal of the initial 10 µl from the right naris. This procedure ensures that the fluid has passed through the nasopharynx. The quantity of organisms recovered is then assessed in a well known culture assay.

The effect of the test compound on colonization of the nasopharynx by *S. pneumoniae* is evaluated by comparing the degree of colonization of the nasopharynx in animals which have been administered the test compound with the degree of colonization in animals which have not been administered the test compound, wherein a lower degree of colonization in animals administered the test compound is an indication that the test compound inhibits colonization of the nasopharynx by *S. pneumoniae*.

The invasive capability of *S. pneumoniae* may also be measured in a transgenic animal model. Essentially, bacteria which have entered the blood stream following inoculation of the nasopharynx are detected by culturing the same in a sample of blood obtained from the animal. Again, the effect of the test compound on the invasive capacity of *S. pneumoniae* is assessed by comparing the number of organisms found in the blood stream in animals which have been administered the test compound with the number of organisms in the blood stream in animals which have not been administered the test compound, wherein a lower number of organisms in the blood stream of animals administered the test compound is an indication that the test compound has an effect on the invasive capacity of *S. pneumoniae*.

In a second in vivo model, the virulence of *S. pneumoniae* is assessed in transgenic animals as described in Berry et al. (1995, *Infect. Immun.* 63:1969–1974). Essentially, cultures of *S. pneumoniae* are diluted to a density of $2 \times 10^6$ colony forming units per ml, and volumes of 0.1 ml are injected intraperitoneally into groups of transgenic animals. The survival time of the animals is recorded and the differences in median survival time between groups may be analyzed by the Mann-Whitney U test (two-tailed). Differences in the overall survival rate between groups may be analyzed by the $x^2$ test (two tailed).

The effect of the test compound on the virulence of *S. pneumoniae* is assessed by comparing the survival rates of animals which have been administered the test compound with the survival rate of animals which have not been administered the test compound, wherein a higher survival rate of animals administered the test compound is an indication that the test compound has an effect on the virulence of *S. pneumoniae*.

To determine the effect of a test compound on colonization of the mucosal surface or on invasiveness and/or virulence of *S. pneumoniae*, the test compound is administered to the animals either prior to, at the time of, or after inoculation of the animals with *S. pneumoniae*. The test compound may be administered directly into the nasopharynx, or may be administered by any other route including any one of the traditional modes (e.g., orally, parenterally, transdermally or transmucosally), in a sustained release formulation using a biodegradable biopolymer, or by on-site delivery using micelles, gels and liposomes, or rectally (e.g., by suppository or enema). Precise formulations and dosages will depend on the nature of the test compound and may be determined using standard techniques, by a pharmacologist of ordinary skill in the art.

The compound may also be assessed in non-transgenic animals to determine whether it acts through inhibition of IgA protease activity in vivo, or whether it acts via another mechanism. To test the effect of the test compound on bacterial infection (colonization, invasiveness and or virulence), the procedures described above are followed using non-transgenic animals instead of transgenic animals.

A compound which is identified in any of the above assays as having antibiotic activity directed against $S.$ $pneumoniae$ may then be tested for antibiotic activity directed against a variety of other organisms, particularly those organisms which are known to or are suspected to encode and express an IgA protease. Thus, any compound which is identified as an anti-$S.$ $pneumoniae$ antibiotic may not only be useful for treatment of infections caused by $S.$ $pneumoniae$, but may also be useful for treatment of infections caused by a variety of other bacteria and even other non-bacterial microorganisms, such as fungi and the like.

The $S.$ $pneumoniae$ IgA protease of the invention is also useful as a subunit vaccine which can be administered to a human patient at risk for infection by $S.$ $pneumoniae$. During infection with $S.$ $pneumoniae$, a host immune response is elicited which comprises primarily IgA. Since the function of the IgA protease of the invention is to inactivate host IgA thereby facilitating $S.$ $pneumoniae$ infection, anti-IgA protease antibody capable of inactivating IgA protease, serves as a suitable vaccine for protection of the patient against infection by $S.$ $pneumoniae$. Anti-IgA protease antibody may also be useful for treatment of an ongoing $S.$ $pneumoniae$ infection in that, it may serve to reduce the severity of the infection by causing inactivation of $S.$ $pneumoniae$ IgA protease.

A subunit vaccine comprising $S.$ $pneumoniae$ IgA protease comprises an isolated preparation of a polypeptide specifying $S.$ $pneumoniae$ IgA protease suspended in a pharmaceutically acceptable carrier. The isolated preparation of IgA protease is obtained following the procedures described herein. The vaccine may also comprise an adjuvant suitable for administration to a human and which adjuvant bolsters the immunogenicity and therefore the immunoprotective capacity of the vaccine.

To determine the efficacy of a subunit vaccine comprising $S.$ $pneumoniae$ IgA protease, a preparation of IgA protease suspended in a pharmaceutically acceptable carrier is administered to mice or other suitable animals, as described herein. The vaccine is administered to the animals intraperitoneally, intranasally or subcutaneously, using a suitable adjuvant, including, but not limited to, alum, Freund's complete or incomplete adjuvant, or cholera toxin B subunit, and the like. Both pre- and post-immune serum is obtained from the mice and the presence or absence of antibodies is determined in standard antibody assays, described, for example, in Harlow et al. (1988, In: Antibodies, a Laboratory Manual, Cold Spring Harbor, N.Y.).

The ability of anti-IgA protease antibodies to inactivate IgA protease and to affect infection by $S.$ $pneumoniae$ is determined in the in vitro and in vivo assays described herein. Mice are administered a range of concentrations of IgA protease from about 0.1 to about 500 µg per dose, using several different immunization schedules, e.g., weekly, biweekly, in order to determine the optimum conditions for effective immunization of the mice against $S.$ $pneumoniae$. Sera obtained from mice so immunized are tested for the ability to inactivate IgA protease in the in vitro assays described herein. The ability of an antibody to inactivate IgA protease in vitro is predictive of the in vivo protective activity of that antibody.

To assess whether antibody raised against IgA protease protects mice against in vivo challenge with $S.$ $pneumoniae$, immunized and non-immunized mice are administered various concentrations of $S.$ $pneumoniae$ by the routes described herein, at various times post-immunization when peak antibody levels are apparent. The number of immunized animals which survive challenge by $S.$ $pneumoniae$ is indicative of the efficacy of the IgA protease preparation as a vaccine candidate. Although these studies may be initially conducted using an intraperitoneal route, subsequent studies can involve all possible routes of administration including, but not limited to, intramuscular, subcutaneous and even oral routes of administration.

The IgA protease preparation is administered to a human either subcutaneously, intramuscularly, orally, intravenously, intradermally, intranasally or intravaginally, The complex is first suspended in a pharmaceutically acceptable carrier which is suitable for the chosen route of administration and which will be readily apparent to those skilled in the art of vaccine preparation and administration. The dose of vaccine to be used may vary dependent upon any number of factors including the age of the individual and the route of administration. Typically, the IgA protease preparation is administered in a range of 1 µg to 50 mg of protein per dose. Approximately 1–10 doses are administered to the individual at intervals ranging from once per week to once every few years.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Bacterial Strains, Growth Conditions and Media $S.$ $pneumoniae$ strains R6x and P110 are derived from strain R6 (Slauja et al., 1995, $Mol.$ $Microbiol.$ 16:215–227; Tiraby et al., 1973, $Proc.$ $Natl.$ $Acad.$ $Sci.$ $USA$ 70:3541–3545). $S.$ $pneumoniae$ cells were propagated in semisynthetic medium (C+Y medium, pH 8.0) at 37° C. without shaking (Lacks et al., 1960, $Biochim.$ $Biophys.$ $Acta.$ 39:508–517). Broth cultures were plated on tryptic soy plates containing 1% agar onto which 100 µl of catalase (5,000 U) (Worthington Biochemical Co., Freehold, N.J.) was added. Cultures were grown at 37° C. overnight in a candle extinction jar, which provided an atmosphere of increased $CO_2$ necessary for optimal growth of this organism on this medium. $E.$ $coli$ cells were propagated in Luria-Bertani broth with or without 1% agar. Colony morphology was assessed with a stereo-zoom microscope with oblique transmitted illumination as described (Weiser et al., 1994, supra). When required, antibiotics were added to the media at the following concentrations: kanamycin, 50 µg/ml; erythromycin, 500 µg/ml ($E.$ $coli$), 1 µg/ml ($S.$ $pneumoniae$).

Reagents and Antibodies

Restriction endonucleases and DNA modification enzymes were purchased from New England Biolabs, Beverly, Mass. [α-$^{32}$P]dCTP was obtained from Amersham, Arlington Heights, Ill. All chemicals were purchased from Sigma Chemical Co., St. Louis, Mo., unless otherwise stated. Polyclonal antiserum was raised in rabbits against formalin-killed whole S. pneumoniae strain P6, a serotype 9V clinical isolate. To obtain antiserum having a higher specificity for S. pneumoniae IgA1 protease, the antiserum was absorbed six times for 24 h at 4° C. with the iga mutant, P262.

Construction and Screening of a Genomic Library

S. pneumoniae genomic DNA was prepared by a published method (Pearce et al., 1993, Mol. Microbiol. 9:1037–1050). Chromosomal DNA obtained from S. pneumoniae strain P110 was partially digested with Sau3AI and was then size-fractionated on a 10–40% sucrose density gradient by centrifugation at 100,000×g for 22 hr (Sambrook et al., 1989, "Molecular Cloning: a Laboratory Manual" Cold Spring Harbor, N.Y.). The fractions containing DNA fragments ranging in size from 3–8 kb were pooled, ethanol precipitated, and used for ligation into BamHI digested shuttle plasmid, PMU1328 (Achen et al., 1986, Gene 45:45–49). The ligation mixture was then transformed into E. coli strain DH5α and selected on LB containing erythromycin (500 μg/ml). Competent R6x cells were transformed as described with DNA obtained from pooled plasmids (Lacks et al., 1960, supra). Erythromycin-resistant transformants were screened for the appearance of a colony morphology that differed from that of the R6x parent strain. Plasmids conferring altered colony morphology were extracted from S. pneumoniae along with genomic DNA and were transformed into E. coli for further analysis.

Recombinant DNA Methods

DNA sequencing was performed using the dideoxy chain termination method (Sanger et al., 1977, Proc. Natl. Acad. Sci. USA 74:5463–5467). Sequence analysis was carried out using the Genetics Computer Group software package obtained from the University of Wisconsin (Devereux et al., 1984, Nucl. Acids. Res. 12:387–395). Data bases were searched using the BLAST program through the National Center for Biotechnology Information (Altschul et al., 1990, J. Mol. Biol. 215:403–410). The 3' end of the iga gene of strain P110 was obtained by PCR. A fragment of the S. pneumoniae genome from an unrelated strain having IgA1 protease activity was also cloned and partially sequenced, including the 3' end of the gene. A primer 5'-TCCAAAGCGACAGTAACC-3' [SEQ ID NO:5] from within the sequence of the P110 iga gene, and a primer 5'-CTTGGTTTGTTCTTCATCAC-3', [SEQ ID NO:6] which is 3' to the termination codon on the opposite strand, were used to obtain a 3.3 kb PCR product from the P110 chromosome. The amplified product was cloned into the vector pCR™II (Invitrogen, San Diego, Calif.) according to the manufacturer's instructions. The sequence was then extended beyond the primer 3' to the termination codon by inverse PCR (Sambrook et al., 1989, supra).

Western Blotting

Equal amounts of bacterial cells (determined by measuring the optical density at $A_{620}$) were centrifuged and the resulting cell pellet was washed with PBS, pH 8.0, and resuspended in loading buffer at a volume which was 1/10th of the original culture volume. Loading buffer comprised Tris-HCl, (0.0625 M, pH 8.0), glycerol (10%), SDS (2%), 2-mercaptoethanol (5%) and bromophenol blue (0.00125%).

The culture supernatant was mixed with 5× loading dye consisting of glycerol (50%), SDS (15%), 2-mercaptoethanol (15%) and bromophenol blue (1.5%). A 20-fold concentrated culture supernatant was obtained by centrifugation in a Centriprep-50 (Amicon, Beverly, Mass.), which retains proteins greater than 50,000 daltons in size. The cell fraction and the corresponding amount of the supernatant fraction were heated to 100° C. for 5 minutes prior to separation by SDS-PAGE on 7.5% acrylamide separating gels. Electrotransfer of proteins onto Immobilon-P (Millipore Co., Bedford, Mass.), and Western blotting was carried out as described except that the membrane was immersed in methanol prior to wetting (Towbin et al., 1979, Proc. Natl. Acad. Sci. USA 76:4350–4354). Immunoblotting of membranes was carried out as follows. Membranes were first washed twice with Tris-saline blocking buffer (TSBB, 10 mM Tris-HCl, pH 8.0, 0.5 M NaCl, 0.5% Tween-20 and 0.02% sodium azide) and incubated for 16 hours with a 1 in 5000 dilution of antiserum. After five washes in TSBB, goat anti-rabbit immunoglobulin G antibody conjugated to alkaline phosphatase (Bio-Rad Laboratories, Hercules, Calif.) was added and the membrane was incubated for another 2 hours. Reactivity was visualized after an additional five washes with TSBB as described (Sambrook et al., supra).

Mutagenesis of the IgA1 Protease Gene

The ermC gene obtained from the plasmid pIM13, was isolated as ClaI-HindIII fragment and was cloned into ClaI-HindIII digested pBR322 (Monod et al., 1986, J. Bacteriol. 167:138–147). The resulting plasmid, pE169, served as a source of an erythromycin-resistance cassette. A 1.9 kb EcoRI fragment encompassing the 5' portion of the S. pneumoniae iga gene was cloned into the EcoRI site in the plasmid pHSG399 (Takeshita et al., 1987, Gene 61:63–74). An internal 777 bp NheI-NruI fragment within this EcoRI insert was deleted and the erythromycin-resistance cassette from pE169 which was digested with NheI and ScaI was inserted into the site of the deletion. The construct was linearized by digestion with BamHI, which cuts within the vector sequence, and was transformed into S. pneumoniae strain R6x. Successful transformants were selected on medium containing erythromycin. The deletion/insertion mutant in the R6x chromosome was designated P262.

Southern Hybridization

Interruption of the chromosomal gene in S. pneumoniae mutant P262 was confirmed by Southern hybridization. Electrophoretically separated chromosomal DNA from R6x and P262 was digested with EcoRI or HindIII and transferred bidirectionally to Hybond-N (Amersham, Arlington Heights, Ill.). Hybridization was conducted under high stringency conditions using as a probe an [α-$^{32}$P]-dCTP labeled EcoRI-XbaI fragment obtained from the S. pneumoniae iga, wherein radioactive labeling was accomplished by nick-translation.

Assay for IgA1 Protease Activity

Cultures of S. pneumoniae were grown overnight in Todd-Hewitt broth supplemented with 0.5% yeast extract (Difco Laboratories, Detroit, Mich.). Cells were removed by centrifugation and the clarified supernatants were subjected to 60% ammonium sulfate precipitation which resulted in 25-fold concentration of proteins contained therein. The salt was removed by thorough dialysis against Tris-HCl buffer (50 mM, pH 8.0).

IgA1 protease activity was assayed by incubating the dialyzed supernatant in the presence of a human IgA1 monoclonal immunoglobulin substrate in Tris buffer containing 20 mM $CaCl_2$ and 20 mM $MgCl_2$. After 3 hours of incubation at 37° C., the mixtures were subjected to SDS-PAGE on a 10% acrylamide separating gel. Protein bands were visualized on the gel by coomassie brilliant blue staining.

Identification of S. pneumoniae IgA1 Protease Gene

A genomic library of S. pneumoniae DNA in the streptococcal-E. coli shuttle plasmid, pMU1328, was screened for clones capable of affecting the colony morphology of S. pneumoniae. The source of DNA for the library, S. pneumoniae strain P110, is a spontaneous very transparent variant of strain R6 (Achen et al., 1986, supra; Slauja et al., 1995, supra).

In screening transformants of strain R6x to identify a genomic fragment conferring the very transparent phenotype of the donor DNA, transformants with an opaque phenotype were noted in addition to the expected transparent transformants. These opaque colonies differed from spontaneous opaque variants previously described because they appeared umbilicated as a result of autolysis (Slauja et al., 1995, supra; Weiser et al., 1996, Infect. Immun. 64:2240–2245). Several colonies obtained from different transformation experiments having this altered phenotype were chosen for further study. Genomic DNA was extracted from the transformants and was used to retransform R6x (backcross).

Plasmids capable of conferring the altered phenotype when transformed back into the recipient S. pneumoniae strain were then isolated for further analysis by transformation into E. coli. Restriction endonuclease mapping of four such plasmids indicated that the inserts were overlapping over a span of 3.1 kb.

Figure 2:
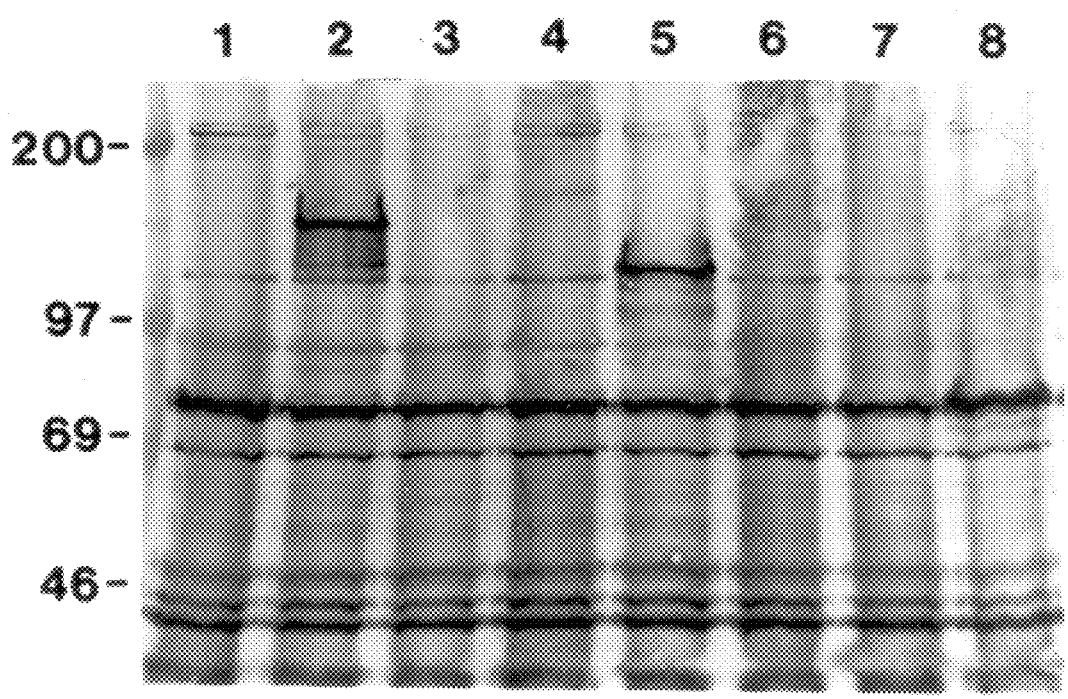
FIG. 2 is an image of a gel depicting Western blot analysis of whole cell lysates of *S. pneumoniae* strain R6x transformed with pMU1328 comprising various fragments of the 5' region of the gene, iga. An antiserum raised against heat-killed *S. pneumoniae* was used to detect proteins expressed by plasmids which were not present in the host strain. The restriction map of the plasmid constructs tested in lanes 2–8 are described in FIG. 1. Lane 1, R6x (host strain); lane 2, R6x/$O_1$; lane 3 R6x, pMU1328 (no insert); lane 4, R6x/$O_1\Delta E$; lane 5, R6x/$O_1\Delta S$; lane 6, R6x/$O_1\Delta K$; lane 7, R6x/$E_1$–$X_1$; and lane 8, R6x/$E_1$–$E_2$. Plasmids $O_1$, $O_1\Delta S$, and $E_1$–$E_2$ exhibit overexpression of a protein not seen in the host strain. Molecular weight standards are in kilodaltons (kD).

The region within this 3.1 kb that affected colony morphology was defined by testing a series of internal deletions within the plasmid insert for their ability to alter colony characteristics when transformed into R6x (FIG. 1). The minimum insert fragment capable of conferring altered colony morphology was a 1.9 kb fragment positioned at the 5' end of the 3.1 kb region. Altered colony morphology was associated with overexpression of a protein requiring this 5' region (FIG. 2).

Deletions involving the 5' end of the 3.1 kb insert resulted in a loss of the ability of the insert to confer altered colony morphology. The minimum fragment of 1.9 kb required for overexpression of this protein was sequenced (FIG. 2, lane 8). Analysis of this sequence revealed the 5' end of single long open reading frame of 1.6 kb encoding a putative N-terminus of 543 amino acids. This N-terminal fragment was extended to 964 amino acids by extending the sequence to the 3' end of the 3.1 kb insert. The 964 amino acid N-terminal sequence exhibited similarity (64% identity) with the N-terminal 854 amino acids of 1878 amino acids of the S. sanguis IgA1 protease (Gilbert et al., 1988, supra). This indicated that expression of an N-terminal 543 amino acids of this protein, the IgA1 protease encoded by S. pneumoniae, was sufficient to affect the colony morphology of strain R6x when expressed on the multicopy plasmid, pMU1328.

Cloning of the Complete IgA1 Protease Gene

Figure 3:
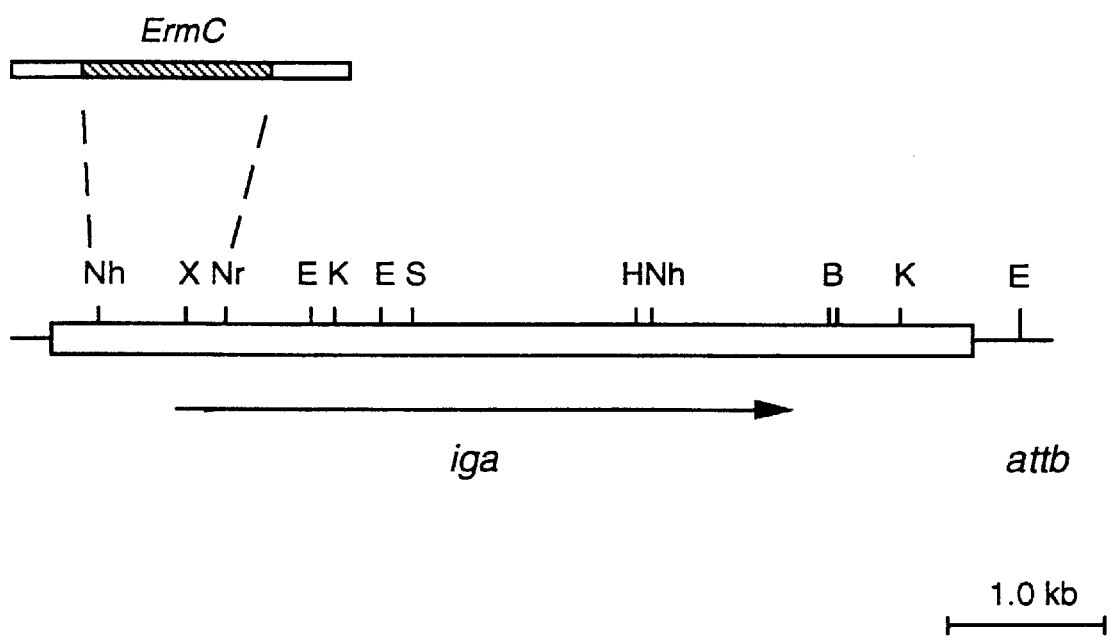
FIG. 3 is a diagram of a restriction map of a 6.4 kb region obtained from *S. pneumoniae* strain P110 which spans the entire iga gene (shown as an open box). The orientation of the gene is indicated by an arrow. Above the restriction map is the EcoRI fragment of the 5' end of the gene interrupted by insertion of the ermC gene. Mutagenesis of the chromosomal iga gene was carried out by transforming *S. pneumoniae* strain R6x with a construct having the ermC gene flanked by fragments of the iga gene.

The 3' end of the IgA1 protease gene of S. pneumoniae was cloned separately as follows. A DNA fragment encoding IgA1 protease activity was obtained from an unrelated S. pneumoniae strain and was cloned and partially sequenced. In order to clone the remainder of the gene from S. pneumoniae strain P110, a sequence from the 3' end of the gene from the other strain was used to construct a PCR primer to amplify P110 chromosomal DNA. The 3' end of the P110 iga gene on a 3.3 kb PCR fragment was cloned and sequenced. The overlapping nucleotide sequences of the two clones from strain P110 put together contained 6415 bp having a single open reading frame of 5891 bp (FIG. 3). This gene was designated iga based on the similarity of its deduced amino acid sequence to that of S. sanguis IgA1 protease. The sequence of S. pneumoniae iga is shown in FIGS. 4A–E, [SEQ ID NO:1].

Characteristics of the S. pneumoniae iga Gene

The S. pneumoniae iga gene contains an ATG codon near the 5' end of the open reading frame and located four base pairs from the sequence 5'-GGAGG-3' which could function as a ribosome binding site (Shine et al., 1974, Proc. Natl. Acad. Sci. USA 71:1342–1346). Beginning at this initiation codon, the open reading frame is predicted to encode 1964 amino acids FIGS. 5A–B [SEQ ID NO:3]. At the 3' end of the sequence, after the TAG termination codon, another 262 base pairs of nucleotide sequence were obtained by inverse PCR. This sequence overlaps the sequence adjacent to the unique attachment site for conjugative transposon Tn5252, indicating that this feature is 3' to the iga gene (Vijayakumar et al., 1993, J. Bacteriol. 175:2713–2719). The sequence following the iga gene did not contain inverted repeat sequences that resemble transcriptional terminators.

The entire 1964 amino acids of S. pneumoniae and the IgA1 protease of S. sanguis were compared FIGS. 6A–C [SEQ ID NOS: 3 and 4]. The deduced amino acid sequence of S. pneumoniae iga is 75% similar and 64% identical to the 1878 amino acid IgA1 protease of S. sanguis (Gilbert et al., 1991, supra). Only three regions in the S. pneumoniae sequence, from amino acids 193 to 292, 394 to 674, and the C-terminus from position 1942 exhibited less similarity to the sequence of S. sanguis IgA1 protease than the remaining regions. The first region of divergence, in which the S. pneumoniae sequence contains an additional approximately 60 residues, encompasses the N-terminus of the S. sanguis protein when expressed in E. coli (Gilbert et al., 1991, supra). The second region of divergence encompasses the region in S. sanguis which comprises ten nearly identical tandem repeats of a twenty-mer of unknown function. Although an exact copy of these repeats is not found in S. pneumoniae iga, the corresponding region contains 11 sequences matching as many as 10 of 20 amino acids in the S. sanguis consensus repetitive sequence (FIG. 7). A valine residue in position one, proline in position three and a glycine between positions 10 and 18 are particularly conserved among this region in S. pneumoniae protease.

The Kyte-Doolittle hydropathy plot of the amino acid sequence deduced from the entire open reading frame of the iga gene of S. pneumoniae demonstrated that the region containing this repetitive feature is hydrophilic compared to the remainder of the protein (FIG. 8) (Kyte et al., 1982, J. Mol. Biol. 157:105–132). There were three hydrophobic regions near the N-terminus, from amino acids 10 to 45, 103 to 125, and 133 to 162. The first hydrophobic region may function as a typical prokaryotic signal sequence (von Heijne, 1986, Nucl. Acids Res. 14:4683–4690). The second of the hydrophobic domains is located between the sequence L-P-N-T-G-S [SEQ ID NO:7] and a highly charged, lysine-rich region having the sequence K-K-K-V-K-N-K [SEQ ID NO:8]. The sequence L-P-N-T-G-S [SEQ ID NO:7] followed by a stretch of 24 hydrophobic residues and charged tail resembles the anchoring domain common to many Gram-positive surface proteins (Fischetti et al., 1990, *Mol. Microbiol.* 4:1603–1605, Schneewind et al., 1995, *Science* 268:103–106). This feature which is also found in the corresponding region in *S. sanguis*, occurs near the N-terminus rather than in its more typical location at the C-terminus. In addition, there is a single hydrophobic region in the remainder of the sequence from amino acid 1453 to 1473, which may serve as a transmembrane domain. The *S. pneumoniae* IgA1 protease has the sequence H-E-M-T-H [SEQ ID NO:9] at position 1605–1609 and has a highly conserved glutamic acid residue at 20 amino acids towards the carboxyl terminal from the histidine. A similar motif is found in *S. sanguis* IgA1 protease. This motif matches the internal zinc-binding consensus sequence (H-x-x-T-H) found in bacterial metalloproteases (Jongeneel et al., 1989, *FEBS Lett.* 242:196–203, Valle et al., 1990, *Proc. Natl. Acad. Sci. USA* 87:220–224). *S. pneumoniae* iga but not the *S. sanguis* gene, contains the sequence, G-Y-I-K-E-G-K-T [SEQ ID NO:10], from amino acid 187 to 194, which resembles the P-loop ATP/GTP-binding consensus sequence (GxxxxGKT) (Matti et al., 1990, *Trends Biochem. Sci.* 15:430–434). The deduced amino acid sequence of *S. pneumoniae* iga did not exhibit any significant homology with IgA1 proteases of bacterial species other than *S. sanguis*.

Mutagenesis of *S. pneumoniae* IgA1 Protease Gene

Mutagenesis was carried out on the *S. pneumoniae* iga gene to confirm that it is expressed and encodes an IgA1 protease. The *S. pneumoniae* iga gene was interrupted by replacing an internal 777 base pair NheI-NruI fragment located 234 base pairs 3' to the beginning of the open reading frame with a 1.2 kb erythromycin resistance cassette (ermC) (FIG. 3). The insertion was constructed on a plasmid which is unable to replicate in *S. pneumoniae*. The plasmid was linearized and transformed into *S. pneumoniae* strain R6x. Isolation of clones, wherein allelic exchange had occurred as a result of a cross-over event on both sides of the marker gene, was accomplished by selecting cells which were resistant to erythromycin. Interruption of the iga gene near its 5' end in the R6x chromosome was confirmed by Southern blot analysis using probes spanning the deleted fragment. The mutated gene was predicted to encode a truncated gene product comprising the first approximately 75 of the entire 1964 amino acids of the wild type protein. A single deletion/insertion mutant, P262, was selected for further analysis.

Western blot analysis of whole cell lysates was used to demonstrate that the iga gene on the *S. pneumoniae* chromosome is expressed (FIG. 9). Antiserum raised against whole cells reacted with an approximately 200 kD band in *S. pneumoniae* strain R6x. This is close to the predicted size of the gene product (219 kD) based on the deduced amino acid sequence. The mutant strain, P262, in which the iga gene was interrupted, did not express this protein, indicating that it represents the iga gene product. The specificity of the antiserum for this protein was further improved by serial absorption with P262.

The ability to detect the iga gene product using absorbed antiserum was used to assess whether the protein is exported from the cell as is the case for other known IgA1 proteases (Plaut et al., 1983, *Ann. Rev. Microbiol.* 37:603–622). Following growth to mid-log phase, cells and supernatants were separated from each other and were examined in Western blots. Although the 200 kD protein was identified in the supernatant fraction, the overwhelming majority of the protein remained cell associated. Concentration of proteins in the culture supernatant fraction confirmed that the iga gene product is present, albeit in low concentration in this fraction. The absence of the 200 kD protein in the concentrated culture supernatant obtained from P262 demonstrated that the absence of cell-associated protein in the mutant was not the result of altered secretion.

The ability of the iga gene product to hydrolyze its natural substrate, human IgA1, was assessed by comparing samples obtained from the deletion/insertion mutant and its parent strain (FIG. 10). Culture supernatant was incubated in the presence of human IgA1 monoclonal immunoglobulin substrate and hydrolysis of the IgA heavy chain was assessed by SDS-PAGE of any cleavage products. Interruption of the iga gene in P262 was associated with a complete loss of human IgA1 specific proteolytic activity in culture supernatants. This result confirmed the fact that the iga gene encodes an IgA1 protease and that this gene is responsible for the ability of the *S. pneumoniae* to cleave the heavy chain of human IgA1.

The iga gene was identified because of its effect on colony morphology when expressed on a multicopy plasmid in *S. pneumoniae* The colony morphology of P262 was compared to its parent strain to determine whether interruption of the chromosomal gene also affected colony morphology. There was no apparent difference in colony morphology between R6x and P262. This suggests that *S. pneumoniae* IgA1 protease is not a significant factor in the expression of varied colony phenotypes in this organism (Weiser et al., 1994, supra).

The experiments presented herein describe the identification, cloning and sequencing of a gene encoding *S. pneumoniae* cell-surface IgA1 protease. This gene was identified by an unusual method involving the screening of a genomic library for sequences mediating observable changes in colony morphology. Expression of a number of cell surface components can alter colony morphology (Weiser et al., 1996, supra). Colony morphology is a function of how visible light passing through a colony is affected by the packing of organisms within the colony.

Some cell-surface products may affect the ability of cells to associate in a colony and thereby contribute to the optical properties of the colony. The ability of cloned DNA to alter the optical properties of the cell has been used as a sensitive means of isolating a number of genes through the screening of individual transformants (Moxon et al., 1984, *J. Clin. Invest.* 73:298–306; Slauja et al., 1995, supra; Weiser et al., 1995, *Mol. Microbiol.* 17:555–564). However, this approach has been applied exclusively to genes which encode cell surface components that contribute to the colony phenotype. The identification of *S. pneumoniae* IgA1 protease gene described in this study demonstrates that genes encoding surface products which on their face do not appear to contribute to colony morphology, may also be isolated by screening transformants for differences in colony characteristics. In the study described herein, the colony morphology of strain R6x was modified by introduction of the 5' half of the IgA1 protease gene even though the chromosomal copy of this gene was shown to have no discernible effect on colony morphology.

Thus, a method of identifying genes has been discovered in the present invention which facilitates the identification of bacterial genes important for the pathogenesis of the organism, which genes may not be easily identified using ordinary recombinant DNA and PCR technology due the absence of apparent nucleic acid homology between the gene to be identified and known similar genes encoded by related organisms.

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A *Streptococcus pneumoniae* IgA protease or an enzymatically active fragment thereof in a composition wherein at least 90% (by dry weight) of the protein in said composition is said protease or fragment.

2. The IgA protease of claim 1, wherein at least 99% (by dry weight) of the protein in said composition is said protease or fragment.

3. The IgA protease of claim 1, wherein the amino acid sequence of said IgA is SEQ ID NO:3.

4. The IgA protease of claim 1, wherein said IgA protease is selected from the group consisting of IgA1 protease and IgA2 protease.

5. The IgA protease of claim 4, wherein said IgA protease is IgA1 protease.

6. A subunit vaccine comprising an isolated preparation of a *Streptococcus pneumoniae* IgA protease, or an enzymatically active fragment thereof, suspended in a pharmaceutically acceptable carrier, wherein at least 90% (by dry weight) of the protein in said isolated preparation is said protease or fragment.

7. The subunit vaccine of claim 6, wherein at least 99% (by dry weight) of the protein in said isolated preparation is said protease or fragment.

8. The subunit vaccine of claim 6, wherein said IgA protease is selected from the group consisting of IgA1 protease and IgA2 protease.

9. The subunit vaccine of claim 8, wherein said IgA protease is IgA1 protease.

10. The subunit vaccine of claim 6, wherein said IgA protease has the sequence of SEQ ID NO:3.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 6201 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 1..6201

(ix) FEATURE:
      (A) NAME/KEY: CDS
      (B) LOCATION: join(1..30, 34..39, 46..51, 55..99, 103..135,
          139..153, 157..165, 169..186, 190..210, 217..225,
          229..234, 238..6150, 6154..6177, 6181..6201)

(xi) SEQUENCE DESCRIPTION: SEQ ID NO:1:

```
GAA TTC TCC TCA ACT GCC TCA AAC CAT TTT TAG AAC GAT TAG TGA TAT        48
Glu Phe Ser Ser Thr Ala Ser Asn His Phe     Asn Asp         Tyr
 1               5                  10

GAG TAA CAC CTA CCG TGT AAA TTT CAT GGT AGG TGT TAT TGT ACC CCC        96
Glu     His Leu Pro Cys Lys Phe His Gly Arg Cys Tyr Cys Thr Pro
         15                  20                  25

AAA TAA TAT AAA ACA AAG TAT GAA AGC GCA TCT CAA TTT TAA GAC TTT       144
Lys     Tyr Lys Thr Lys Tyr Glu Ser Ala Ser Gln Phe     Asp Phe
         30                  35                  40

TTT GTA AAT TAA GAG TAT AAT TAA GGT ATA CTG CCT TTT CTA               186
Phe Val Asn     Glu Tyr Asn     Gly Ile Leu Pro Phe Leu
             45                      50

TAG ATA ATA GAT AAT ACA CTA ATA TAA TAA AGG TCT TTG TAA CAT ATA       234
    Ile Ile Asp Asn Thr Leu Ile         Arg Ser Leu     His Ile
     55                  60                              65

TAA ATT TTA TTT CAA GGA GGA ATA ATG GAA AAG TAT TTT GGT GAA AAA       282
    Ile Leu Phe Gln Gly Gly Ile Met Glu Lys Tyr Phe Gly Glu Lys
                 70                  75                  80

CAA GAG CGT TTT TCA TTT AGA AAA TTA TCA GTA GGA CTT GTA TCT GCA       330
Gln Glu Arg Phe Ser Phe Arg Lys Leu Ser Val Gly Leu Val Ser Ala
             85                  90                  95

ACG ATT TCA AGT TTA TTT TTT ATG TCT GTA TTA GCT AGT TCA TCT GTG       378
```

```
Thr Ile Ser Ser Leu Phe Phe Met Ser Val Leu Ala Ser Ser Val
        100                 105                 110

GAT GCT CAA GAA ACT GCG GGA GTT CAC TAT AAA TAT GTG GCA GAT TCA        426
Asp Ala Gln Glu Thr Ala Gly Val His Tyr Lys Tyr Val Ala Asp Ser
        115                 120                 125

GAG CTA TCA TCA GAA GAA AAG AAG CAG CTT GTC TAT GAT ATT CCG ACA        474
Glu Leu Ser Ser Glu Glu Lys Lys Gln Leu Val Tyr Asp Ile Pro Thr
130                 135                 140                 145

TAC GTG GAG AAT GAT GAT GAA ACT TAT TAT CTT GTT TAT AAG TTA AAT        522
Tyr Val Glu Asn Asp Asp Glu Thr Tyr Tyr Leu Val Tyr Lys Leu Asn
                150                 155                 160

TCT CAA AAT CAA CTG GCG GAA TTA CCA AAT ACT GGA AGC AAG AAT GAG        570
Ser Gln Asn Gln Leu Ala Glu Leu Pro Asn Thr Gly Ser Lys Asn Glu
        165                 170                 175

AGG CAA GCC CTA GTT GCT GGT GCT AGC TTA GCT GCT CTG GGA ATT TTA        618
Arg Gln Ala Leu Val Ala Gly Ala Ser Leu Ala Ala Leu Gly Ile Leu
        180                 185                 190

ATT TTT GCT GTT TCC AAG AAA AAG GTT AAG AAT AAA ACG GTA TTA CAT        666
Ile Phe Ala Val Ser Lys Lys Lys Val Lys Asn Lys Thr Val Leu His
195                 200                 205

TTA GTA TTG GTT GCG GGA ATG GGA AAT GGT GTC TTA GTT TCA GTC CAT        714
Leu Val Leu Val Ala Gly Met Gly Asn Gly Val Leu Val Ser Val His
210                 215                 220                 225

GCT TTA GAA AAT CAT CTT TTG CTA AAT TAC AAT ACG GAC TAT GAA TTG        762
Ala Leu Glu Asn His Leu Leu Leu Asn Tyr Asn Thr Asp Tyr Glu Leu
                230                 235                 240

ACC TCT GGA GAA AAA TTA CCT CTT CCT AAA GAG ATT TCA GGT TAC ACT        810
Thr Ser Gly Glu Lys Leu Pro Leu Pro Lys Glu Ile Ser Gly Tyr Thr
        245                 250                 255

TAT ATT GGA TAT ATC AAA GAG GGA AAA ACG ACT TCT GAT TTT GAA GTA        858
Tyr Ile Gly Tyr Ile Lys Glu Gly Lys Thr Thr Ser Asp Phe Glu Val
        260                 265                 270

AGT AAT CAA GAA AAA TCA GCA GCC ACT CCT ACA AAA CAA CAA AAG GTG        906
Ser Asn Gln Glu Lys Ser Ala Ala Thr Pro Thr Lys Gln Gln Lys Val
275                 280                 285

GAT TAT AAT GTT ACA CCA AAT TTT GTA GAC CAT CCA TCA ACA GTA CAA        954
Asp Tyr Asn Val Thr Pro Asn Phe Val Asp His Pro Ser Thr Val Gln
290                 295                 300                 305

GCT ATT CAG GAA CAA ACA CCT GTT TCT TCA ACT AAG CCG ACA GAA GTT       1002
Ala Ile Gln Glu Gln Thr Pro Val Ser Ser Thr Lys Pro Thr Glu Val
        310                 315                 320

CAA GTA GTT GAA AAA CCT TTC TCT ACT GAA TTA ATC AAT CCA AGA AAA       1050
Gln Val Val Glu Lys Pro Phe Ser Thr Glu Leu Ile Asn Pro Arg Lys
        325                 330                 335

GAA GAG AAA CAA TCT TCA GAT TCT CAA GAA CAA TTA GCC GAA CAT AAG       1098
Glu Glu Lys Gln Ser Ser Asp Ser Gln Glu Gln Leu Ala Glu His Lys
        340                 345                 350

AAT CTA GAA ACG AAG AAA GAG GAG AAG ATT TCT CCA AAA GAA AAG ACT       1146
Asn Leu Glu Thr Lys Lys Glu Glu Lys Ile Ser Pro Lys Glu Lys Thr
        355                 360                 365

GGG GTA AAT ACA TTA AAT CCA CAG GAT GAA GTT TTA TCA GGT CAA TTG       1194
Gly Val Asn Thr Leu Asn Pro Gln Asp Glu Val Leu Ser Gly Gln Leu
370                 375                 380                 385

AAC AAA CCT GAA CTC TTA TAT CGT GAG GAA ACT ATA GAG ACA AAA ATA       1242
Asn Lys Pro Glu Leu Leu Tyr Arg Glu Glu Thr Ile Glu Thr Lys Ile
                390                 395                 400

GAT TTT CAA GAA GAA ATT CAA GAA AAT CCT GAT TTA GCT GAA GGA ACT       1290
Asp Phe Gln Glu Glu Ile Gln Glu Asn Pro Asp Leu Ala Glu Gly Thr
        405                 410                 415

GTA AGA GTA AAA CAA GAA GGT AAA TTA GGT AAG AAA GTT GAA ATC GTC       1338
```

```
Val Arg Val Lys Gln Glu Gly Lys Leu Gly Lys Lys Val Glu Ile Val
        420                 425                 430

AGA ATA TTC TCT GTA AAC AAG GAA GAA GTT TCG CGA GAA ATT GTT TCA       1386
Arg Ile Phe Ser Val Asn Lys Glu Glu Val Ser Arg Glu Ile Val Ser
435                 440                 445

ACT TCA ACG ACT GCG CCT AGT CCA AGA ATA GTC GAA AAA GGT ACT AAA       1434
Thr Ser Thr Thr Ala Pro Ser Pro Arg Ile Val Glu Lys Gly Thr Lys
450                 455                 460                 465

AAA ACT CAA GTT ATA AAG GAA CAA CCT GAG ACT GGT GTA GAA CAT AAG       1482
Lys Thr Gln Val Ile Lys Glu Gln Pro Glu Thr Gly Val Glu His Lys
                470                 475                 480

GAC GTA CAG TCT GGA GCT ATT GTT GAA CCC GCA ATT CAG CCT GAG TTG       1530
Asp Val Gln Ser Gly Ala Ile Val Glu Pro Ala Ile Gln Pro Glu Leu
            485                 490                 495

CCC GAA GCT GTA GTA AGT GAT AAA GGC GAA CCA GAA GTT CAA CCG ACA       1578
Pro Glu Ala Val Val Ser Asp Lys Gly Glu Pro Glu Val Gln Pro Thr
        500                 505                 510

TTA CCC GAA GCA GTT GTG ACC GAC AAA GGT GAG ACT GAG GTT CAA CCA       1626
Leu Pro Glu Ala Val Val Thr Asp Lys Gly Glu Thr Glu Val Gln Pro
515                 520                 525

GAG TCG CCA GAT ACT GTG GTA AGT GAT AAA GGT GAA CCA GAG CAG GTA       1674
Glu Ser Pro Asp Thr Val Val Ser Asp Lys Gly Glu Pro Glu Gln Val
530                 535                 540                 545

GCC CCA TTG CCA GAA TAT AAG GGT AAT ATT GAG CAA GTA AAA CCT GAA       1722
Ala Pro Leu Pro Glu Tyr Lys Gly Asn Ile Glu Gln Val Lys Pro Glu
                550                 555                 560

ACT CCG GTT GAG AAG ACC AAA GAA CAA GGT CCA GAA AAA ACT GAA GAA       1770
Thr Pro Val Glu Lys Thr Lys Glu Gln Gly Pro Glu Lys Thr Glu Glu
            565                 570                 575

GTT CCA GTA AAA CCA ACA GAA GAA ACA CCA GTA AAT CCA AAT GAA GGT       1818
Val Pro Val Lys Pro Thr Glu Glu Thr Pro Val Asn Pro Asn Glu Gly
        580                 585                 590

ACT ACA GAA GGA ACC TCA ATT CAA GAA GCA GAA AAT CCA GTT CAA CCT       1866
Thr Thr Glu Gly Thr Ser Ile Gln Glu Ala Glu Asn Pro Val Gln Pro
595                 600                 605

GCA GAA GAA TCA ACA ACG AAT TCA GAG AAA GTA TCA CCA GAT ACA TCT       1914
Ala Glu Glu Ser Thr Thr Asn Ser Glu Lys Val Ser Pro Asp Thr Ser
610                 615                 620                 625

AGC GAA AAT ACT GGG GAA GTG TCC AGT AAT CCT AGT GAT TCG ACA ACC       1962
Ser Glu Asn Thr Gly Glu Val Ser Ser Asn Pro Ser Asp Ser Thr Thr
                630                 635                 640

TCA GTT GGA GAA TCA AAT AAA CCA GAA CAT AAT GAC TCT AAA AAT GAA       2010
Ser Val Gly Glu Ser Asn Lys Pro Glu His Asn Asp Ser Lys Asn Glu
            645                 650                 655

AAT TCA GAA AAA ACT GTA GAA GAA GTT CCA GTA AAT CCA AAT GAA GGC       2058
Asn Ser Glu Lys Thr Val Glu Glu Val Pro Val Asn Pro Asn Glu Gly
        660                 665                 670

ACA GTA GAA GGT ACC TCA AAT CAA GAA ACA GAA AAA CCA GTT CAA CCT       2106
Thr Val Glu Gly Thr Ser Asn Gln Glu Thr Glu Lys Pro Val Gln Pro
675                 680                 685

GCA GAA GAA ACA CAA ACA AAC TCT GGG AAA ATA GCT AAC GAA AAT ACT       2154
Ala Glu Glu Thr Gln Thr Asn Ser Gly Lys Ile Ala Asn Glu Asn Thr
690                 695                 700                 705

GGA GAA GTA TCC AAT AAA CCT AGT GAT TCA AAA CCA CCA GTT GAA GAA       2202
Gly Glu Val Ser Asn Lys Pro Ser Asp Ser Lys Pro Pro Val Glu Glu
                710                 715                 720

TCA AAT CAA CCA GAA AAA AAC GGA ACT GCA ACA AAA CCA GAA AAT TCA       2250
Ser Asn Gln Pro Glu Lys Asn Gly Thr Ala Thr Lys Pro Glu Asn Ser
            725                 730                 735

GGT AAT ACA ACA TCA GAG AAT GGA CAA ACA GAA CCA GAG AAA AAA CTC       2298
```

```
                Gly Asn Thr Thr Ser Glu Asn Gly Gln Thr Glu Pro Glu Lys Lys Leu
                                740                 745                 750

GAA TTA AGA AAT GTT TCT GAT ATT GAG TTG TAT AGT CAG ACG AAT GGA         2346
Glu Leu Arg Asn Val Ser Asp Ile Glu Leu Tyr Ser Gln Thr Asn Gly
755                 760                 765

ACC TAC AGA CAA CAT GTT TCA TTG GAT GGA ATT CCA GAG AAT ACG GAT         2394
Thr Tyr Arg Gln His Val Ser Leu Asp Gly Ile Pro Glu Asn Thr Asp
770                 775                 780                 785

ACT TAC TTT GTC AAG GTA AAA TCT TCA GCA TTT AAA GAT GTC TAT ATA         2442
Thr Tyr Phe Val Lys Val Lys Ser Ser Ala Phe Lys Asp Val Tyr Ile
                790                 795                 800

CCA GTA GCT TCA ATA ACC GAA GAG AAA AGA AAT GGG CAG TCA GTT TAT         2490
Pro Val Ala Ser Ile Thr Glu Glu Lys Arg Asn Gly Gln Ser Val Tyr
                805                 810                 815

AAA ATC ACA GCC AAA GCT GAG AAA CTC CAG CAA GAA CTA GAA AAT AAA         2538
Lys Ile Thr Ala Lys Ala Glu Lys Leu Gln Gln Glu Leu Glu Asn Lys
                820                 825                 830

TAT GTC GAC AAT TTC TCC TTC TAC CTC GAT AAG AAG GCT AAA GAG GAA         2586
Tyr Val Asp Asn Phe Ser Phe Tyr Leu Asp Lys Lys Ala Lys Glu Glu
835                 840                 845

AAT ACA AAC TTT ACT TCC TTT AGC AAC CTG GTC AAA GCT ATA AAC CAA         2634
Asn Thr Asn Phe Thr Ser Phe Ser Asn Leu Val Lys Ala Ile Asn Gln
850                 855                 860                 865

AAT CCC TCT GGA ACC TAT CAT TTA GCG GCC AGC CTG AAT GCT AAC GAA         2682
Asn Pro Ser Gly Thr Tyr His Leu Ala Ala Ser Leu Asn Ala Asn Glu
                870                 875                 880

GTG GAG CTT GGT CCT GAT GAA AGA TCC TAT ATC AAG GAC ACC TTT ACT         2730
Val Glu Leu Gly Pro Asp Glu Arg Ser Tyr Ile Lys Asp Thr Phe Thr
                885                 890                 895

GGT CGT TTA ATC GGT GAA AAA GAT GGC AAG ATT TAT GCT ATC TAT AAT         2778
Gly Arg Leu Ile Gly Glu Lys Asp Gly Lys Ile Tyr Ala Ile Tyr Asn
                900                 905                 910

TTG AAA AAA CCT CTG TTT GAA AAC TTG AGT GGT GCT ACA GTA GAA AAA         2826
Leu Lys Lys Pro Leu Phe Glu Asn Leu Ser Gly Ala Thr Val Glu Lys
915                 920                 925

CTG AGT CTA AAA AAT GTT GCT ATT TCA GGG AAA AAT GAT ATT GGT TCA         2874
Leu Ser Leu Lys Asn Val Ala Ile Ser Gly Lys Asn Asp Ile Gly Ser
930                 935                 940                 945

CTG GCA AAT GAA GCT ACG AAT GGC ACA AAG ATT AAA CAA GTT CAT GTT         2922
Leu Ala Asn Glu Ala Thr Asn Gly Thr Lys Ile Lys Gln Val His Val
                950                 955                 960

GAT GGT GTT CTG GCT GGA GAA CGT GGT GTC GGT GGT TTG TTG GCT AAG         2970
Asp Gly Val Leu Ala Gly Glu Arg Gly Val Gly Gly Leu Leu Ala Lys
                965                 970                 975

GCA GAC CAA TCA AGC ATC GCA GAG AGC AGT TTC AAG GGA AGA ATT GTC         3018
Ala Asp Gln Ser Ser Ile Ala Glu Ser Ser Phe Lys Gly Arg Ile Val
                980                 985                 990

AAT ACC TAT GAA ACG ACT GAT GCC TAC AAT ATT GGC GGT CTG GTC GGT         3066
Asn Thr Tyr Glu Thr Thr Asp Ala Tyr Asn Ile Gly Gly Leu Val Gly
995                 1000                1005

CAT TTA ACA GGA AAA AAT GCG TCT ATT GCT AAA TCC AAA GCG ACA GTA         3114
His Leu Thr Gly Lys Asn Ala Ser Ile Ala Lys Ser Lys Ala Thr Val
1010                1015                1020                1025

ACC ATT TCG TCA AAC ACC AAT AGG TCA GAT CAG ACT GTC GGT GGT CTT         3162
Thr Ile Ser Ser Asn Thr Asn Arg Ser Asp Gln Thr Val Gly Gly Leu
                1030                1035                1040

GCA GGT CTA GTA GAC CAA GAT GCG CAT ATA CAG AAC AGT TAT GCG GAA         3210
Ala Gly Leu Val Asp Gln Asp Ala His Ile Gln Asn Ser Tyr Ala Glu
                1045                1050                1055

GGT GAT ATT AAT AAT GTC AAG CAC TTT GGT AAA GTC GCT GGT GTG GCA         3258
```

-continued

```
Gly Asp Ile Asn Asn Val Lys His Phe Gly Lys Val Ala Gly Val Ala
            1060                1065                1070

GGA TAT TTG TGG GAT CGA ACT TCT GGT GAG GAA AAA CAC GCT GGT GAA     3306
Gly Tyr Leu Trp Asp Arg Thr Ser Gly Glu Glu Lys His Ala Gly Glu
        1075                1080                1085

TTG ACC AAT GTT CTT AGC GAT GTC AAT GTA ACA AAC GGA AAT GCC ATC     3354
Leu Thr Asn Val Leu Ser Asp Val Asn Val Thr Asn Gly Asn Ala Ile
1090                1095                1100                1105

ACT GGA TAC CAC TAT ACA GGA ATG AAG GTA GCT AAT ACA TTT AGT AGT     3402
Thr Gly Tyr His Tyr Thr Gly Met Lys Val Ala Asn Thr Phe Ser Ser
            1110                1115                1120

AAG GCT AAT AGA GTT TTC AAT GTC ACT TTA GAG AAG GAT GAG GTC GTC     3450
Lys Ala Asn Arg Val Phe Asn Val Thr Leu Glu Lys Asp Glu Val Val
        1125                1130                1135

AGC AAG GAA TCC TTT GAA GAA AGA GGA ACA ATG CTA GAT GCT TCT CAA     3498
Ser Lys Glu Ser Phe Glu Glu Arg Gly Thr Met Leu Asp Ala Ser Gln
            1140                1145                1150

ATT GTA AGC AAA AAA GCA GAA ATA AAT CCT CTC ACT CTA CCA ACG GTG     3546
Ile Val Ser Lys Lys Ala Glu Ile Asn Pro Leu Thr Leu Pro Thr Val
        1155                1160                1165

GAA CCC CTC TCA ACA AGT GGC AAG AAA GAC AGT GAT TTT TCT AAG ATA     3594
Glu Pro Leu Ser Thr Ser Gly Lys Lys Asp Ser Asp Phe Ser Lys Ile
1170                1175                1180                1185

GCC CAT TAT CAA GCT AAC CGT GCT TTG GTT TAT AAG AAC ATT GAA AAA     3642
Ala His Tyr Gln Ala Asn Arg Ala Leu Val Tyr Lys Asn Ile Glu Lys
            1190                1195                1200

TTG TTA CCT TTT TAT AAT AAG TCA ACC ATC GTC AAA TAC GGA AAC CTG     3690
Leu Leu Pro Phe Tyr Asn Lys Ser Thr Ile Val Lys Tyr Gly Asn Leu
        1205                1210                1215

GTT AAG GAG AAC AGT CTC TTA TAC CAA AAA GAA CTC TTA TCT GCA GTT     3738
Val Lys Glu Asn Ser Leu Leu Tyr Gln Lys Glu Leu Leu Ser Ala Val
        1220                1225                1230

ATG ATG AAG GAT GAC CAA GTA ATC ACA GAT ATT GTT TCC AAC AAA CAG     3786
Met Met Lys Asp Asp Gln Val Ile Thr Asp Ile Val Ser Asn Lys Gln
    1235                1240                1245

ACT GCA AAC AAA CTC TTA CTT CAC TAT AAT GAC CAT TCA TCT GAG AAA     3834
Thr Ala Asn Lys Leu Leu Leu His Tyr Asn Asp His Ser Ser Glu Lys
1250                1255                1260                1265

TTT GAT CTC AAG TAC CAG ACT GAT TTT GCC AAT CTA CCA GAA TAT AAT     3882
Phe Asp Leu Lys Tyr Gln Thr Asp Phe Ala Asn Leu Pro Glu Tyr Asn
            1270                1275                1280

CTA GGT AAT ACG GGA CTT CTC TAC ACT CCT AAC CAA TTC TTA TAT GAT     3930
Leu Gly Asn Thr Gly Leu Leu Tyr Thr Pro Asn Gln Phe Leu Tyr Asp
        1285                1290                1295

CGA GAC TCT ATT GTT AAG GAA GTC TTG CCT GAG TTG CAG AAG CTT GAT     3978
Arg Asp Ser Ile Val Lys Glu Val Leu Pro Glu Leu Gln Lys Leu Asp
        1300                1305                1310

TAC CAG TCA GAT GCT ATC AGA AAG ACA CTT GGT ATT TCT CCA GAA GTT     4026
Tyr Gln Ser Asp Ala Ile Arg Lys Thr Leu Gly Ile Ser Pro Glu Val
    1315                1320                1325

AAG TTA ACC GAG CTC TAT TTA GAA GAC CAG TTC TCC AAA ACA AAA CAA     4074
Lys Leu Thr Glu Leu Tyr Leu Glu Asp Gln Phe Ser Lys Thr Lys Gln
1330                1335                1340                1345

AAT CTG GGA GAC AGC TTG AAA AAA CTT TTG TCA GCA GAT GCC GGT CTA     4122
Asn Leu Gly Asp Ser Leu Lys Lys Leu Leu Ser Ala Asp Ala Gly Leu
            1350                1355                1360

GCT AGC GAT AAC TCA GTC ACC AGA GGC TAT CTT GTA GAT AAA ATC AAG     4170
Ala Ser Asp Asn Ser Val Thr Arg Gly Tyr Leu Val Asp Lys Ile Lys
        1365                1370                1375

AAT AAT AAG GAA GCC TTG CTA CTC GGT TTA ACT TAT TTA GAA CGT TGG     4218
```

```
                Asn Asn Lys Glu Ala Leu Leu Leu Gly Leu Thr Tyr Leu Glu Arg Trp
                    1380                1385                1390

TAT AAC TTT AAC TAT GGT CAA GTG AAT GTC AAA GAC CTA GTT ATG TAT              4266
Tyr Asn Phe Asn Tyr Gly Gln Val Asn Val Lys Asp Leu Val Met Tyr
        1395                1400                1405

CAT CCA GAC TTC TTT GGT AAA GGA AAT ACT TCC CCA CTA GAT ACT CTG              4314
His Pro Asp Phe Phe Gly Lys Gly Asn Thr Ser Pro Leu Asp Thr Leu
1410                1415                1420                1425

ATT GAG TTA GGT AAA TCT GGC TTT AAC AAT CTT CTA GCT AAG AAT AAT              4362
Ile Glu Leu Gly Lys Ser Gly Phe Asn Asn Leu Leu Ala Lys Asn Asn
                1430                1435                1440

GTC GAT ACT TAT GGT ATC AGT CTT GCC AGT CAA CAT GGA GCG ACA GAT              4410
Val Asp Thr Tyr Gly Ile Ser Leu Ala Ser Gln His Gly Ala Thr Asp
                    1445                1450                1455

TTG TTT AGC ACG CTG GAA CAT TAC CGA AAA GTC TTT TTA CCA AAT ACA              4458
Leu Phe Ser Thr Leu Glu His Tyr Arg Lys Val Phe Leu Pro Asn Thr
            1460                1465                1470

AGC AAT AAT GAC TGG TTT AAA TCA GAG ACT AAG GCT TAC ATT GTC GAA              4506
Ser Asn Asn Asp Trp Phe Lys Ser Glu Thr Lys Ala Tyr Ile Val Glu
        1475                1480                1485

GAA AAA TCC ACT ATC GAA GAG GTG AAA ACG AAG CAA GGG TTA GCT GGC              4554
Glu Lys Ser Thr Ile Glu Glu Val Lys Thr Lys Gln Gly Leu Ala Gly
1490                1495                1500                1505

ACC AAG TAT TCT ATC GGT GTT TAT GAT CGT ATC ACG AGT GCC ACA TGG              4602
Thr Lys Tyr Ser Ile Gly Val Tyr Asp Arg Ile Thr Ser Ala Thr Trp
                1510                1515                1520

AAA TAC CGC AAT ATG GTC TTG CCT CTC CTG ACC TTG CCA GAG AGA TCC              4650
Lys Tyr Arg Asn Met Val Leu Pro Leu Leu Thr Leu Pro Glu Arg Ser
                    1525                1530                1535

GTA TTT GTC ATC TCG ACC ATG TCT AGT CTA GGA TTT GGA GCT TAT GAT              4698
Val Phe Val Ile Ser Thr Met Ser Ser Leu Gly Phe Gly Ala Tyr Asp
            1540                1545                1550

CGC TAC CGC AGT AGT GAC CAT AAA GCG GGC AAG GCT CTC AAT GAT TTT              4746
Arg Tyr Arg Ser Ser Asp His Lys Ala Gly Lys Ala Leu Asn Asp Phe
        1555                1560                1565

GTT GAA GAA AAT GCG CGT GAA ACA GCC AAA CGT CAG CGA GAT CAC TAC              4794
Val Glu Glu Asn Ala Arg Glu Thr Ala Lys Arg Gln Arg Asp His Tyr
1570                1575                1580                1585

GAT TAT TGG TAT CGT ATT TTA GTG AAC AGT CAA CGG CGA AAA ACT CTA              4842
Asp Tyr Trp Tyr Arg Ile Leu Val Asn Ser Gln Arg Arg Lys Thr Leu
                1590                1595                1600

TTC GTA CGA TTC TCC CTT TAT GAT GCC TAT AAG TTT GGG GAT GAC ACA              4890
Phe Val Arg Phe Ser Leu Tyr Asp Ala Tyr Lys Phe Gly Asp Asp Thr
                    1605                1610                1615

ACA TCA GGA AAA GCT ACA GCG GAG GCT AAG TTT GAT AGC TCC AAT CCA              4938
Thr Ser Gly Lys Ala Thr Ala Glu Ala Lys Phe Asp Ser Ser Asn Pro
            1620                1625                1630

GCT ATG AAG AAC TTC TTT GGA CCA GTT GGC AAT AAG GTA GTA CAC AAC              4986
Ala Met Lys Asn Phe Phe Gly Pro Val Gly Asn Lys Val Val His Asn
        1635                1640                1645

CAG CAT GGA GCC TAC GCT ACA GGG GAC GGC GTC TAC TAT ATG TCT TAC              5034
Gln His Gly Ala Tyr Ala Thr Gly Asp Gly Val Tyr Tyr Met Ser Tyr
1650                1655                1660                1665

CGC ATG CTG GAC AAG GAT GGA GCC ATT AAT TAT ACC CAT GAA ATG ACC              5082
Arg Met Leu Asp Lys Asp Gly Ala Ile Asn Tyr Thr His Glu Met Thr
                1670                1675                1680

CAT GAT TCG GAT CAG GAT ATT TAC CTT GGT GGC TAT GGT CGA AGA AAT              5130
His Asp Ser Asp Gln Asp Ile Tyr Leu Gly Gly Tyr Gly Arg Arg Asn
                    1685                1690                1695

GGC TTG GGA CCA GAG TTT TTT GCA AAA GGC TTA TTG CAA GCC CCT GAC              5178
```

|  |  |
|---|---|
| Gly Leu Gly Pro Glu Phe Phe Ala Lys Gly Leu Leu Gln Ala Pro Asp<br>        1700                 1705                 1710 |  |
| CAA CCA AGT GAC GCA ACC ATT ACC ATT AAT TTT ATT TTG AAA CAC TCA<br>Gln Pro Ser Asp Ala Thr Ile Thr Ile Asn Phe Ile Leu Lys His Ser<br>        1715                 1720                 1725 | 5226 |
| AAA TCA GAT AGT ACA GAG GGA TCC CGT CTT CAA GTC TTG GAT CCG ACA<br>Lys Ser Asp Ser Thr Glu Gly Ser Arg Leu Gln Val Leu Asp Pro Thr<br>1730                 1735                 1740                 1745 | 5274 |
| GAG AGA TTC CAA AAC GCA GCA GAT TTT CAG AAC TAT GTC CAT AAC ATG<br>Glu Arg Phe Gln Asn Ala Ala Asp Phe Gln Asn Tyr Val His Asn Met<br>                 1750                 1755                 1760 | 5322 |
| TTT GAC CTT ATC TAC ATG ATG GAA TAT CTC GAA GGG CAG TCA ATC GTT<br>Phe Asp Leu Ile Tyr Met Met Glu Tyr Leu Glu Gly Gln Ser Ile Val<br>        1765                 1770                 1775 | 5370 |
| AAT AAA CTA AGT GTT TAC CAG AAA ATG GCG GCT CTC AGA AAA ATT GAG<br>Asn Lys Leu Ser Val Tyr Gln Lys Met Ala Ala Leu Arg Lys Ile Glu<br>        1780                 1785                 1790 | 5418 |
| AAC AAG TAT GTG AAA GAT CCA GCA GAT GGA AAT GAG GTT TAT GCC ACT<br>Asn Lys Tyr Val Lys Asp Pro Ala Asp Gly Asn Glu Val Tyr Ala Thr<br>        1795                 1800                 1805 | 5466 |
| AAC GTA GTC AAA GAA TTG ACA GAA GCA GAG GCC CGA AAC CTG AAT AGT<br>Asn Val Val Lys Glu Leu Thr Glu Ala Glu Ala Arg Asn Leu Asn Ser<br>1810                 1815                 1820                 1825 | 5514 |
| TTT GAA AGT TTG ATT GAC CAC AAC ATC TTA TCA GCT CGT GAG TAC CAG<br>Phe Glu Ser Leu Ile Asp His Asn Ile Leu Ser Ala Arg Glu Tyr Gln<br>                 1830                 1835                 1840 | 5562 |
| TCT GGC GAC TAT GAA CGA AAT GGC TAC TAT ACC ATC AAA CTC TTT GCC<br>Ser Gly Asp Tyr Glu Arg Asn Gly Tyr Tyr Thr Ile Lys Leu Phe Ala<br>        1845                 1850                 1855 | 5610 |
| CCA ATC TAT TCA GCT CTC AGC AGT GAG AAA GGC ACA CCA GGG GAC CTT<br>Pro Ile Tyr Ser Ala Leu Ser Ser Glu Lys Gly Thr Pro Gly Asp Leu<br>        1860                 1865                 1870 | 5658 |
| ATG GGA CGT AGG ATT GCG TAC GAA CTT TTG GCT GCC AAA GGC TTT AAG<br>Met Gly Arg Arg Ile Ala Tyr Glu Leu Leu Ala Ala Lys Gly Phe Lys<br>        1875                 1880                 1885 | 5706 |
| GAT GGA ATG GTA CCT TAT ATC TCA AAC CAA TAC GAA GAA GAT GCT AAA<br>Asp Gly Met Val Pro Tyr Ile Ser Asn Gln Tyr Glu Glu Asp Ala Lys<br>1890                 1895                 1900                 1905 | 5754 |
| CAA CAA GGG CAA ACT ATC AAT CTT TAT GGT AAA GAA CGG GGC TTG GTG<br>Gln Gln Gly Gln Thr Ile Asn Leu Tyr Gly Lys Glu Arg Gly Leu Val<br>                 1910                 1915                 1920 | 5802 |
| ACC GAT GAG CTT GTT TTG AAA AAG GTA TTT GAC GGT AAG TAT AAA ACT<br>Thr Asp Glu Leu Val Leu Lys Lys Val Phe Asp Gly Lys Tyr Lys Thr<br>        1925                 1930                 1935 | 5850 |
| TGG GCA GAA TTT AAG ACA GCT ATG TAC CAA GAA CGG TGG ATC AGT TTG<br>Trp Ala Glu Phe Lys Thr Ala Met Tyr Gln Glu Arg Trp Ile Ser Leu<br>        1940                 1945                 1950 | 5898 |
| GGA AAC TTG AAG CAG GTG ACC TTT AAA GAT CCG ACA AAA CCA TGG CCA<br>Gly Asn Leu Lys Gln Val Thr Phe Lys Asp Pro Thr Lys Pro Trp Pro<br>        1955                 1960                 1965 | 5946 |
| AGC TAT GGC ACA AAG ACT ATC AAT AAT GTG GAT GAA TTG CAA GCC CTC<br>Ser Tyr Gly Thr Lys Thr Ile Asn Asn Val Asp Glu Leu Gln Ala Leu<br>1970                 1975                 1980                 1985 | 5994 |
| ATG GAC CAA GCT GTT CTC AAG GAT GCT GAA GGT CCA CGT TGG AGT AAT<br>Met Asp Gln Ala Val Leu Lys Asp Ala Glu Gly Pro Arg Trp Ser Asn<br>                 1990                 1995                 2000 | 6042 |
| TAT GAT CCA GAA ATC GAC AGT GCC GTT CAT AAG TTG AAG AGA GCA ATC<br>Tyr Asp Pro Glu Ile Asp Ser Ala Val His Lys Leu Lys Arg Ala Ile<br>        2005                 2010                 2015 | 6090 |
| TTT AAA GCC TAT CTT GAC CAA ACA AAT GAT TTT AGA AGT TCA ATT TTT | 6138 |

```
Phe Lys Ala Tyr Leu Asp Gln Thr Asn Asp Phe Arg Ser Ser Ile Phe
                2020                2025                2030

GAG AAT AAA AAA TAG TGT TTA CTA TTA GGA AAT AAA GTT TAA AAA GGT     6186
Glu Asn Lys Lys     Cys Leu Leu Leu Gly Asn Lys Val     Lys Gly
        2035                    2040                2045

GAT GAA AAA CAA CCC                                                  6201
Asp Glu Lys Gln Pro
        2050
```

(2) INFORMATION FOR SEQ ID NO:2:

(i) SEQUENCE CHARACTERISTICS:
        (A) LENGTH: 2052 amino acids
        (B) TYPE: amino acid
        (D) TOPOLOGY: linear (ii) MOLECULE TYPE: protein (xi) SEQUENCE DESCRIPTION: SEQ ID NO:2:

```
Glu Phe Ser Ser Thr Ala Ser Asn His Phe Asn Asp Tyr Glu His Leu
 1               5                  10                  15

Pro Cys Lys Phe His Gly Arg Cys Tyr Cys Thr Pro Lys Tyr Lys Thr
             20                  25                  30

Lys Tyr Glu Ser Ala Ser Gln Phe Asp Phe Val Asn Glu Tyr Asn
         35                  40                  45

Gly Ile Leu Pro Phe Leu Ile Ile Asp Asn Thr Leu Ile Arg Ser Leu
 50                  55                  60

His Ile Ile Leu Phe Gln Gly Gly Ile Met Glu Lys Tyr Phe Gly Glu
 65                  70                  75                  80

Lys Gln Glu Arg Phe Ser Phe Arg Lys Leu Ser Val Gly Leu Val Ser
             85                  90                  95

Ala Thr Ile Ser Ser Leu Phe Phe Met Ser Val Leu Ala Ser Ser Ser
            100                 105                 110

Val Asp Ala Gln Glu Thr Ala Gly Val His Tyr Lys Tyr Val Ala Asp
            115                 120                 125

Ser Glu Leu Ser Ser Glu Glu Lys Lys Gln Leu Val Tyr Asp Ile Pro
130                 135                 140

Thr Tyr Val Glu Asn Asp Asp Glu Thr Tyr Tyr Leu Val Tyr Lys Leu
145                 150                 155                 160

Asn Ser Gln Asn Gln Leu Ala Glu Leu Pro Asn Thr Gly Ser Lys Asn
                165                 170                 175

Glu Arg Gln Ala Leu Val Ala Gly Ser Leu Ala Ala Leu Gly Ile
            180                 185                 190

Leu Ile Phe Ala Val Ser Lys Lys Lys Val Lys Asn Lys Thr Val Leu
            195                 200                 205

His Leu Val Leu Val Ala Gly Met Gly Asn Gly Val Leu Val Ser Val
            210                 215                 220

His Ala Leu Glu Asn His Leu Leu Asn Tyr Asn Thr Asp Tyr Glu
225                 230                 235                 240

Leu Thr Ser Gly Glu Lys Leu Pro Leu Pro Lys Glu Ile Ser Gly Tyr
                245                 250                 255

Thr Tyr Ile Gly Tyr Ile Lys Glu Gly Lys Thr Thr Ser Asp Phe Glu
                260                 265                 270

Val Ser Asn Gln Glu Lys Ser Ala Ala Thr Pro Thr Lys Gln Gln Lys
            275                 280                 285

Val Asp Tyr Asn Val Thr Pro Asn Phe Val Asp His Pro Ser Thr Val
            290                 295                 300
```

```
Gln Ala Ile Gln Glu Gln Thr Pro Val Ser Ser Thr Lys Pro Thr Glu
305                 310                 315                 320

Val Gln Val Val Glu Lys Pro Phe Ser Thr Glu Leu Ile Asn Pro Arg
            325                 330                 335

Lys Glu Glu Lys Gln Ser Ser Asp Ser Gln Glu Gln Leu Ala Glu His
        340                 345                 350

Lys Asn Leu Glu Thr Lys Lys Glu Glu Lys Ile Ser Pro Lys Glu Lys
    355                 360                 365

Thr Gly Val Asn Thr Leu Asn Pro Gln Asp Glu Val Leu Ser Gly Gln
370                 375                 380

Leu Asn Lys Pro Glu Leu Leu Tyr Arg Glu Glu Thr Ile Glu Thr Lys
385                 390                 395                 400

Ile Asp Phe Gln Glu Ile Gln Glu Asn Pro Asp Leu Ala Glu Gly
                405                 410                 415

Thr Val Arg Val Lys Gln Glu Gly Lys Leu Gly Lys Lys Val Glu Ile
            420                 425                 430

Val Arg Ile Phe Ser Val Asn Lys Glu Glu Val Ser Arg Glu Ile Val
        435                 440                 445

Ser Thr Ser Thr Thr Ala Pro Ser Pro Arg Ile Val Glu Lys Gly Thr
    450                 455                 460

Lys Lys Thr Gln Val Ile Lys Glu Gln Pro Glu Thr Gly Val Glu His
465                 470                 475                 480

Lys Asp Val Gln Ser Gly Ala Ile Val Glu Pro Ala Ile Gln Pro Glu
                485                 490                 495

Leu Pro Glu Ala Val Val Ser Asp Lys Gly Glu Pro Glu Val Gln Pro
            500                 505                 510

Thr Leu Pro Glu Ala Val Val Thr Asp Lys Gly Glu Thr Glu Val Gln
        515                 520                 525

Pro Glu Ser Pro Asp Thr Val Val Ser Asp Lys Gly Glu Pro Glu Gln
    530                 535                 540

Val Ala Pro Leu Pro Glu Tyr Lys Gly Asn Ile Glu Gln Val Lys Pro
545                 550                 555                 560

Glu Thr Pro Val Glu Lys Thr Lys Glu Gln Gly Pro Glu Lys Thr Glu
                565                 570                 575

Glu Val Pro Val Lys Pro Thr Glu Thr Pro Val Asn Pro Asn Glu
            580                 585                 590

Gly Thr Thr Glu Gly Thr Ser Ile Gln Glu Ala Glu Asn Pro Val Gln
        595                 600                 605

Pro Ala Glu Glu Ser Thr Thr Asn Ser Glu Lys Val Ser Pro Asp Thr
    610                 615                 620

Ser Ser Glu Asn Thr Gly Glu Val Ser Ser Asn Pro Ser Asp Ser Thr
625                 630                 635                 640

Thr Ser Val Gly Glu Ser Asn Lys Pro Glu His Asn Asp Ser Lys Asn
                645                 650                 655

Glu Asn Ser Glu Lys Thr Val Glu Val Pro Val Asn Pro Asn Glu
            660                 665                 670

Gly Thr Val Glu Gly Thr Ser Asn Gln Glu Thr Glu Lys Pro Val Gln
        675                 680                 685

Pro Ala Glu Glu Thr Gln Thr Asn Ser Gly Lys Ile Ala Asn Glu Asn
    690                 695                 700

Thr Gly Glu Val Ser Asn Lys Pro Ser Asp Ser Lys Pro Val Glu
705                 710                 715                 720

Glu Ser Asn Gln Pro Glu Lys Asn Gly Thr Ala Thr Lys Pro Glu Asn
                725                 730                 735
```

```
Ser Gly Asn Thr Thr Ser Glu Asn Gly Gln Thr Glu Pro Glu Lys Lys
            740                 745                 750

Leu Glu Leu Arg Asn Val Ser Asp Ile Glu Leu Tyr Ser Gln Thr Asn
            755                 760                 765

Gly Thr Tyr Arg Gln His Val Ser Leu Asp Gly Ile Pro Glu Asn Thr
            770                 775                 780

Asp Thr Tyr Phe Val Lys Val Lys Ser Ser Ala Phe Lys Asp Val Tyr
785                 790                 795                 800

Ile Pro Val Ala Ser Ile Thr Glu Glu Lys Arg Asn Gly Gln Ser Val
                805                 810                 815

Tyr Lys Ile Thr Ala Lys Ala Glu Lys Leu Gln Gln Glu Leu Glu Asn
            820                 825                 830

Lys Tyr Val Asp Asn Phe Ser Phe Tyr Leu Asp Lys Lys Ala Lys Glu
            835                 840                 845

Glu Asn Thr Asn Phe Thr Ser Phe Ser Asn Leu Val Lys Ala Ile Asn
            850                 855                 860

Gln Asn Pro Ser Gly Thr Tyr His Leu Ala Ala Ser Leu Asn Ala Asn
865                 870                 875                 880

Glu Val Glu Leu Gly Pro Asp Glu Arg Ser Tyr Ile Lys Asp Thr Phe
            885                 890                 895

Thr Gly Arg Leu Ile Gly Glu Lys Asp Gly Lys Ile Tyr Ala Ile Tyr
            900                 905                 910

Asn Leu Lys Lys Pro Leu Phe Glu Asn Leu Ser Gly Ala Thr Val Glu
            915                 920                 925

Lys Leu Ser Leu Lys Asn Val Ala Ile Ser Gly Lys Asn Asp Ile Gly
            930                 935                 940

Ser Leu Ala Asn Glu Ala Thr Asn Gly Thr Lys Ile Lys Gln Val His
945                 950                 955                 960

Val Asp Gly Val Leu Ala Gly Glu Arg Gly Val Gly Gly Leu Leu Ala
            965                 970                 975

Lys Ala Asp Gln Ser Ser Ile Ala Glu Ser Ser Phe Lys Gly Arg Ile
            980                 985                 990

Val Asn Thr Tyr Glu Thr Thr Asp Ala Tyr Asn Ile Gly Gly Leu Val
            995                 1000                1005

Gly His Leu Thr Gly Lys Asn Ala Ser Ile Ala Lys Ser Lys Ala Thr
    1010                1015                1020

Val Thr Ile Ser Ser Asn Thr Asn Arg Ser Asp Gln Thr Val Gly Gly
1025                1030                1035                1040

Leu Ala Gly Leu Val Asp Gln Asp Ala His Ile Gln Asn Ser Tyr Ala
            1045                1050                1055

Glu Gly Asp Ile Asn Asn Val Lys His Phe Gly Lys Val Ala Gly Val
            1060                1065                1070

Ala Gly Tyr Leu Trp Asp Arg Thr Ser Gly Glu Lys His Ala Gly
            1075                1080                1085

Glu Leu Thr Asn Val Leu Ser Asp Val Asn Val Thr Asn Gly Asn Ala
            1090                1095                1100

Ile Thr Gly Tyr His Tyr Thr Gly Met Lys Val Ala Asn Thr Phe Ser
1105                1110                1115                1120

Ser Lys Ala Asn Arg Val Phe Asn Val Thr Leu Glu Lys Asp Glu Val
            1125                1130                1135

Val Ser Lys Glu Ser Phe Glu Arg Gly Thr Met Leu Asp Ala Ser
            1140                1145                1150

Gln Ile Val Ser Lys Lys Ala Glu Ile Asn Pro Leu Thr Leu Pro Thr
```

-continued

```
             1155              1160              1165
Val Glu Pro Leu Ser Thr Ser Gly Lys Lys Asp Ser Asp Phe Ser Lys
    1170              1175              1180

Ile Ala His Tyr Gln Ala Asn Arg Ala Leu Val Tyr Lys Asn Ile Glu
1185              1190              1195              1200

Lys Leu Leu Pro Phe Tyr Asn Lys Ser Thr Ile Val Lys Tyr Gly Asn
            1205              1210              1215

Leu Val Lys Glu Asn Ser Leu Leu Tyr Gln Lys Glu Leu Leu Ser Ala
            1220              1225              1230

Val Met Met Lys Asp Asp Gln Val Ile Thr Asp Ile Val Ser Asn Lys
            1235              1240              1245

Gln Thr Ala Asn Lys Leu Leu Leu His Tyr Asn Asp His Ser Ser Glu
            1250              1255              1260

Lys Phe Asp Leu Lys Tyr Gln Thr Asp Phe Ala Asn Leu Pro Glu Tyr
1265              1270              1275              1280

Asn Leu Gly Asn Thr Gly Leu Leu Tyr Thr Pro Asn Gln Phe Leu Tyr
                1285              1290              1295

Asp Arg Asp Ser Ile Val Lys Glu Val Leu Pro Glu Leu Gln Lys Leu
            1300              1305              1310

Asp Tyr Gln Ser Asp Ala Ile Arg Lys Thr Leu Gly Ile Ser Pro Glu
            1315              1320              1325

Val Lys Leu Thr Glu Leu Tyr Leu Glu Asp Gln Phe Ser Lys Thr Lys
            1330              1335              1340

Gln Asn Leu Gly Asp Ser Leu Lys Lys Leu Leu Ser Ala Asp Ala Gly
1345              1350              1355              1360

Leu Ala Ser Asp Asn Ser Val Thr Arg Gly Tyr Leu Val Asp Lys Ile
            1365              1370              1375

Lys Asn Asn Lys Glu Ala Leu Leu Leu Gly Leu Thr Tyr Leu Glu Arg
            1380              1385              1390

Trp Tyr Asn Phe Asn Tyr Gly Gln Val Asn Val Lys Asp Leu Val Met
            1395              1400              1405

Tyr His Pro Asp Phe Phe Gly Lys Gly Asn Thr Ser Pro Leu Asp Thr
            1410              1415              1420

Leu Ile Glu Leu Gly Lys Ser Gly Phe Asn Asn Leu Leu Ala Lys Asn
1425              1430              1435              1440

Asn Val Asp Thr Tyr Gly Ile Ser Leu Ala Ser Gln His Gly Ala Thr
                1445              1450              1455

Asp Leu Phe Ser Thr Leu Glu His Tyr Arg Lys Val Phe Leu Pro Asn
            1460              1465              1470

Thr Ser Asn Asn Asp Trp Phe Lys Ser Glu Thr Lys Ala Tyr Ile Val
            1475              1480              1485

Glu Glu Lys Ser Thr Ile Glu Glu Val Lys Thr Lys Gln Gly Leu Ala
            1490              1495              1500

Gly Thr Lys Tyr Ser Ile Gly Val Tyr Asp Arg Ile Thr Ser Ala Thr
1505              1510              1515              1520

Trp Lys Tyr Arg Asn Met Val Leu Pro Leu Leu Thr Leu Pro Glu Arg
                1525              1530              1535

Ser Val Phe Val Ile Ser Thr Met Ser Ser Leu Gly Phe Gly Ala Tyr
            1540              1545              1550

Asp Arg Tyr Arg Ser Ser Asp His Lys Ala Gly Lys Ala Leu Asn Asp
            1555              1560              1565

Phe Val Glu Glu Asn Ala Arg Glu Thr Ala Lys Arg Gln Arg Asp His
            1570              1575              1580
```

-continued

Tyr Asp Tyr Trp Tyr Arg Ile Leu Val Asn Ser Gln Arg Arg Lys Thr
1585                1590                1595                1600

Leu Phe Val Arg Phe Ser Leu Tyr Asp Ala Tyr Lys Phe Gly Asp Asp
                1605                1610                1615

Thr Thr Ser Gly Lys Ala Thr Ala Glu Ala Lys Phe Asp Ser Ser Asn
        1620                1625                1630

Pro Ala Met Lys Asn Phe Phe Gly Pro Val Gly Asn Lys Val Val His
        1635                1640                1645

Asn Gln His Gly Ala Tyr Ala Thr Gly Asp Gly Val Tyr Tyr Met Ser
        1650                1655                1660

Tyr Arg Met Leu Asp Lys Asp Gly Ala Ile Asn Tyr Thr His Glu Met
1665                1670                1675                1680

Thr His Asp Ser Asp Gln Asp Ile Tyr Leu Gly Gly Tyr Gly Arg Arg
                1685                1690                1695

Asn Gly Leu Gly Pro Glu Phe Phe Ala Lys Gly Leu Leu Gln Ala Pro
        1700                1705                1710

Asp Gln Pro Ser Asp Ala Thr Ile Thr Ile Asn Phe Ile Leu Lys His
        1715                1720                1725

Ser Lys Ser Asp Ser Thr Glu Gly Ser Arg Leu Gln Val Leu Asp Pro
        1730                1735                1740

Thr Glu Arg Phe Gln Asn Ala Ala Asp Phe Gln Asn Tyr Val His Asn
1745                1750                1755                1760

Met Phe Asp Leu Ile Tyr Met Met Glu Tyr Leu Glu Gly Gln Ser Ile
                1765                1770                1775

Val Asn Lys Leu Ser Val Tyr Gln Lys Met Ala Ala Leu Arg Lys Ile
        1780                1785                1790

Glu Asn Lys Tyr Val Lys Asp Pro Ala Asp Gly Asn Glu Val Tyr Ala
        1795                1800                1805

Thr Asn Val Val Lys Glu Leu Thr Glu Ala Glu Ala Arg Asn Leu Asn
        1810                1815                1820

Ser Phe Glu Ser Leu Ile Asp His Asn Ile Leu Ser Ala Arg Glu Tyr
1825                1830                1835                1840

Gln Ser Gly Asp Tyr Glu Arg Asn Gly Tyr Tyr Thr Ile Lys Leu Phe
                1845                1850                1855

Ala Pro Ile Tyr Ser Ala Leu Ser Ser Glu Lys Gly Thr Pro Gly Asp
        1860                1865                1870

Leu Met Gly Arg Arg Ile Ala Tyr Glu Leu Leu Ala Ala Lys Gly Phe
        1875                1880                1885

Lys Asp Gly Met Val Pro Tyr Ile Ser Asn Gln Tyr Glu Glu Asp Ala
        1890                1895                1900

Lys Gln Gln Gly Gln Thr Ile Asn Leu Tyr Gly Lys Glu Arg Gly Leu
1905                1910                1915                1920

Val Thr Asp Glu Leu Val Leu Lys Lys Val Phe Asp Gly Lys Tyr Lys
                1925                1930                1935

Thr Trp Ala Glu Phe Lys Thr Ala Met Tyr Gln Glu Arg Trp Ile Ser
        1940                1945                1950

Leu Gly Asn Leu Lys Gln Val Thr Phe Lys Asp Pro Thr Lys Pro Trp
        1955                1960                1965

Pro Ser Tyr Gly Thr Lys Thr Ile Asn Asn Val Asp Glu Leu Gln Ala
        1970                1975                1980

Leu Met Asp Gln Ala Val Leu Lys Asp Ala Glu Gly Pro Arg Trp Ser
1985                1990                1995                2000

Asn Tyr Asp Pro Glu Ile Asp Ser Ala Val His Lys Leu Lys Arg Ala
                2005                2010                2015

```
Ile Phe Lys Ala Tyr Leu Asp Gln Thr Asn Asp Phe Arg Ser Ser Ile
            2020                2025                2030

Phe Glu Asn Lys Lys Cys Leu Leu Leu Gly Asn Lys Val Lys Gly Asp
            2035                2040                2045

Glu Lys Gln Pro
        2050

(2) INFORMATION FOR SEQ ID NO:3:

(i) SEQUENCE CHARACTERISTICS:
        (A) LENGTH: 1964 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

Met Glu Lys Tyr Phe Gly Glu Lys Gln Glu Arg Phe Ser Phe Arg Lys
1               5                   10                  15

Leu Ser Val Gly Leu Val Ser Ala Thr Ile Ser Ser Leu Phe Phe Met
            20                  25                  30

Ser Val Leu Ala Ser Ser Val Asp Ala Gln Glu Thr Ala Gly Val
            35                  40                  45

His Tyr Lys Tyr Val Ala Asp Ser Glu Leu Ser Ser Glu Lys Lys
    50                  55                  60

Gln Leu Val Tyr Asp Ile Pro Thr Tyr Val Asn Asp Asp Glu Thr
65                  70                  75                  80

Tyr Tyr Leu Val Tyr Lys Leu Asn Ser Gln Asn Gln Leu Ala Glu Leu
                85                  90                  95

Pro Asn Thr Gly Ser Lys Asn Glu Arg Gln Ala Leu Val Ala Gly Ala
            100                 105                 110

Ser Leu Ala Ala Leu Gly Ile Leu Ile Phe Ala Val Ser Lys Lys Lys
            115                 120                 125

Val Lys Asn Lys Thr Val Leu His Leu Val Leu Ala Gly Met Gly
            130                 135                 140

Asn Gly Val Leu Val Ser Val His Ala Leu Glu Asn His Leu Leu Leu
145                 150                 155                 160

Asn Tyr Asn Thr Asp Tyr Glu Leu Thr Ser Gly Lys Leu Pro Leu
            165                 170                 175

Pro Lys Glu Ile Ser Gly Tyr Thr Tyr Ile Gly Tyr Ile Lys Glu Gly
            180                 185                 190

Lys Thr Thr Ser Asp Phe Glu Val Ser Asn Gln Glu Lys Ser Ala Ala
            195                 200                 205

Thr Pro Thr Lys Gln Gln Lys Val Asp Tyr Asn Val Thr Pro Asn Phe
            210                 215                 220

Val Asp His Pro Ser Thr Val Gln Ala Ile Gln Glu Gln Thr Pro Val
225                 230                 235                 240

Ser Ser Thr Lys Pro Thr Glu Val Gln Val Glu Lys Pro Phe Ser
            245                 250                 255

Thr Glu Leu Ile Asn Pro Arg Lys Glu Glu Lys Gln Ser Ser Asp Ser
            260                 265                 270

Gln Glu Gln Leu Ala Glu His Lys Asn Leu Glu Thr Lys Lys Glu Glu
            275                 280                 285

Lys Ile Ser Pro Lys Glu Lys Thr Gly Val Asn Thr Leu Asn Pro Gln
            290                 295                 300
```

-continued

```
Asp Glu Val Leu Ser Gly Gln Leu Asn Lys Pro Glu Leu Leu Tyr Arg
305                 310                 315                 320

Glu Glu Thr Ile Glu Thr Lys Ile Asp Phe Gln Glu Ile Gln Glu
            325                 330                 335

Asn Pro Asp Leu Ala Glu Gly Thr Val Arg Val Lys Gln Glu Gly Lys
                340                 345                 350

Leu Gly Lys Lys Val Glu Ile Val Arg Ile Phe Ser Val Asn Lys Glu
            355                 360                 365

Glu Val Ser Arg Glu Ile Val Ser Thr Ser Thr Ala Pro Ser Pro
    370                 375                 380

Arg Ile Val Glu Lys Gly Thr Lys Lys Thr Gln Val Ile Lys Glu Gln
385                 390                 395                 400

Pro Glu Thr Gly Val Glu His Lys Asp Val Gln Ser Gly Ala Ile Val
                405                 410                 415

Glu Pro Ala Ile Gln Pro Glu Leu Pro Glu Ala Val Val Ser Asp Lys
            420                 425                 430

Gly Glu Pro Glu Val Gln Pro Thr Leu Pro Glu Ala Val Val Thr Asp
    435                 440                 445

Lys Gly Glu Thr Glu Val Gln Pro Glu Ser Pro Asp Thr Val Val Ser
    450                 455                 460

Asp Lys Gly Glu Pro Glu Gln Val Ala Pro Leu Pro Glu Tyr Lys Gly
465                 470                 475                 480

Asn Ile Glu Gln Val Lys Pro Glu Thr Pro Val Glu Lys Thr Lys Glu
            485                 490                 495

Gln Gly Pro Glu Lys Thr Glu Val Pro Val Lys Pro Thr Glu Glu
            500                 505                 510

Thr Pro Val Asn Pro Asn Glu Gly Thr Thr Glu Gly Thr Ser Ile Gln
            515                 520                 525

Glu Ala Glu Asn Pro Val Gln Pro Ala Glu Glu Ser Thr Thr Asn Ser
530                 535                 540

Glu Lys Val Ser Pro Asp Thr Ser Ser Glu Asn Thr Gly Glu Val Ser
545                 550                 555                 560

Ser Asn Pro Ser Asp Ser Thr Thr Ser Val Gly Glu Ser Asn Lys Pro
                565                 570                 575

Glu His Asn Asp Ser Lys Asn Glu Asn Ser Glu Lys Thr Val Glu Glu
            580                 585                 590

Val Pro Val Asn Pro Asn Glu Gly Thr Val Glu Gly Thr Ser Asn Gln
            595                 600                 605

Glu Thr Glu Lys Pro Val Gln Pro Ala Glu Glu Thr Gln Thr Asn Ser
    610                 615                 620

Gly Lys Ile Ala Asn Glu Asn Thr Gly Glu Val Ser Asn Lys Pro Ser
625                 630                 635                 640

Asp Ser Lys Pro Pro Val Glu Glu Ser Asn Gln Pro Glu Lys Asn Gly
                645                 650                 655

Thr Ala Thr Lys Pro Glu Asn Ser Gly Asn Thr Thr Ser Glu Asn Gly
                660                 665                 670

Gln Thr Glu Pro Glu Lys Lys Leu Glu Leu Arg Asn Val Ser Asp Ile
            675                 680                 685

Glu Leu Tyr Ser Gln Thr Asn Gly Thr Tyr Arg Gln His Val Ser Leu
            690                 695                 700

Asp Gly Ile Pro Glu Asn Thr Asp Thr Tyr Phe Val Lys Val Lys Ser
705                 710                 715                 720

Ser Ala Phe Lys Asp Val Tyr Ile Pro Val Ala Ser Ile Thr Glu Glu
                725                 730                 735
```

```
Lys Arg Asn Gly Gln Ser Val Tyr Lys Ile Thr Ala Lys Ala Glu Lys
            740                 745                 750

Leu Gln Gln Glu Leu Glu Asn Lys Tyr Val Asp Asn Phe Ser Phe Tyr
            755                 760                 765

Leu Asp Lys Lys Ala Lys Glu Glu Asn Thr Asn Phe Thr Ser Phe Ser
            770                 775                 780

Asn Leu Val Lys Ala Ile Asn Gln Asn Pro Ser Gly Thr Tyr His Leu
785                 790                 795                 800

Ala Ala Ser Leu Asn Ala Asn Glu Val Glu Leu Gly Pro Asp Glu Arg
                805                 810                 815

Ser Tyr Ile Lys Asp Thr Phe Thr Gly Arg Leu Ile Gly Glu Lys Asp
                820                 825                 830

Gly Lys Ile Tyr Ala Ile Tyr Asn Leu Lys Lys Pro Leu Phe Glu Asn
                835                 840                 845

Leu Ser Gly Ala Thr Val Glu Lys Leu Ser Leu Lys Asn Val Ala Ile
            850                 855                 860

Ser Gly Lys Asn Asp Ile Gly Ser Leu Ala Asn Glu Ala Thr Asn Gly
865                 870                 875                 880

Thr Lys Ile Lys Gln Val His Val Asp Gly Val Leu Ala Gly Glu Arg
                885                 890                 895

Gly Val Gly Gly Leu Leu Ala Lys Ala Asp Gln Ser Ser Ile Ala Glu
            900                 905                 910

Ser Ser Phe Lys Gly Arg Ile Val Asn Thr Tyr Glu Thr Thr Asp Ala
            915                 920                 925

Tyr Asn Ile Gly Gly Leu Val Gly His Leu Thr Gly Lys Asn Ala Ser
            930                 935                 940

Ile Ala Lys Ser Lys Ala Thr Val Thr Ile Ser Ser Asn Thr Asn Arg
945                 950                 955                 960

Ser Asp Gln Thr Val Gly Gly Leu Ala Gly Leu Val Asp Gln Asp Ala
                965                 970                 975

His Ile Gln Asn Ser Tyr Ala Glu Gly Asp Ile Asn Asn Val Lys His
            980                 985                 990

Phe Gly Lys Val Ala Gly Val Ala Gly Tyr Leu Trp Asp Arg Thr Ser
            995                 1000                1005

Gly Glu Glu Lys His Ala Gly Glu Leu Thr Asn Val Leu Ser Asp Val
            1010                1015                1020

Asn Val Thr Asn Gly Asn Ala Ile Thr Gly Tyr His Tyr Thr Gly Met
1025                1030                1035                1040

Lys Val Ala Asn Thr Phe Ser Ser Lys Ala Asn Arg Val Phe Asn Val
                1045                1050                1055

Thr Leu Glu Lys Asp Glu Val Val Ser Lys Glu Ser Phe Glu Glu Arg
            1060                1065                1070

Gly Thr Met Leu Asp Ala Ser Gln Ile Val Ser Lys Lys Ala Glu Ile
            1075                1080                1085

Asn Pro Leu Thr Leu Pro Thr Val Glu Pro Leu Ser Thr Ser Gly Lys
            1090                1095                1100

Lys Asp Ser Asp Phe Ser Lys Ile Ala His Tyr Gln Ala Asn Arg Ala
1105                1110                1115                1120

Leu Val Tyr Lys Asn Ile Glu Lys Leu Leu Pro Phe Tyr Asn Lys Ser
                1125                1130                1135

Thr Ile Val Lys Tyr Gly Asn Leu Val Lys Glu Asn Ser Leu Leu Tyr
            1140                1145                1150

Gln Lys Glu Leu Leu Ser Ala Val Met Met Lys Asp Asp Gln Val Ile
```

-continued

```
            1155              1160              1165
Thr Asp Ile Val Ser Asn Lys Gln Thr Ala Asn Lys Leu Leu Leu His
1170              1175              1180

Tyr Asn Asp His Ser Ser Glu Lys Phe Asp Leu Lys Tyr Gln Thr Asp
1185              1190              1195              1200

Phe Ala Asn Leu Pro Glu Tyr Asn Leu Gly Asn Thr Gly Leu Leu Tyr
            1205              1210              1215

Thr Pro Asn Gln Phe Leu Tyr Asp Arg Asp Ser Ile Val Lys Glu Val
            1220              1225              1230

Leu Pro Glu Leu Gln Lys Leu Asp Tyr Gln Ser Asp Ala Ile Arg Lys
            1235              1240              1245

Thr Leu Gly Ile Ser Pro Glu Val Lys Leu Thr Glu Leu Tyr Leu Glu
            1250              1255              1260

Asp Gln Phe Ser Lys Thr Lys Gln Asn Leu Gly Asp Ser Leu Lys Lys
1265              1270              1275              1280

Leu Leu Ser Ala Asp Ala Gly Leu Ala Ser Asp Asn Ser Val Thr Arg
                  1285              1290              1295

Gly Tyr Leu Val Asp Lys Ile Lys Asn Asn Lys Glu Ala Leu Leu Leu
            1300              1305              1310

Gly Leu Thr Tyr Leu Glu Arg Trp Tyr Asn Phe Asn Tyr Gly Gln Val
            1315              1320              1325

Asn Val Lys Asp Leu Val Met Tyr His Pro Asp Phe Phe Gly Lys Gly
            1330              1335              1340

Asn Thr Ser Pro Leu Asp Thr Leu Ile Glu Leu Gly Lys Ser Gly Phe
1345              1350              1355              1360

Asn Asn Leu Leu Ala Lys Asn Asn Val Asp Thr Tyr Gly Ile Ser Leu
                  1365              1370              1375

Ala Ser Gln His Gly Ala Thr Asp Leu Phe Ser Thr Leu Glu His Tyr
            1380              1385              1390

Arg Lys Val Phe Leu Pro Asn Thr Ser Asn Asn Asp Trp Phe Lys Ser
            1395              1400              1405

Glu Thr Lys Ala Tyr Ile Val Glu Glu Lys Ser Thr Ile Glu Glu Val
            1410              1415              1420

Lys Thr Lys Gln Gly Leu Ala Gly Thr Lys Tyr Ser Ile Gly Val Tyr
1425              1430              1435              1440

Asp Arg Ile Thr Ser Ala Thr Trp Lys Tyr Arg Asn Met Val Leu Pro
                  1445              1450              1455

Leu Leu Thr Leu Pro Glu Arg Ser Val Phe Val Ile Ser Thr Met Ser
            1460              1465              1470

Ser Leu Gly Phe Gly Ala Tyr Asp Arg Tyr Arg Ser Ser Asp His Lys
            1475              1480              1485

Ala Gly Lys Ala Leu Asn Asp Phe Val Glu Glu Asn Ala Arg Glu Thr
            1490              1495              1500

Ala Lys Arg Gln Arg Asp His Tyr Asp Tyr Trp Tyr Arg Ile Leu Val
1505              1510              1515              1520

Asn Ser Gln Arg Arg Lys Thr Leu Phe Val Arg Phe Ser Leu Tyr Asp
                  1525              1530              1535

Ala Tyr Lys Phe Gly Asp Asp Thr Thr Ser Gly Lys Ala Thr Ala Glu
            1540              1545              1550

Ala Lys Phe Asp Ser Ser Asn Pro Ala Met Lys Asn Phe Phe Gly Pro
            1555              1560              1565

Val Gly Asn Lys Val Val His Asn Gln His Gly Ala Tyr Ala Thr Gly
            1570              1575              1580
```

```
Asp Gly Val Tyr Tyr Met Ser Tyr Arg Met Leu Asp Lys Asp Gly Ala
1585                1590                1595                1600

Ile Asn Tyr Thr His Glu Met Thr His Asp Ser Asp Gln Asp Ile Tyr
            1605                1610                1615

Leu Gly Gly Tyr Gly Arg Arg Asn Gly Leu Gly Pro Glu Phe Phe Ala
        1620                1625                1630

Lys Gly Leu Leu Gln Ala Pro Asp Gln Pro Ser Asp Ala Thr Ile Thr
    1635                1640                1645

Ile Asn Phe Ile Leu Lys His Ser Lys Ser Asp Ser Thr Glu Gly Ser
1650                1655                1660

Arg Leu Gln Val Leu Asp Pro Thr Glu Arg Phe Gln Asn Ala Ala Asp
1665                1670                1675                1680

Phe Gln Asn Tyr Val His Asn Met Phe Asp Leu Ile Tyr Met Met Glu
            1685                1690                1695

Tyr Leu Glu Gly Gln Ser Ile Val Asn Lys Leu Ser Val Tyr Gln Lys
        1700                1705                1710

Met Ala Ala Leu Arg Lys Ile Glu Asn Lys Tyr Val Lys Asp Pro Ala
    1715                1720                1725

Asp Gly Asn Glu Val Tyr Ala Thr Asn Val Val Lys Glu Leu Thr Glu
1730                1735                1740

Ala Glu Ala Arg Asn Leu Asn Ser Phe Glu Ser Leu Ile Asp His Asn
1745                1750                1755                1760

Ile Leu Ser Ala Arg Glu Tyr Gln Ser Gly Asp Tyr Glu Arg Asn Gly
            1765                1770                1775

Tyr Tyr Thr Ile Lys Leu Phe Ala Pro Ile Tyr Ser Ala Leu Ser Ser
        1780                1785                1790

Glu Lys Gly Thr Pro Gly Asp Leu Met Gly Arg Arg Ile Ala Tyr Glu
    1795                1800                1805

Leu Leu Ala Ala Lys Gly Phe Lys Asp Gly Met Val Pro Tyr Ile Ser
1810                1815                1820

Asn Gln Tyr Glu Glu Asp Ala Lys Gln Gln Gly Gln Thr Ile Asn Leu
1825                1830                1835                1840

Tyr Gly Lys Glu Arg Gly Leu Val Thr Asp Glu Leu Val Leu Lys Lys
            1845                1850                1855

Val Phe Asp Gly Lys Tyr Lys Trp Ala Glu Phe Lys Thr Ala Met
        1860                1865                1870

Tyr Gln Glu Arg Trp Ile Ser Leu Gly Asn Leu Lys Gln Val Thr Phe
    1875                1880                1885

Lys Asp Pro Thr Lys Pro Trp Pro Ser Tyr Gly Thr Lys Thr Ile Asn
1890                1895                1900

Asn Val Asp Glu Leu Gln Ala Leu Met Asp Gln Ala Val Leu Lys Asp
1905                1910                1915                1920

Ala Glu Gly Pro Arg Trp Ser Asn Tyr Asp Pro Glu Ile Asp Ser Ala
            1925                1930                1935

Val His Lys Leu Lys Arg Ala Ile Phe Lys Ala Tyr Leu Asp Gln Thr
        1940                1945                1950

Asn Asp Phe Arg Ser Ser Ile Phe Glu Asn Lys Lys
    1955                1960
```

(2) INFORMATION FOR SEQ ID NO:4:

(i) SEQUENCE CHARACTERISTICS:
        (A) LENGTH: 1861 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

```
Met Lys Lys Phe Leu Gly Glu Lys Gln Thr Arg Phe Ala Phe Arg Lys
 1               5                  10                  15

Leu Ala Val Gly Leu Val Ser Ala Ala Ile Ser Ser Leu Phe Phe Val
                20                  25                  30

Ser Ile Val Gly Val Asp Ser Val Gln Ala Gln Glu Lys Leu Asn Val
                35                  40                  45

His Tyr Lys Tyr Val Thr Asp Thr Glu Ile Thr Pro Gln Glu Lys Glu
 50                  55                  60

Leu Ile Val Ser Gly Val Pro Arg Met Pro Glu Gly Asn Glu Glu Thr
 65                  70                  75                  80

Tyr Tyr Leu Val Tyr Arg Leu Asn Ser Asn Ala Gly Ala Lys Thr Leu
                85                  90                  95

Pro Asn Thr Gly Asp Asn Asn Ser Asn Thr Met Met Ala Ala Gly Leu
                100                 105                 110

Leu Leu Thr Thr Ile Gly Leu Val Val Phe Ala Val Ser Lys Arg Lys
                115                 120                 125

Val Gln Ser Lys Phe Leu Leu Thr Val Leu Val Gly Ala Ser Val Gly
 130                 135                 140

Gly Gly Leu Ile Leu Ser Val Asp Ala Leu Glu Asn Gly Ser Leu Leu
 145                 150                 155                 160

Gln Tyr Asn Ala Glu Tyr Gln Val Ser Ala Gly Glu Ser Leu Pro Ser
                165                 170                 175

Pro Gly Glu Ile Ser Gly Tyr Thr Tyr Val Gly Tyr Ile Lys Asp Glu
                180                 185                 190

Ser Ile Lys Lys Leu Leu Asp Asn Lys Ile Pro Asp Asn Gln Gln Asn
                195                 200                 205

Ala Asn Val Asp Lys Glu Ala Leu Asn Gln Asn Lys Lys Leu Asp Tyr
 210                 215                 220

Ser Val Ser Phe Asp Lys Asn Gly Leu Lys Asn Gln Thr Val Gly Val
 225                 230                 235                 240

Asn Thr Ile Glu Pro Gln Asp Glu Val Leu Ser Gly Arg Val Ala Lys
                245                 250                 255

Pro Glu Leu Leu Tyr Lys Glu Thr Ser Ile Glu Thr Glu Ile Ala Tyr
                260                 265                 270

Gly Glu Gln Ile Gln Glu Asn Pro Asp Leu Ala Glu Gly Thr Val Arg
                275                 280                 285

Val Lys Gln Glu Gly Lys Pro Gly Arg Lys Ile Glu Val Val Arg Ile
 290                 295                 300

Phe Thr Val Asp Asn Ala Glu Val Ser Arg Glu Val Leu Ser Thr Lys
 305                 310                 315                 320

Ile Glu Glu Ala Thr Pro Lys Ile Val Glu Lys Gly Thr Lys Lys Leu
                325                 330                 335

Glu Ala Pro Ser Glu Lys Pro Val Thr Ser Asn Leu Val Gln Pro Glu
                340                 345                 350

Gln Val Ala Pro Leu Pro Glu Tyr Thr Gly Val Gln Ser Gly Ala Ile
                355                 360                 365

Val Glu Pro Glu Gln Val Ala Ser Leu Pro Glu Tyr Ser Gly Thr Leu
 370                 375                 380

Ser Gly Ala Ile Val Glu Pro Glu Gln Ile Glu Pro Glu Ile Gly Gly
 385                 390                 395                 400
```

```
Val Gln Ser Gly Ala Ile Val Glu Pro Glu Gln Val Thr Pro Leu Pro
            405                 410                 415

Glu Tyr Thr Gly Thr Gln Ala Gly Ala Val Val Ser Pro Glu Gln Val
            420                 425                 430

Ala Pro Leu Pro Glu Tyr Thr Gly Thr Gln Ser Gly Ala Ile Val Glu
            435                 440                 445

Pro Ala Gln Val Thr Pro Leu Pro Glu Tyr Thr Gly Val Gln Ser Gly
450                 455                 460

Ala Ile Val Lys Pro Ala Gln Val Thr Pro Leu Pro Glu Tyr Thr Gly
465                 470                 475                 480

Thr Gln Ser Gly Ala Ile Val Glu Pro Glu Gln Val Thr Pro Ser Pro
                485                 490                 495

Glu Tyr Thr Gly Val Gln Ala Gly Ala Ile Val Glu Pro Glu Gln Val
            500                 505                 510

Ala Ser Leu Pro Glu Tyr Thr Gly Ser Gln Ala Gly Ala Ile Val Glu
            515                 520                 525

Pro Glu Gln Val Glu Pro Pro Gln Glu Tyr Thr Gly Asn Ile Glu Pro
            530                 535                 540

Ala Ala Pro Glu Ala Glu Asn Pro Thr Glu Lys Ala Gln Glu Pro Lys
545                 550                 555                 560

Glu Gln Lys Gln Glu Pro Glu Lys Asn Ile Glu Leu Arg Asn Val Ser
                565                 570                 575

Asp Val Glu Leu Tyr Ser Leu Ala Asp Gly Lys Tyr Lys Gln His Val
            580                 585                 590

Ser Leu Asp Ala Ile Pro Ser Asn Gln Glu Asn Tyr Phe Val Lys Val
            595                 600                 605

Lys Ser Ser Lys Phe Lys Asp Val Phe Leu Pro Ile Ser Ser Ile Val
610                 615                 620

Asp Ser Thr Lys Asp Gly Gln Pro Val Tyr Lys Ile Thr Ala Ser Ala
625                 630                 635                 640

Glu Lys Leu Lys Gln Asp Val Asn Asn Lys Tyr Glu Asp Asn Phe Thr
                645                 650                 655

Phe Tyr Leu Ala Lys Lys Ala Glu Arg Glu Val Thr Asn Phe Thr Ser
            660                 665                 670

Phe Ser Asn Leu Val Gln Ala Ile Asn Asn Leu Asn Gly Thr Tyr
            675                 680                 685

Tyr Leu Ala Ala Ser Leu Asn Ala Asn Glu Val Glu Leu Glu Asn Gly
690                 695                 700

Ala Ser Ser Tyr Ile Lys Gly Arg Phe Thr Gly Lys Leu Phe Gly Ser
705                 710                 715                 720

Lys Asp Gly Lys Asn Tyr Ala Ile Tyr Asn Leu Lys Lys Pro Leu Phe
                725                 730                 735

Asp Thr Leu Ser Ala Ala Thr Val Glu Asn Leu Thr Leu Lys Asp Val
            740                 745                 750

Asn Ile Ser Gly Lys Thr Asp Ile Gly Ala Leu Ala Asn Glu Ala Asn
            755                 760                 765

Asn Ala Thr Arg Ile Asn Asn Val His Val Asp Gly Val Leu Ala Gly
770                 775                 780

Glu Arg Gly Ile Gly Gly Leu Val Trp Lys Ala Asp Asn Ser Lys Ile
785                 790                 795                 800

Ser Asn Ser Ser Phe Lys Gly Arg Ile Val Asn Ser Tyr Glu Thr Lys
                805                 810                 815

Ala Pro Tyr Asn Ile Gly Gly Leu Val Gly Gln Leu Thr Gly Ile Asn
            820                 825                 830
```

```
Ala Leu Val Asp Lys Ser Lys Ala Thr Ile Thr Ile Ser Ser Asn Ala
        835                 840                 845

Asp Ser Thr Asn Gln Thr Val Gly Gly Leu Ala Gly Leu Val Glu Lys
850                 855                 860

Asp Ala Leu Ile Ser Asn Ser Tyr Ala Glu Gly Asn Ile Asn Asn Val
865                 870                 875                 880

Lys Arg Phe Gly Ser Val Ala Gly Val Ala Gly Tyr Leu Trp Asp Arg
                885                 890                 895

Asp Ser Ser Glu Glu Arg His Ala Gly Arg Leu His Asn Val Leu Ser
                900                 905                 910

Asp Ile Asn Val Met Asn Gly Asn Ala Ile Ser Gly Tyr His Tyr Arg
        915                 920                 925

Gly Met Arg Ile Thr Asp Ser Tyr Ser Asn Lys Asp Asn Arg Val Tyr
        930                 935                 940

Lys Val Thr Leu Glu Lys Asp Glu Val Val Thr Lys Glu Ser Leu Glu
945                 950                 955                 960

Glu Arg Gly Thr Ile Leu Asp Val Ser Gln Ile Ala Ser Lys Lys Ser
                965                 970                 975

Glu Ile Asn Ser Leu Ser Ala Pro Lys Val Glu Thr Leu Leu Thr Ser
                980                 985                 990

Thr Asn Lys Glu Ser Asp Phe Ser Lys Val Lys Asp Tyr Gln Ala Ser
        995                 1000                1005

Arg Ala Leu Ala Tyr Lys Asn Ile Glu Lys Leu Leu Pro Phe Tyr Asn
    1010                1015                1020

Lys Ala Thr Ile Val Lys Tyr Gly Asn Leu Val Lys Glu Asp Ser Thr
1025                1030                1035                1040

Leu Tyr Glu Lys Glu Ile Leu Ser Ala Val Met Met Lys Asp Asn Glu
                1045                1050                1055

Val Ile Thr Asp Ile Ala Ser His Lys Glu Ala Ala Asn Lys Leu Leu
        1060                1065                1070

Ile His Tyr Lys Asp His Ser Ser Glu Lys Leu Asp Leu Thr Tyr Gln
        1075                1080                1085

Ser Asp Phe Ser Lys Leu Ala Glu Tyr Arg Val Gly Asp Thr Gly Leu
    1090                1095                1100

Ile Tyr Thr Pro Asn Gln Phe Leu Gln Asn His Ser Ser Ile Val Asn
1105                1110                1115                1120

Glu Val Leu Pro Asp Leu Lys Ala Val Asp Tyr Gln Ser Glu Ala Ile
                1125                1130                1135

Arg Asn Thr Leu Gly Ile Ser Ser Gly Val Ser Leu Thr Glu Leu Tyr
            1140                1145                1150

Leu Glu Glu Gln Phe Ala Lys Thr Lys Glu Asn Leu Ala Asn Thr Leu
        1155                1160                1165

Glu Lys Leu Leu Ser Ala Asp Ala Val Ile Ala Ser Glu Asn Gln Thr
        1170                1175                1180

Ile Asn Gly Tyr Val Val Asp Lys Ile Lys Arg Asn Lys Glu Ala Leu
1185                1190                1195                1200

Leu Leu Gly Leu Thr Tyr Leu Glu Arg Trp Tyr Asn Phe Asn Tyr Gly
                1205                1210                1215

Asp Val Asn Val Lys Asp Leu Val Met Tyr His Met Asp Phe Phe Gly
            1220                1225                1230

Lys Gly Asn Val Ser Pro Leu Asp Thr Ile Ile Glu Leu Gly Lys Ser
        1235                1240                1245

Gly Phe Asn Asn Leu Leu Ala Lys Asn Asn Val Asp Ala Tyr Asn Ile
```

```
                1250                1255                1260
Ser Leu Ala Asn Asn Asn Ala Thr Lys Asp Leu Phe Ser Thr Leu Ala
1265                1270                1275                1280

Asn Tyr Arg Glu Val Phe Leu Pro Asn Lys Thr Asn Asn Gln Trp Phe
                1285                1290                1295

Lys Glu Gln Thr Lys Ala Tyr Ile Val Glu Glu Lys Ser Ala Ile Asp
                1300                1305                1310

Glu Val Arg Val Lys Gln Glu Gln Ala Gly Ser Lys Tyr Ser Ile Gly
            1315                1320                1325

Val Tyr Asp Arg Ile Thr Ser Asp Thr Trp Lys Tyr Arg Asn Met Val
        1330                1335                1340

Leu Pro Leu Leu Thr Met Pro Glu Arg Ser Val Phe Val Ile Ser Thr
1345                1350                1355                1360

Ile Ser Ser Leu Gly Phe Gly Ala Tyr Asp Arg Tyr Arg Asn Asn Glu
                1365                1370                1375

His Arg Ala Gly Ala Glu Leu Asn Lys Phe Val Glu Asp Asn Ala Gln
                1380                1385                1390

Glu Thr Ala Lys Arg Gln Arg Asp His Tyr Asp Tyr Trp Tyr Arg Ile
            1395                1400                1405

Leu Asp Glu Gln Gly Arg Glu Lys Leu Tyr Arg Asn Ile Leu Val Tyr
        1410                1415                1420

Asp Ala Tyr Lys Phe Gly Asp Asp Thr Thr Val Asp Lys Ala Thr Val
1425                1430                1435                1440

Glu Ala Gln Phe Asp Ser Ser Asn Pro Ala Met Lys Tyr Phe Phe Gly
                1445                1450                1455

Pro Val Gly Asn Lys Val Val His Asn Lys His Gly Ala Tyr Ala Thr
                1460                1465                1470

Gly Asp Ser Val Tyr Tyr Met Gly Tyr Arg Met Leu Asp Lys Asp Gly
            1475                1480                1485

Ala Ile Thr Tyr Thr His Glu Met Thr His Asp Ser Asp Asn Glu Ile
        1490                1495                1500

Tyr Leu Gly Gly Tyr Gly Arg Arg Ser Gly Leu Gly Pro Glu Phe Phe
1505                1510                1515                1520

Ala Lys Gly Leu Leu Gln Ala Pro Asp His Pro Asp Asp Ala Thr Ile
                1525                1530                1535

Thr Val Asn Ser Ile Leu Lys Tyr Asp Lys Asn Asp Ala Ser Glu Lys
                1540                1545                1550

Ser Arg Leu Gln Val Leu Asp Pro Thr Lys Arg Phe Gln Asn Ala Asp
            1555                1560                1565

Asp Leu Lys Asn Tyr Val His Asn Met Phe Asp Val Ile Tyr Met Leu
        1570                1575                1580

Glu Tyr Leu Glu Gly Met Ser Ile Val Asn Arg Leu Ser Asp Val Gln
1585                1590                1595                1600

Lys Val Asn Ala Leu Arg Lys Ile Glu Asn Lys Tyr Val Arg Asp Ala
                1605                1610                1615

Asp Gly Asn Asp Val Tyr Ala Asn Val Ile Lys Asn Ile Thr Met
                1620                1625                1630

Ala Asp Ala Gln Lys Leu Asn Ser Phe Asn Ser Leu Ile Glu Asn Asp
            1635                1640                1645

Ile Leu Ser Ala Arg Glu Tyr Lys Asn Gly Asp Val Glu Arg Asn Gly
        1650                1655                1660

Tyr His Thr Ile Lys Leu Phe Ser Pro Ile Tyr Ser Ala Leu Ser Ser
1665                1670                1675                1680
```

```
Glu Lys Gly Thr Pro Gly Asp Leu Met Gly Arg Arg Ile Ala Tyr Glu
            1685                1690                1695

Leu Leu Ala Ala Lys Gly Phe Lys Asp Gly Met Val Pro Tyr Ile Ser
        1700                1705                1710

Asn Gln Tyr Glu Asp Ala Lys Gln Asn Gly Lys Thr Ile Ser Ile
    1715                1720                1725

Tyr Gly Lys Thr Arg Gly Leu Val Thr Asp Asp Leu Val Leu Arg Lys
        1730                1735                1740

Val Phe Asn Gly Gln Phe Asn Asn Trp Thr Glu Phe Lys Lys Ala Met
1745                1750                1755                1760

Tyr Glu Glu Arg Lys Asn Lys Phe Asp Ser Leu Asn Lys Val Thr Phe
            1765                1770                1775

Asp Asp Thr Arg Gln Pro Trp Thr Ser Tyr Ala Thr Lys Thr Ile Ser
        1780                1785                1790

Thr Val Glu Glu Leu Gln Thr Leu Met Asp Glu Ala Val Leu Gln Asp
            1795                1800                1805

Ala Asn Asp Asn Trp Tyr Ser Trp Ser Gly Tyr Lys Pro Glu Tyr Asn
        1810                1815                1820

Ser Ala Val His Lys Leu Lys Lys Gln Ser Ser Lys Leu Thr Ser Ile
1825                1830                1835                1840

Arg Leu Lys Ile Leu Glu Asn Gln Ser Leu Lys Thr Arg Ser Asp Trp
            1845                1850                1855

Phe Glu Gln Ser Asn
            1860

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

TCCAAAGCGA CAGTAACC                                                         18

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

CTTGGTTTGT TCTTCATCAC                                                       20

(2) INFORMATION FOR SEQ ID NO:7:

(i) SEQUENCE CHARACTERISTICS:
        (A) LENGTH: 6 amino acids
        (B) TYPE: amino acid
```

```
            (C) STRANDEDNESS:
            (D) TOPOLOGY: linear (ii) MOLECULE TYPE: protein (xi) SEQUENCE DESCRIPTION: SEQ ID NO:7:

Leu Pro Asn Thr Gly Ser
1               5

(2) INFORMATION FOR SEQ ID NO:8:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:8:

Lys Lys Lys Val Lys Asn Lys
1               5

(2) INFORMATION FOR SEQ ID NO:9:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:9:

His Xaa Xaa Thr His
1               5

(2) INFORMATION FOR SEQ ID NO:10:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:10:

Gly Tyr Ile Lys Glu Gly Lys Thr
1               5
```